(12) United States Patent
Miles et al.

(10) Patent No.: US 11,975,139 B2
(45) Date of Patent: May 7, 2024

(54) SYSTEMS AND METHODS FOR DELIVERING NITRIC OXIDE

(71) Applicant: Third Pole, Inc., Waltham, MA (US)

(72) Inventors: Christopher Miles, Acton, MA (US); Frank Heirtzler, Londonderry, NH (US); Gregory W. Hall, Belmont, MA (US); Sweta Patel, Waltham, MA (US); Wolfgang Scholz, Beverly, MA (US)

(73) Assignee: Third Pole, Inc., Waltham, MA (US)

( * ) Notice: Subject to any disclaimer, the term of this patent is extended or adjusted under 35 U.S.C. 154(b) by 0 days.

(21) Appl. No.: 17/935,055

(22) Filed: Sep. 23, 2022

(65) Prior Publication Data

US 2023/0098706 A1 Mar. 30, 2023

Related U.S. Application Data

(60) Provisional application No. 63/304,245, filed on Jan. 28, 2022, provisional application No. 63/263,319, (Continued)

(51) Int. Cl.
*A61M 15/00* (2006.01)
*A61M 11/04* (2006.01)
(Continued)

(52) U.S. Cl.
CPC .... *A61M 15/0003* (2014.02); *A61M 15/0021* (2014.02); *A61M 15/0086* (2013.01);
(Continued)

(58) Field of Classification Search
CPC .......... A61M 15/0003; A61M 15/0021; A61M 15/0085; A61M 15/0086; A61M 15/009;
(Continued)

(56) References Cited

U.S. PATENT DOCUMENTS 709,867 A 9/1902 Bradley et al.
2,485,478 A 10/1949 Cotton
(Continued)

FOREIGN PATENT DOCUMENTS

CA 2413834 6/2004
CN 1099997 3/1995
(Continued)

OTHER PUBLICATIONS

U.S. Appl. No. 15/907,241 2018/0243527 U.S. Pat. No. 10,286,176, filed Feb. 27, 2018 Aug. 30, 2018 May 14, 2019, Systems and Methods for Generating Nitric Oxide, Woodward, Valerie Lynn.
(Continued)

*Primary Examiner* — Joseph D. Boecker
(74) *Attorney, Agent, or Firm* — Greenberg Traurig, LLP; David J. Dykeman; Jaime Burke

(57) ABSTRACT

Systems and methods are provided for delivering one or more drugs. In some embodiments, a drug delivery system includes a housing having a distal end with an inlet through which an inspiratory flow of air passes into the housing, a proximal end having a patient interface attached thereto, the patient interface being configured to interface with a user, and an inspiratory flow pathway extending from the distal end to the proximal end of the housing. A nitric oxide (NO) source is positioned within the housing and is configured to deliver NO-containing gas to the patient interface. A secondary drug source is positioned within the housing and is configured to deliver a secondary drug to the patient interface. A controller is configured to control an amount of NO-containing gas and an amount of the secondary drug delivered using a control scheme.

22 Claims, 42 Drawing Sheets

Related U.S. Application Data filed on Oct. 29, 2021, provisional application No. 63/247,687, filed on Sep. 23, 2021.

(51) Int. Cl.
| | |
|---|---|
| *A61M 16/00* | (2006.01) |
| *A61M 16/10* | (2006.01) |
| *A61M 16/12* | (2006.01) |
| *A61M 16/14* | (2006.01) |
| *A61M 16/20* | (2006.01) |

(52) U.S. Cl.
CPC ...... *A61M 16/0051* (2013.01); *A61M 16/022* (2017.08); *A61M 16/10* (2013.01); *A61M 16/107* (2014.02); *A61M 16/12* (2013.01); *A61M 16/125* (2014.02); *A61M 16/14* (2013.01); *A61M 16/204* (2014.02); *A61M 11/042* (2014.02); *A61M 15/0085* (2013.01); *A61M 15/009* (2013.01); *A61M 2016/0018* (2013.01); *A61M 16/109* (2014.02); *A61M 16/122* (2014.02); *A61M 2202/0275* (2013.01); *A61M 2205/3334* (2013.01)

(58) Field of Classification Search
CPC .. A61M 16/022; A61M 16/024; A61M 16/10; A61M 16/12; A61M 16/122; A61M 16/125; A61M 16/14; A61M 16/204; A61M 2202/0275; A61M 11/00; A61M 11/042; A61M 2016/0018
See application file for complete search history.

(56) References Cited

U.S. PATENT DOCUMENTS

| | | | |
|---|---|---|---|
| 2,485,481 A | 10/1949 | Cotton | |
| 2,525,938 A | 10/1950 | Peck | |
| 2,684,448 A | 7/1954 | Nilles | |
| 3,047,370 A | 7/1962 | Aviges et al. | |
| 3,225,309 A | 12/1965 | Phelps | |
| 4,287,040 A | 9/1981 | Alamaro | |
| 4,500,563 A | 2/1985 | Ellenberger et al. | |
| 4,505,795 A | 3/1985 | Alamaro | |
| 4,680,694 A | 7/1987 | Huynh et al. | |
| 4,695,358 A | 9/1987 | Mizuno et al. | |
| 4,705,670 A | 11/1987 | O'Hare | |
| 4,816,229 A | 3/1989 | JeRnsen et al. | |
| 4,877,589 A | 10/1989 | Conrad | |
| 5,285,372 A | 2/1994 | Huynh et al. | |
| 5,378,436 A | 1/1995 | Endoh et al. | |
| 5,396,882 A * | 3/1995 | Zapol .................. | B01D 53/46 |
| | | | 128/202.25 |
| 5,413,097 A | 5/1995 | Birenheide et al. | |
| 5,471,977 A | 12/1995 | Olsson et al. | |
| 5,485,827 A | 1/1996 | Zapol et al. | |
| 5,531,218 A | 7/1996 | Krebs | |
| 5,546,935 A | 8/1996 | Champeau | |
| 5,558,083 A | 9/1996 | Bathe et al. | |
| 5,573,733 A | 11/1996 | Salama | |
| 5,674,381 A | 10/1997 | Dekker | |
| 5,692,495 A | 12/1997 | Sheu | |
| 5,732,693 A | 3/1998 | Bathe et al. | |
| 5,749,937 A | 5/1998 | Detering et al. | |
| 5,752,504 A | 5/1998 | Bathe | |
| 5,827,420 A | 10/1998 | Shirazi et al. | |
| 5,839,433 A | 11/1998 | Higenbottam | |
| 5,845,633 A | 12/1998 | Psaros | |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,186,140 B1 | 2/2001 | Hoague | |
| 6,186,142 B1 | 2/2001 | Schmidt et al. | |
| 6,197,091 B1 | 3/2001 | Ji et al. | |
| 6,224,653 B1 | 5/2001 | Shvedchikov et al. | |
| 6,250,302 B1 | 6/2001 | Rantala | |
| 6,290,683 B1 | 9/2001 | Erez et al. | |
| 6,296,827 B1 | 10/2001 | Castor et al. | |
| 6,365,868 B1 | 4/2002 | Borowy et al. | |
| 6,432,077 B1 | 8/2002 | Stenzler | |
| 6,532,956 B2 | 3/2003 | Hill | |
| 6,536,429 B1 | 3/2003 | Pavlov et al. | |
| 6,581,599 B1 | 6/2003 | Stenzler | |
| 6,668,828 B1 | 12/2003 | Figley et al. | |
| 6,758,214 B2 | 7/2004 | Fine et al. | |
| 6,920,876 B2 | 7/2005 | Miller et al. | |
| 6,955,171 B1 | 10/2005 | Figley et al. | |
| 6,955,790 B2 | 10/2005 | Castor et al. | |
| 6,984,256 B2 | 1/2006 | Lamprecht et al. | |
| 6,986,351 B2 | 1/2006 | Figley et al. | |
| 7,025,869 B2 | 4/2006 | Fine et al. | |
| 7,040,313 B2 | 5/2006 | Fine et al. | |
| 7,122,018 B2 | 10/2006 | Stenzler et al. | |
| 7,220,393 B2 | 5/2007 | Miller et al. | |
| 7,255,105 B2 | 8/2007 | Figley et al. | |
| 7,299,785 B1 | 11/2007 | Lee | |
| 7,312,584 B2 | 12/2007 | Tamita et al. | |
| 7,335,181 B2 | 2/2008 | Miller et al. | |
| 7,485,324 B2 | 2/2009 | Miller et al. | |
| 7,498,000 B2 | 3/2009 | Pekshev et al. | |
| 7,516,742 B2 | 4/2009 | Stenzler et al. | |
| 7,520,866 B2 | 4/2009 | Stenzler et al. | |
| 7,523,752 B2 | 4/2009 | Montgomery et al. | |
| 7,531,133 B2 | 5/2009 | Hole et al. | |
| 7,560,076 B2 | 7/2009 | Rounbehler et al. | |
| 7,589,473 B2 | 9/2009 | Suslov | |
| 7,597,731 B2 | 10/2009 | Palmerton et al. | |
| 7,618,594 B2 | 11/2009 | Rounbehler et al. | |
| 7,744,812 B2 | 6/2010 | Witherspoon et al. | |
| 7,861,516 B2 | 1/2011 | Allanson et al. | |
| 7,861,717 B1 | 1/2011 | Krebs | |
| 7,914,743 B2 | 3/2011 | Fine et al. | |
| 7,947,227 B2 | 5/2011 | Fine et al. | |
| 7,955,294 B2 | 6/2011 | Stenzler et al. | |
| 8,030,849 B2 | 10/2011 | Suslov | |
| 8,043,252 B2 | 10/2011 | Miller et al. | |
| 8,057,742 B2 | 11/2011 | Rounbehler et al. | |
| 8,066,904 B2 | 11/2011 | Fine et al. | |
| 8,079,998 B2 | 12/2011 | Hole et al. | |
| 8,083,997 B2 | 12/2011 | Rounbehler et al. | |
| 8,091,549 B2 | 1/2012 | Montgomery et al. | |
| 8,151,791 B2 | 4/2012 | Arlow et al. | |
| 8,173,072 B2 | 5/2012 | Fine et al. | |
| 8,187,544 B2 | 5/2012 | Fine et al. | |
| 8,211,368 B2 | 7/2012 | Fine et al. | |
| 8,221,800 B2 | 7/2012 | Fine et al. | |
| 8,226,916 B2 | 7/2012 | Rounbehler et al. | |
| 8,246,725 B2 | 8/2012 | Rounbehler et al. | |
| 8,267,884 B1 | 9/2012 | Hicks | |
| 8,268,252 B2 | 9/2012 | Fuller et al. | |
| 8,277,399 B2 | 10/2012 | Hamilton et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,328,998 B2 | 12/2012 | Wada et al. | |
| 8,344,627 B1 | 1/2013 | Hooke et al. | |
| 8,371,296 B2 | 2/2013 | Fine et al. | |
| 8,377,462 B2 | 2/2013 | DesNoyer et al. | |
| 8,397,721 B2 | 3/2013 | Montgomery et al. | |
| D679,366 S | 4/2013 | Fuller | |
| 8,408,206 B2 | 4/2013 | Montgomery et al. | |
| 8,431,163 B2 | 4/2013 | Baldassarre et al. | |
| D688,352 S | 8/2013 | Montgomery et al. | |
| 8,518,457 B2 | 8/2013 | Miller et al. | |
| 8,573,209 B2 | 11/2013 | Bathe et al. | |
| 8,573,210 B2 | 11/2013 | Bathe et al. | |
| 8,574,531 B2 | 11/2013 | Miller et al. | |
| 8,580,109 B2 | 11/2013 | Kruckenberg et al. | |
| 8,607,785 B2 | 12/2013 | Fine et al. | |
| 8,607,792 B2 | 12/2013 | Montgomery et al. | |
| 8,609,026 B2 | 12/2013 | Fine et al. | |
| 8,609,028 B2 | 12/2013 | Rounbehler et al. | |
| 8,613,958 B2 | 12/2013 | Fine | |

(56) References Cited

U.S. PATENT DOCUMENTS

| | | |
|---|---|---|
| 8,616,204 B2 | 12/2013 | Montgomery et al. |
| 8,646,445 B2 | 2/2014 | Fine et al. |
| D701,963 S | 4/2014 | Abarbanel et al. |
| 8,685,467 B2 | 4/2014 | Miller et al. |
| 8,701,657 B2 | 4/2014 | Fine et al. |
| 8,715,577 B2 | 5/2014 | Fine et al. |
| 8,717,733 B2 | 5/2014 | Gefter et al. |
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,887,721 B2 | 11/2014 | Zapol et al. |
| 8,893,717 B2 | 11/2014 | Montgomery et al. |
| 8,944,049 B2 | 2/2015 | Fine et al. |
| 9,035,045 B2 | 5/2015 | Chu et al. |
| 9,067,788 B1 | 6/2015 | Spielman et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,260,399 B2 | 2/2016 | Ruan et al. |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,994 B2 | 5/2016 | Fine et al. |
| 9,408,993 B2 | 8/2016 | Bathe et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,562,113 B2 | 2/2017 | Ruan et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,188,822 B2 | 1/2019 | Flanagan et al. |
| 10,213,572 B2 | 2/2019 | Gellman et al. |
| 10,226,592 B2 | 3/2019 | Acker et al. |
| 10,232,138 B2 | 3/2019 | Acker et al. |
| 10,239,038 B2 | 3/2019 | Zapol et al. |
| 10,279,139 B2 | 5/2019 | Zapol et al. |
| 10,286,176 B2 | 5/2019 | Zapol et al. |
| 10,293,133 B2 | 5/2019 | Zapol et al. |
| 10,328,228 B2 | 6/2019 | Zapol et al. |
| 10,398,820 B2 | 9/2019 | Potenziano et al. |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 | 3/2020 | Zapol et al. |
| 10,646,682 B2 | 5/2020 | Zapol et al. |
| 10,682,486 B1 | 6/2020 | Moon et al. |
| 10,695,523 B2 | 6/2020 | Zapol et al. |
| 10,737,051 B2 | 8/2020 | Gellman et al. |
| 10,750,606 B1 | 8/2020 | Liu et al. |
| 10,758,703 B2 | 9/2020 | Kohlmann et al. |
| 10,773,046 B2 | 9/2020 | Schnitman et al. |
| 10,773,047 B2 | 9/2020 | Zapol et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 11,007,503 B2 | 5/2021 | Zapol et al. |
| 11,033,705 B2 | 6/2021 | Zapol et al. |
| 11,045,620 B2 | 6/2021 | Hall et al. |
| 11,376,390 B2 | 7/2022 | Gillerman et al. |
| 11,478,601 B2 | 10/2022 | Hall et al. |
| 11,479,464 B2 | 10/2022 | Hall et al. |
| 11,524,134 B2 | 12/2022 | Zapol et al. |
| 11,554,240 B2 | 1/2023 | Hall et al. |
| 11,660,416 B2 | 5/2023 | McAuley et al. |
| 11,691,879 B2 | 7/2023 | Kondiboyina et al. |
| 11,827,989 B2 | 11/2023 | Silkoff et al. |
| 11,833,309 B2 | 12/2023 | Gillerman et al. |
| 11,877,378 B2 | 1/2024 | Wu et al. |
| 2001/0031230 A1 | 10/2001 | Castor et al. |
| 2001/0035186 A1 | 11/2001 | Hill |
| 2002/0111748 A1 | 8/2002 | Kobayashi et al. |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0050387 A1 | 3/2004 | Younes |
| 2004/0149282 A1 | 8/2004 | Hickle |
| 2004/0168686 A1 | 9/2004 | Krebs |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0274381 A1 | 12/2005 | Deane et al. |
| 2005/0281465 A1 | 12/2005 | Marquart et al. |
| 2006/0025700 A1 | 2/2006 | Fallik |
| 2006/0090759 A1 | 5/2006 | Howes et al. |
| 2006/0172018 A1 | 8/2006 | Fine et al. |
| 2006/0173396 A1 | 8/2006 | Hatamian et al. |
| 2006/0207594 A1 | 9/2006 | Stenzler et al. |
| 2006/0276844 A1 | 12/2006 | Alon et al. |
| 2007/0051712 A1 | 3/2007 | Kooken et al. |
| 2007/0113851 A1 | 5/2007 | Delisle et al. |
| 2007/0151561 A1 | 7/2007 | Laurila |
| 2007/0181126 A1 | 8/2007 | Tolmie et al. |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2010/0030091 A1 | 2/2010 | Fine |
| 2010/0043789 A1 | 2/2010 | Fine et al. |
| 2010/0076325 A1 | 3/2010 | Cho et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 | 6/2011 | Moore et al. |
| 2011/0240019 A1 | 10/2011 | Fine et al. |
| 2012/0093948 A1 | 4/2012 | Fine et al. |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1 | 5/2014 | Fine et al. |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0155684 A1 | 6/2014 | Ehrenreich |
| 2014/0158121 A1 | 6/2014 | Flanagan et al. |

(56) References Cited

U.S. PATENT DOCUMENTS

| | | |
|---|---|---|
| 2014/0166009 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0075522 A1* | 3/2015 | Acker .................. G16H 50/20 128/203.14 |
| 2015/0090261 A1 | 4/2015 | Crosbie |
| 2015/0101604 A1 | 4/2015 | Crosbie |
| 2015/0174158 A1 | 6/2015 | Av-Gay et al. |
| 2015/0190565 A1 | 7/2015 | Ohdaira et al. |
| 2015/0272988 A1 | 10/2015 | Av-Gay et al. |
| 2015/0328430 A1 | 11/2015 | Miller et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0045685 A1* | 2/2016 | Hyde .................. A61M 15/008 128/200.14 |
| 2016/0106946 A1 | 4/2016 | Gellman et al. |
| 2016/0106949 A1 | 4/2016 | Kohlmann et al. |
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0193336 A1 | 7/2016 | Nelson et al. |
| 2016/0228670 A1 | 8/2016 | Av-Gay et al. |
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0112871 A1 | 4/2017 | Nelson et al. |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2017/0296463 A1 | 10/2017 | Minton et al. |
| 2017/0348503 A1 | 12/2017 | Westermark |
| 2018/0049622 A1 | 2/2018 | Ryan et al. |
| 2018/0071467 A1 | 3/2018 | Fine et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0228836 A1 | 8/2018 | Nelson et al. |
| 2018/0243527 A1 | 8/2018 | Zapol et al. |
| 2018/0243528 A1 | 8/2018 | Zapol et al. |
| 2018/0264032 A1* | 9/2018 | Jafri .................. A61K 33/08 |
| 2018/0280920 A1 | 10/2018 | Zapol et al. |
| 2018/0296790 A1 | 10/2018 | Zapol et al. |
| 2018/0304038 A1* | 10/2018 | Jafri .................. A61M 16/201 |
| 2018/0311460 A1 | 11/2018 | Rounbehler et al. |
| 2018/0328842 A1 | 11/2018 | Kjaer |
| 2019/0038864 A1 | 2/2019 | Montgomery et al. |
| 2019/0083699 A1 | 3/2019 | Spohn et al. |
| 2019/0092639 A1 | 3/2019 | Fine et al. |
| 2019/0127223 A1 | 5/2019 | Montgomery et al. |
| 2019/0134574 A1 | 5/2019 | Tsuchiaya et al. |
| 2019/0135633 A1 | 5/2019 | Montgomery et al. |
| 2019/0143068 A1 | 5/2019 | Rounbehler et al. |
| 2019/0184116 A1 | 6/2019 | Acker et al. |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0030553 A1 | 1/2020 | Keip et al. |
| 2020/0094011 A1 | 3/2020 | Zapol et al. |
| 2020/0139071 A1 | 5/2020 | Fine et al. |
| 2020/0139072 A1 | 5/2020 | Zapol et al. |
| 2020/0139073 A1 | 5/2020 | Tector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0188319 A1 | 6/2020 | Quinn et al. |
| 2020/0197318 A1 | 6/2020 | Widgerow et al. |
| 2020/0254199 A1 | 8/2020 | Bassin |
| 2020/0282375 A1 | 9/2020 | Fine et al. |
| 2020/0308032 A1 | 10/2020 | Domrese et al. |
| 2020/0360647 A1 | 11/2020 | Quinn et al. |
| 2020/0360649 A1 | 11/2020 | Hall et al. |
| 2020/0360690 A1 | 11/2020 | Evans et al. |
| 2020/0361772 A1 | 11/2020 | Hall et al. |
| 2020/0361773 A1 | 11/2020 | Gillerman et al. |
| 2020/0390994 A1 | 12/2020 | Gillerman et al. |
| 2021/0214222 A1 | 7/2021 | Kondiboyia et al. |
| 2021/0220586 A1 | 7/2021 | Shah et al. |
| 2021/0268221 A1 | 9/2021 | Gillerman et al. |
| 2021/0330957 A1 | 10/2021 | Potenziano et al. |
| 2021/0353898 A1 | 11/2021 | Hall et al. |
| 2021/0386954 A1 | 12/2021 | Tamiya et al. |
| 2021/0395905 A1 | 12/2021 | Silkoff et al. |
| 2022/0047837 A1 | 2/2022 | Zapol et al. |
| 2022/0080147 A1 | 3/2022 | Shah et al. |
| 2022/0096535 A1 | 3/2022 | Shah et al. |
| 2022/0135406 A1 | 5/2022 | Apollonio et al. |
| 2022/0162070 A1 | 5/2022 | Silkoff et al. |
| 2022/0193623 A1 | 6/2022 | Nakao |
| 2022/0211967 A1 | 7/2022 | Hall et al. |
| 2022/0296845 A1 | 9/2022 | Jackson et al. |
| 2022/0298653 A1 | 9/2022 | Silkoff et al. |
| 2022/0339391 A1 | 10/2022 | Gillerman et al. |
| 2023/0001119 A1 | 1/2023 | Richardson et al. |
| 2023/0053201 A1* | 2/2023 | Miles .................. C01B 21/32 |
| 2023/0098706 A1 | 3/2023 | Miles et al. |
| 2023/0112963 A1 | 3/2023 | Yuen et al. |
| 2023/0149556 A1 | 5/2023 | Hall et al. |
| 2023/0158064 A1 | 5/2023 | Shah |
| 2023/0158260 A1 | 5/2023 | Shah et al. |
| 2023/0158261 A1 | 5/2023 | Trias et al. |
| 2023/0201497 A1 | 6/2023 | Dekker |
| 2023/0263986 A1 | 8/2023 | Hall et al. |
| 2023/0330359 A1 | 10/2023 | Scholz et al. |
| 2024/0067523 A1 | 2/2024 | Hall et al. |
| 2024/0076185 A1 | 3/2024 | Hall et al. |
| 2024/0076186 A1 | 3/2024 | Kondiboyina et al. |

FOREIGN PATENT DOCUMENTS

| | | |
|---|---|---|
| CN | 1730115 | 2/2006 |
| CN | 201037113 | 3/2008 |
| CN | 100404083 | 7/2008 |
| CN | 101036482 | 12/2010 |
| CN | 110872714 | 3/2020 |
| DE | 101 51 270 | 10/2006 |
| EP | 621051 | 10/1994 |
| EP | 0763500 | 3/1997 |
| EP | 0878208 | 11/1998 |
| EP | 1036758 | 9/2000 |
| EP | 2151554 | 2/2010 |
| EP | 1854494 | 6/2012 |
| EP | 2565157 | 10/2017 |
| EP | 3372267 | 12/2018 |
| JP | H04132560 | 5/1992 |
| JP | 2000102616 | 4/2000 |
| JP | 2003339872 A | 12/2003 |

(56) References Cited

FOREIGN PATENT DOCUMENTS

| | | | | |
|---|---|---|---|---|
| JP | 2004065636 | 3/2004 | | |
| JP | 2006273677 | 10/2006 | | |
| KR | 100841741 | 6/2008 | | |
| KR | 20100087977 | 8/2010 | | |
| RU | 2199167 | 2/2003 | | |
| WO | WO199507610 | 3/1995 | | |
| WO | WO2004032719 | 4/2004 | | |
| WO | WO2005094138 | 10/2005 | | |
| WO | WO2005110441 | 11/2005 | | |
| WO | WO2008/019102 | 2/2008 | | |
| WO | WO2008/112143 | 9/2008 | | |
| WO | 2008116991 A2 | 10/2008 | | |
| WO | WO2009018837 | 2/2009 | | |
| WO | WO2010021944 | 2/2010 | | |
| WO | WO2011/002606 | 1/2011 | | |
| WO | WO2012014805 | 2/2012 | | |
| WO | WO2012/034089 | 3/2012 | | |
| WO | WO2012/094008 | 7/2012 | | |
| WO | WO2012/155213 | 11/2012 | | |
| WO | WO2013/052548 | 4/2013 | | |
| WO | WO-2013052548 A2 * | 4/2013 | ............ | A61K 33/00 |
| WO | WO2013/070712 | 5/2013 | | |
| WO | WO2013/181179 | 12/2013 | | |
| WO | WO2014/085719 | 6/2014 | | |
| WO | WO2014/143842 | 9/2014 | | |
| WO | WO2014/144151 | 9/2014 | | |
| WO | WO-2014143842 A1 * | 9/2014 | ............ | A61M 15/02 |
| WO | WO2015/049783 | 4/2015 | | |
| WO | WO2015/066278 | 5/2015 | | |
| WO | WO2015/127085 | 8/2015 | | |
| WO | WO2016/064863 | 4/2016 | | |
| WO | WO2018/157172 | 8/2018 | | |
| WO | WO2018/157175 | 8/2018 | | |
| WO | WO2019/046413 | 3/2019 | | |
| WO | WO2019/046415 | 3/2019 | | |
| WO | WO2019/133776 | 7/2019 | | |
| WO | WO2019/133777 | 7/2019 | | |
| WO | WO2019/222640 | 11/2019 | | |
| WO | WO2020/033768 | 2/2020 | | |
| WO | WO2020/115473 | 6/2020 | | |
| WO | WO2020/142658 | 7/2020 | | |
| WO | WO2020/148155 | 7/2020 | | |
| WO | WO2020/150195 | 7/2020 | | |
| WO | WO2020/232414 | 11/2020 | | |
| WO | WO2020/232419 | 11/2020 | | |
| WO | WO2021/087382 | 5/2021 | | |
| WO | WO2021/142472 | 7/2021 | | |
| WO | 2021154833 A2 | 8/2021 | | |
| WO | WO2021/245667 | 12/2021 | | |
| WO | WO2021/258025 | 12/2021 | | |
| WO | WO2022/123574 | 6/2022 | | |
| WO | WO2022/123580 | 6/2022 | | |
| WO | WO2022/2123567 | 6/2022 | | |
| WO | 2022192757 A1 | 9/2022 | | |
| WO | 2023018992 A1 | 2/2023 | | |
| WO | 2023049873 A1 | 3/2023 | | |
| WO | 2023092103 A1 | 5/2023 | | |
| WO | 2023201363 A1 | 10/2023 | | |

OTHER PUBLICATIONS

U.S. Appl. No. 15/907,258 2018/0243528 U.S. Pat. No. 10,328,228, filed Feb. 27, 2018 Aug. 30, 2018 Jun. 25, 2019, Systems and Methods for Ambulatory Generation of Nitric Oxide, Woodward, Valerie Lynn.

U.S. Appl. No. 16/363,505 2019/0217042 U.S. Pat. No. 10,576,329, filed Mar. 25, 2019 Jul. 18, 2019 Mar. 3, 2020, Systems and Methods for Ambulatory Generation of Nitric Oxide, Woodward, Valerie Lynn.

U.S. Appl. No. 16/388,464 2019/0314596 U.S. Pat. No. 10,532,176, filed Apr. 18, 2019 Oct. 17, 2019 Jan. 14, 2020, Systems and Methods for Generating Nitric Oxide, Woodward, Valerie Lynn.

U.S. Appl. No. 16/697,498 2020/0094011 U.S. Pat. No. 10,695,523, filed Nov. 27, 2019 Mar. 26, 2020 Jun. 30, 2020, Systems and Methods for Generating Nitric Oxide, Woodward, Valerie Lynn.

U.S. Appl. No. 16/724,233 2020/0139072 U.S. Pat. No. 11,033,705, filed Dec. 21, 2019 May 7, 2020 Jun. 15, 2021, Systems and Methods for Ambulatory Generation of Nitric Oxide, Woodward, Valerie Lynn.

U.S. Appl. No. 16/875,971 2020/0361772 U.S. Pat. No. 11,479,464, filed May 15, 2020 NOv. 19, 2020 Oct. 25, 2022, Systems and Methods for Generating Nitric Oxide, Tai, Xiuyu.

U.S. Appl. No. 16/875,687 2020/0360649 U.S. Pat. No. 11,045,620, filed May 15, 2020 Nov. 19, 2020 Jun. 29, 2021, Electrodes for Nitric Oxide Generation, Tai, Xiuyu.

U.S. Appl. No. 16/875,914 2020/0361773, filed May 15, 2020 Nov. 19, 2020, Architectures for Production of Nitric Oxide, Fetterolf, Brandon J.

U.S. Appl. No. 17/146,468 2021-0214222, filed Jan. 11, 2021 Jul. 15, 2021, Systems and Methods for Nitric Oxide Generation with Humidity Control, Tai, Xiuyu.

U.S. Appl. No. 16/909,722 2020/0390994 U.S. Pat. No. 10,946,163, filed Jun. 23, 2020 Dec. 17, 2020 Mar. 16, 2021, Systems and Methods for Generating Nitric Oxide, Woodward, Valerie Lynn.

U.S. Appl. No. 17/197,911 2021/0268221 U.S. Pat. No. 11,376,390, filed Mar. 10, 2021 Sep. 2, 2021 Jul. 5, 2022, Systems and Methods for Generating Nitric Oxide, Woodward, Valerie Lynn.

U.S. Appl. No. 17/332,915 2022/0047837 U.S. Pat. No. 11,524,134, filed May 27, 2021 Feb. 17, 2022 Dec. 13, 2022, Systems and Methods for Ambulatory Generation of Nitric Oxide, Woodward, Valerie Lynn.

U.S. Appl. No. 17/331,793 2021/0353898 U.S. Pat. No. 11,478,601, filed May 27, 2021 Nov. 18, 2021 Oct. 23, 2021, Systems and Methods for Preventing and Treating Infections with Nitric Oxide, Tai, Xiuyu.

U.S. Appl. No. 17/352,225 2021/0395905, filed Jun. 18, 2021 Dec. 23, 2021, Systems and Methods for Preventing and Treating Infections with Nitric Oxide, Tai, Xiuyu.

U.S. Appl. No. 17/503,223 2022/0135406, filed Oct. 15, 2021 May 5, 2022, Nitric Oxide Generation Process Controls.

U.S. Appl. No. 17/670,655 2022/0162070, filed Feb. 14, 2022 May 26, 2022, Systems and Methods for Generating Nitric Oxide, Annette Fredricka Dixon.

U.S. Appl. No. 17/693,279 2022/0296845, filed Mar. 11, 2022 Sep. 22, 2022, Systems and Methods for Nitric Oxide Generation and Delivery.

U.S. Appl. No. 17/703,497 2022/0211967 U.S. Pat. No. 11,554,240, filed Mar. 24, 2022 Jul. 7, 2022 Jan. 17, 2023, Systems and Methods for Ambulatory Generation of Nitric Oxide, Valerie Lynn Woodward.

U.S. Appl. No. 17/773,369 2023/0001119, filed Apr. 29, 2022 Jan. 5, 2023, Systems and Methods for Increasing Nitrogen Monoxide Concentration and Removing Nitrogen Dioxide from a Gas Stream.

U.S. Appl. No. 17/837,416 2022/0298653, filed Jun. 10, 2022 Sep. 22, 2022, Systems and Methods for Preventing and Treating Infections with Nitric Oxide, Tai, Xiuyu.

U.S. Appl. No. 17/855,592 20022/0339391, filed Jun. 30, 2022 Oct. 27, 2022, Systems and Methods for Generating Nitric Oxide, Valerie Lynn Woodward.

U.S. Appl. No. 17/819,582, filed Aug. 12, 2022, Systems and Methods for Generating Nitric Oxide Using Microwave Energy.

U.S. Appl. No. 18/049,013, filed Oct. 24, 2022, Electrodes for Nitric Oxide Generation.

U.S. Appl. No. 18/057,145, filed Nov. 18, 2022, Systems and Methods for Breath Detection, Luarca, Margaret M.

U.S. Appl. No. 18/065,337, filed Dec. 13, 2022, Systems and Methods for Ambulatory Generation of Nitric Oxide.

Arjunan Thesis—Plasma Produced Reactive Oxygen and Nitrogen Species in Angiogenesis—May 2011—Krishna Priya Arjunan.

Arora et al., Nitric Oxide Regulation of Bacterial Biofilms, Biochemistry, vol. 54, pp. 3717-3728, May 21, 2015.

Barraud et al., Involvement of Nitric Oxide n Biofilm Dispersal of Pseudomonas Aeruginosa, Journal of Bacteriology, vol. 188, No. 21, pp. 7344-7353, Nov. 2006.

Bellerophon, "A Dose Escalation Study to Assess the Safety and Efficacy of Pulsed iNO in Subjects With Pulmonary Fibrosis", Aug. 30, 2017, https://clinicaltrials.gov/ct2/show/NCT03267108.

(56) References Cited

OTHER PUBLICATIONS

Bentur et al., Pilot Study to Test Inhaled Nitric Oxide in Cystic Fibrosis Patients with Refractory Mycobacterium Abscessus Lung Infection, Journal of Cystic Fibrosis, vol. 19, pp. 225-231, May 23, 2019.
Birkeland, K., "On the Oxidation of Atmospheric Nitrogen in Electric Arcs", A Paper read before the Faraday Society on Monday, Jul. 2, 1906, Published on Jan. 1, 1906.
Bogdonovski et al., Anti-Mycobacterial Activity of High-Dose Nitric Oxide Against Mycobacterium Abscessus In Vitro, National Institutes of Health Poster, Jul. 8, 2018.
Charles, et al., "SiO2 Deposition from Oxygen/Silane Pulsed Helicon Diffusion Plasmas" Applied Physics Letters, vol. 67, No. 1, pp. 40-42, Jul. 3, 1995.
Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.
Dobrynin et al. "Direct and Controllable Nitric Oxide Delivery into Biological Media and Living Cells by a Pin-to-Hole Spark Discharge (PHD) Plasma" Journal of Physics D: Applied Physics, vol. 44, pp. 1-10, Jan. 28, 2011.
Donohoe et al., "Production of O3, NO, and N2O in a Pulsed Discharge at 1 Atm", Ind. Eng. Chem., Fundam., vol. 16, No. 2, pp. 208-215, May 1977.
Encyclopaedia Britannica, "Soda Lime" published Nov. 12, 2018, https://www.britannica.com/science/soda-lime.
Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.
Fowler, "Exercise Intolerance in Pulmonary Arterial Hypertension", Pulmonary Medicine, vol. 2012, Article ID 39204, 11 pages, (2012).
Habib, Bassam Hanna, "A Simple Model of Spark Gap Discharge Phase", Eng. & Tech. Journal, vol. 31, Part (A), No. 9, pp. 1692-1704, 2013.
Hanning et al., "Pulse Oximetry: A Practical Review", British Medical Journal, vol. 311, pp. 367-370, Aug. 5, 1995.
Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).
Higenbottam et al., "The Direct and Indirect Action of Inhaled Agents on the Lung and Its Circulation: Lessons from Clinical Science," Environmental Health Perspectives, vol. 109, Supplement 4, pp. 559-562, Aug. 2001.
Howlin et al., Low-Dose Nitric Oxide as Targeted Anti-Biofilm Adjunctive Therapy to Treat Chronic Pseudomonas Aeruginosa Infection in Cystic Fibrosis, Molecular Therapy, vol. 25, No. 9, pp. 2104-2116, Sep. 2017.
Hu, Hui et al., "Study on Production of Nitric Monoxide for Respiratory Distress by Pulsed Discharge", Proceedings of the CSEE, vol. 23, No. 2, Jan. 2005.
Hu, Hui et al., "Study on Pulsed Arc Discharge Conditions on Production of Nitric Oxide for Medical Application", High Voltage Apparatus, Issue 3, Mar. 2005.
Hu et al., "Study on Production of Inhaled Nitric Oxide for Medical Applications by Pulsed Discharge" IEEE Transactions on Plasma Science, vol. 35, No. 3, pp. 619-625, Jun. 2007.
Hu, Hui et al., "The Effect of Flow Distribution on the Concentration of NO Produced by Pulsed Arc Discharge", Plasma Science and Technology, vol. 9, No. 6, pp. 766-769, Dec. 2007.
Hu, Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages (Includes English Language Translation of Title Page and Abstract).

Intersurgical Complete Respiratory Systems, Carbon Dioxide Absorbents Catalogue, www.intersurgical.com/distributors, Issue 5, Oct. 17, 2021.
Johns Hopkins University—"American Chemical Journal vol. XXXV"—No. 4, Reports Chapter, pp. 358-368, Apr. 1906.
Keshav, Saurabh. "Using Plasmas for High-speed Flow Control and Combustion Control" Diss. The Ohio State University, 2008.
Kornev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.
Kuo, Spencer P. "Air Plasma for Medical Applications" J. Biomedical Science and Engineering, vol. 5, pp. 481-495, Sep. 2012.
Li, Z. et al., "Development of Miniature Pulsed Power Generator," 2005 IEEE Pulsed Power Conference, Monterey, CA, pp. 1053-1056, Jul. 2005.
Li et al., Production of Medically Useful Nitric Monoxide Using AC Arc Discharge, Nitric Oxide, vol. 73, pp. 89-95, Feb. 28, 2018.
Lorente L., "Respiratory Filters and Ventilator-Associated Pneumonia: Composition, Efficacy Tests and Advantages and Disadvantages", Humidification in the Intensive Care Unit, pp. 171-177, Springer, Berlin, Heidelberg 2012.
Lovich et al., "Generation of Purified Nitric Oxide from Liquid N204 for the Treatment of Pulmonary Hypertension in Hypoxemic Swine", Nitric Oxide vol. 37, pp. 66-77, Feb. 15, 2014.
Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.
McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.
Miller et al., Gaseous Nitric Oxide Bactericidal Activity Retained During Intermittent High-Dose Short Duration Exposure, Nitric Oxide, vol. 20, Issue 1, pp. 16-23, Feb. 2009.
Miller et al., Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.
Miller et al., Nitric Oxide is a Potential Antimicrobial Against Slow and Fast Growing Mycobacteria, Online Abstracts Issue, American Journal Respiratory Care Medicine, vol. 193, A7498, May 18, 2016.
Miller et al., A Phase I Clinical Study of Inhaled Nitric Oxide in Healthy Adults, Journal of Cystic Fibrosis, vol. 11, pp. 324-331, Apr. 18, 2012.
Mok et al. "Application of Positive Pulsed Corona Discharge to Removal of SO2 and NOx," Proceedings, ICESP VII, Sep. 20-25, 1998, Kyongiu, Korea.
Namihira et al., Production of Nitric Monoxide Using Pulsed Discharges for a Medical Application, IEEE Transactions on Plasma Science, vol. 28, No. 1, pp. 109-114, Feb. 2000.
Namihara et al., "Production of NO Using Pulsed Arc Discharges and Its Medical Applications", Journal of Plasma and Fusion Research, vol. 79, No. 1 pp. 35-38, Jun. 25, 2002.
Namihira et al., "Production of Nitric Monoxide in Dry Air Using Pulsed Discharge," Digest of Technical Papers. 12th IEEE International Pulsed Power Conference. (Cat. No.99CH36358), Monterey, CA, pp. 1313-1316 vol. 2, Aug. 6, 2002.
Namihira et al., Production of Nitric Oxide Using a Pulsed Arc Discharge, IEEE Transactions on Plasma Science, vol. 30, No. 5, pp. 1993-1998, Oct. 2002.
Namihira et al., "Temperature and Nitric Oxide Generation in a Pulsed Arc Discharge Plasma" Plasma Science and Technology, vol. 9, No. 6, pp. 747-751, Dec. 2007.
Navarro-Gonzalez et al., "The Physical Mechanism of Nitric Oxide Formation in Simulated Lightning" Geophysical Research Letters, vol. 28, No. 20, pp. 3867-3870, Oct. 15, 2001.
Olivier et al., Treatment of Refractory Mycobacterium Abscessus Lung Infection with Inhaled Intermittent Nitric Oxide, Poster, Jul. 8, 2018.
Overzet, et al. "Why and How to Pulse a Plasma"—slide show presentation, Oct. 1997.
Patil et al., Plasma Assisted Nitrogen Oxide Production from Air, AIChE Journal, vol. 64, Issue 2, Aug. 14, 2017.

(56) References Cited

OTHER PUBLICATIONS

Pawlat et al., Evaluation of Oxidative Species in Gaseous, Plasma Chemistry and Plasma Processing, vol. 39, pp. 627-642, Mar. 28, 2019.
Pontiga, F., et al., "Nitrogen Oxides Generation Induced by Negative Corona Discharge in N2 + O2 Mixtures," 2006 IEEE Conference on Electrical Insulation and Dielectric Phenomena, Kansas City, MO, pp. 264-267, Oct. 2006.
Sakai, et al., "A Compact Nitric Oxide Supply for Medical Application," 2007 16th IEEE International Pulsed Power Conference, Albuquerque, NM, pp. 752-755, Oct. 14, 2008.
Sakai et al., "Nitric Oxide Generator Based on Pulsed Arc Discharge" Acta Physica Polonica A, vol. 115, No. 6, pp. 1104-1106, Jun. 2009.
Schilz, "Treatment of Pulmonary Hypertension Related to Disorders of Hypoxia" Advances in Pulmonary Hypertension, vol. 4, No. 2, pp. 14-22, May 2005.
Takaki, et al., "Resistance of Pulsed Arc Discharge in Air and SF/sub 6", Pulsed Power Plasma Science, vol. 2, pp. 1758-1761, Jun. 2001.
Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.
Tsukahara et al., "Gas-Phase Oxidation of Nitric Oxide: Chemical Kinetics and Rate Constant," Nitric Oxide: Biology and Chemistry, vol. 3, No. 3, pp. 191-198, Jun. 1999.
Wang et al., Gliding Arc Plasma for CO2 Conversion, Chemical Engineering Journal, vol. 330, pp. 11-25, 2017.
Yaacoby-Bianu et al., Compassionate Nitric Oxide Adjuvant Treatment of Persistent Mycobacterium Infection in Cystic Fibrosis Patients, The Pediatric Infectious Disease Journal, vol. 37, No. 4, Apr. 2018.
Yu, et al., "Detection and Removal of Impurities in Nitric Oxide Generated from Air by Pulsed Electrical Discharge", Nitric Oxide, vol. 60, pp. 16-23, Nov. 30, 2016.
Yu, et al. "Development of a Portable Mini-Generator to Safely Produce Nitric Oxide for the Treatment of Infants with Pulmonary Hypertension", Nitric Oxide, vol. 75, pp. 7-76, May 1, 2018.
International Search Report in International PCT Patent Application No. PCT/US2022/76981 mailed Dec. 14, 2022.

\* cited by examiner

| Parameter | Units | Sc. 1 | Sc. 2 | Sc. 3 | Sc. 4 |
|---|---|---|---|---|---|
| Inhaled volume | ml | 500 | 500 | 500 | 200 |
| Inspiratory flow rate limit | lpm | 30 | 6 | 3 | 1.2 |
| Inspiration duration | seconds | 1 | 5 | 10 | 10 |
| Product gas flow rate | lpm | 30 | 6 | 3 | 1.2 |
| Target Inhaled NO Concetration | ppm | 200 | 200 | 200 | 200 |
| Required NO Production | ppm.lpm | 6000 | 1200 | 600 | 240 |

FIG. 28

SYSTEMS AND METHODS FOR DELIVERING NITRIC OXIDE

RELATED APPLICATIONS

This application claims the benefit of and priority to U.S. Provisional Application Ser. No. 63/304,245, filed on Jan. 28, 2022, U.S. Provisional Application Ser. No. 63/263,319, filed on Oct. 29, 2021, and U.S. Provisional Application Ser. No. 63/247,687, filed on Sep. 23, 2021, and the contents of each of these applications which is incorporated herein by reference in their entireties.

FIELD

The present disclosure relates to systems and methods for delivering and/or generating nitric oxide.

BACKGROUND

Nitric oxide is a pulmonary vasodilator routinely used in a hospital setting to improve patient oxygenation. This molecule has the potential to provide similar benefits to users outside of a clinical setting as well. Exemplary out-of-hospital applications are for treating infection, preventing infection, treating altitude sickness and boosting athletic performance.

After 20 years of clinical use, the safety profile of NO is well known with two primary issues: oxidation and methemoglobinemia. NO reacts with oxygen to create nitrogen dioxide (NO2), a compound that is toxic when inhaled. NO2 can be removed from a gas stream with various scrubbing technologies. High doses of NO can result in a condition called "methemoglobinemia", a condition where hemoglobin molecules in the blood that typically transport oxygen are occupied by NO molecules, decreasing the ability of a user to uptake oxygen and creating a risk of kidney damage. Limiting the dose of NO to target treatment levels is a key aspect to any NO delivery device.

SUMMARY

The present disclosure is directed to systems, methods and devices for nitric oxide delivery to an inspiratory flow using an inhaler device. In some embodiments, the device is single use and disposable, and in some embodiments the device can include a reusable component. In some embodiments, NO is delivered directly to an inspiratory flow, and in some embodiments, NO is delivered to a patient through a delivery device or concomitant therapy device. In some embodiments, the NO generation device may solely deliver NO or deliver additional drugs and/or gases from the same device. In some embodiments, more than one drug is delivered, for example, NO and a secondary drug.

A drug delivery system is provided, and in some embodiments can comprise a housing having a distal end with an inlet through which an inspiratory flow of air passes into the housing, a proximal end having a patient interface attached thereto, the patient interface being configured to interface with a user, and an inspiratory flow pathway extending from the distal end of the housing to the proximal end of the housing. A nitric oxide (NO) source is positioned within the housing, and the NO source configured to deliver NO-containing gas to the patient interface. A secondary drug source is positioned within the housing, and the secondary drug source configured to deliver a secondary drug to the patient interface. A controller is configured to control an amount of NO-containing gas delivered from the NO source and an amount of the secondary drug delivered from the secondary drug source using a control scheme, the control scheme having one or more inputs relating to at least one of the NO-containing gas, the secondary drug, the inspiratory flow pathway, and one or more inputs from a user. The controller is configured to communicate with one more sensors configured to collect information relating to the one or more inputs to the control scheme. At least one of the one or more inputs relates to detection of an inspiratory event associated with the inspiratory flow.

In some embodiments, the user draws gas through the patient interface to inhale the NO-containing gas and the secondary drug simultaneously. In some embodiments, the NO-containing gas is configured to increase uptake of the secondary drug. In some embodiments, a dose of NO-containing gas is in a range of 1 to 80 ppm. In some embodiments, a dose of NO-containing gas is in a range of 1 to 1000 ppm.

In some embodiments, the drug delivery system further includes a vaporization chamber configured to heat the secondary drug to vaporize the secondary drug. In some embodiments, the drug delivery system further includes a nebulization chamber configured to nebulize a secondary drug. In some embodiments, the drug delivery system further includes one or more of a pressure regulator and a valve to control the flow of secondary drug from the secondary drug source, the secondary drug source being in the form of a pressurized container.

In some embodiments, the controller is configured to control an amount of the secondary drug delivered from the secondary drug source. In some embodiments, the controller is configured to deliver the NO-containing gas and the secondary drug using first and second independent delivery schedules.

In some embodiments, the NO source comprises a compressed gas cylinder. In some embodiments, the NO source comprises an electric NO generator. In some embodiments, the NO-containing gas is generated from heating N2O4 to make NO2 gas and reducing the NO2 gas to NO with a reducing agent.

In some embodiments, the drug delivery system further includes at least one of a scrubber configured to remove NO2 from the NO-containing gas and a particle filter configured to remove contaminants from the NO-containing gas.

In some embodiments, the NO-containing gas is delivered from the NO source directly to the patient interface. In some embodiments, the NO-containing gas is delivered from the NO source to the patient interface via the inspiratory flow pathway. In some embodiments, the secondary drug is delivered from the secondary drug source directly to the patient interface. In some embodiments, the secondary drug is delivered from the secondary drug source directly to the patient interface via the inspiratory flow pathway.

In some embodiments, a drug delivery system is provided that comprises a housing having a distal end having an inlet through which an inspiratory flow of air passes into the housing, an inspiratory flow pathway, and a proximal end having a patient interface attached thereto, the patient interface being configured to interface with a user. An electric nitric oxide (NO) generator is positioned in the housing and configured to generate NO-containing gas in a plasma chamber with one or more pairs of electrodes therein by ionizing at least a portion of the inspiratory flow of air through the plasma chamber. A secondary drug source is positioned in the housing and configured to provide a secondary drug. A controller is configured to control an amount of NO-containing gas delivered from the electric NO generator and an amount of the secondary drug from the secondary drug source using a control scheme, the control scheme having one or more inputs relating to at least one of the NO-containing gas, the secondary drug, the inspiratory flow of air, and one or more inputs from a user. The controller is configured to communicate with one more sensors configured to collect information relating to the one or more inputs to the control scheme.

In some embodiments, the user draws gas through the patient interface to inhale the NO-containing gas and the secondary drug simultaneously. In some embodiments, the NO-containing gas is configured to increase uptake of the secondary drug.

In some embodiments, a drug delivery system is provided that comprises a housing having a distal end with an inlet through which an inspiratory flow of air passes into the housing, a proximal end having a patient interface attached thereto, the patient interface being configured to interface with a user, and an inspiratory flow pathway extending from the distal end of the housing to the proximal end of the housing. A nitric oxide (NO) source is positioned within the housing, and the NO source is configured to deliver NO-containing gas. A secondary drug source is positioned within the housing, and the secondary drug source is configured to deliver a secondary drug, A controller is configured to control an amount of NO-containing gas delivered from the NO source and an amount of the secondary drug delivered from the secondary drug source using a control scheme, the control scheme having one or more inputs relating to at least one of the NO-containing gas, the secondary drug, the inspiratory flow pathway, and one or more inputs from a user. The controller is configured to communicate with one or more sensors configured to collect information relating to the one or more inputs to the control scheme.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 28 illustrates an exemplary dosing table with governed flow rates;

Figure 1:
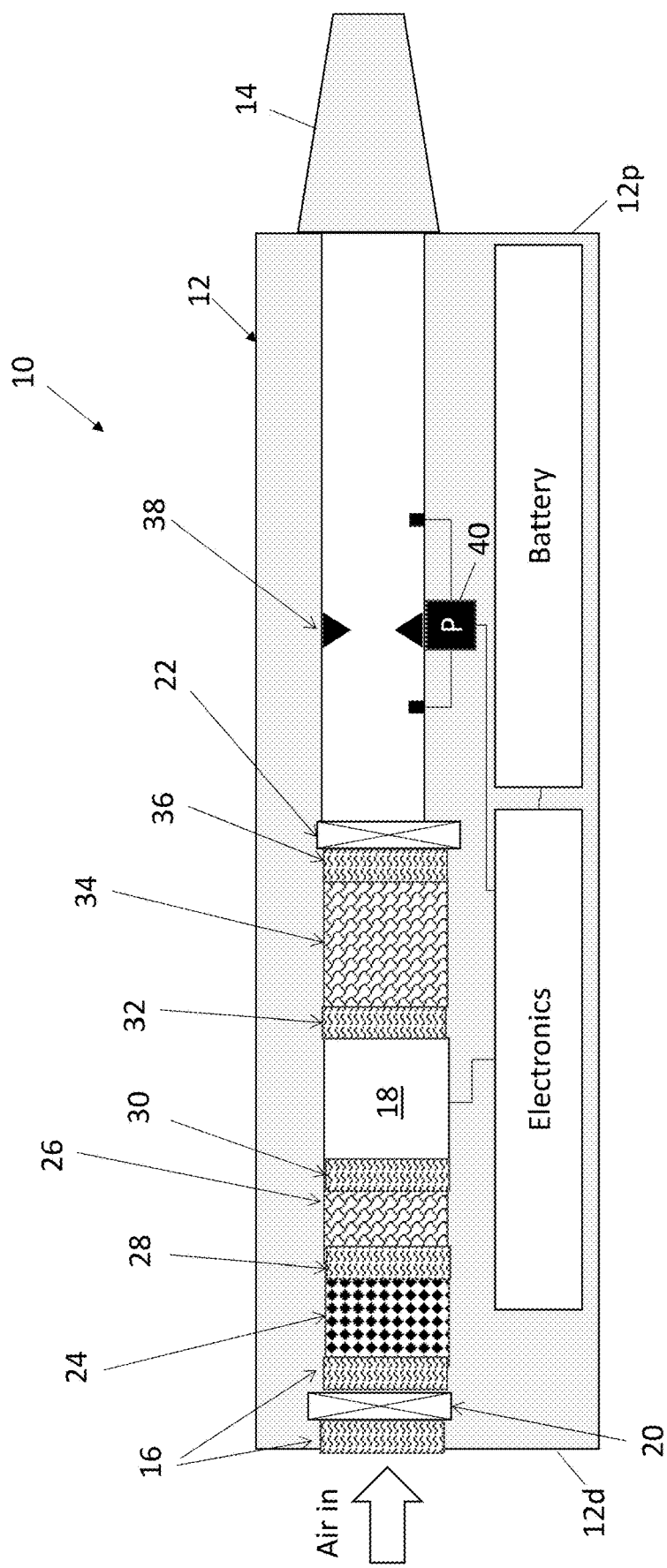
FIG. 1 illustrates an exemplary embodiment of a fully integrated electric NO inhaler system block diagram.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to systems and methods of delivering nitric oxide (NO) using an inhaler device. A NO inhaler can be designed to dose a number of discrete breaths. NO inhalers can source their NO from an onboard gas cannister or generate the NO themselves. Various approaches to NO can be utilized, including but not limited to electrical discharge generation, microwave generation, derivation from N2O4, NO donor molecules, and photochemically generated NO. The ideas presented herein apply to both NO generation and compressed gas delivery systems.

A NO inhaler device can be used in a variety of settings. In some embodiments, a NO inhaler device can be used by a patient in a home setting. In some embodiments, the inhaler device can be individually packaged and kept in an ambulance to be used on a patient during ambulance transport to improve O2 saturation. Once the patient arrives at the hospital, the inhaler could be disposed of and the patient can be transferred to a hospital-based NO source.

Nitric oxide is a pulmonary vasodilator that can decrease pulmonary vascular tension, improve cardiac output, and increase patient oxygenation. It can be delivered alone or in combination with other drugs. In some applications, NO is used to enhance the uptake and/or effect of another drug.

The following are examples of various inhaler device elements that can be included in the device and will be described in more detail below, including but not limited to disposable elements that include NO2 scrubbing, filter, mouthpiece, and other components, one or more flow sensors, a compressed NO device that permits gas to warm before delivery to user, one or more mixing elements downstream of NO generation/injection, dehumidification capability, VOC removal capability, one-way valves to keep the internals clean and prevent exhaled gas from entering the device, inspiratory flow control (passive with critical orifice, active with active valve control), a treatment controller, and/or mass flow measurement of inspired air.

In some embodiments, a NO inhaler device can include features for inhalation assistance Examples include but are not limited to user assists inhalation using muscles other than respiratory muscles to generate inspiratory flow pressure (e.g., squeezing or otherwise activating a pistol grip or other trigger to push gas for inhalation), user assists inhalation using their body weight to generate inspiratory flow pressure, and bypass channel to reduce inhalation flow restriction.

Exemplary triggering conditions for delivery of one or more drugs from an inhaler device include multi-factor triggering, a requirement for a disposable portion of the device to be inserted in order to dose, and a requirement for a user to be present in order to dose (for example, IR sensor that detects a user's mouth).

The following are dose delivery examples which will be described in more detail below: limiting inspiratory flow rate to a level that can be dosed by the NO supply/generator for example using a critical orifice or using active flow restriction control, initiating NO delivery when the inspiratory flow rate reaches a threshold flow rate, ending NO delivery when inspiratory flow rate falls below a threshold flow rate, delivering of a NO pulse delayed after inhalation detection, NO delivery/generation proportional to inhalation flow rate, NO delivery ends before the end of inspiration so that the final gas volume of inhalation purges the system with air, control and delivery of an additional drug(s), and delivering NO to various portions of the breath (e.g., beginning/middle/end).

Dose control examples include but are not limited to the ability for a device to lock out dosing if user is exceeding the permitted dose rate, and the ability for the device to remind a user when it is time for the next dose.

Exemplary system features include but are not limited to customizing the dose level, pulse profile and pulse timing at least in part based on a user clinical condition, exhalation analysis, enhanced performance of concomitant therapies, and having a user interface, all of which will be discussed in more detail below.

Electric No Generation

FIG. 1 depicts an exemplary embodiment of an inhaler 10 with a built-in NO generator. The device includes an enclosure 12 that protects the internal components from fluid ingress, particulate ingress, electrostatic shock and/or impacts. The enclosure 12 also protects the user from high voltage within the device. The user inserts a mouthpiece 14 located at a proximal end 12p of the enclosure 12 into their mouth, seals their lips around the mouthpiece 14 and inhales, drawing room air through the device. Air enters a distal end 12d of the enclosure 12 through an air inlet and passes through an optional particle filter 16. Most embodiments have at least one particle filter between the air inlet and a plasma chamber 18 to protect the plasma chamber from contamination and minimize the variety of chemical reactions that could occur there. Each particle filter location presented here is optional but has certain merits. The first particle filter protects the one-way valve to ensure that the valve will continue to seal correctly.

In some embodiments, optional one-way valves 20, 22 (e.g., flapper, duckbill, check) before and/or after the NO generation section can be used to protect the internals from particulate as well as environmental humidity which can accelerate the exhaustion of desiccant and scrubber materials when used. After passing through an optional first check valve, the air passes through an optional desiccant stage 24 that removes some or all of the water content. Water removal can decrease corrosion of electrodes, improve the accuracy and repeatability of NO generation, and minimize the variety of compounds that can be created from an air plasma. Examples of desiccant materials for this application include but are not limited to silica and a molecular sieve.

In some embodiments, a pre-scrubbing stage 26 of the device is also optional. When used, this stage removes VOCs from the incoming air that could still remain after the desiccant stage (molecular sieve material when used can eliminate some VOCs in addition to water). In addition to VOCs, the pre-scrubber stage may remove the atmospheric CO2 in the air (e.g., when soda lime is used). The desiccant stage may be flanked by one or more particle filters to prevent migration of the desiccant material. Similarly, the scrubbing stage may be flanked by optional particle filters 28, 30 for the same purpose. A pre-scrubber stage may also use activated carbon to remove VOCs and nitrogen oxides.

After passing through the preconditioning portion of the gas pathway, reactant gas enters the plasma chamber 18 where N2 and O2 within the air are ionized to form NO and NO2 in a balance of air. In some embodiments, ionization is via a DC arc passing between two or more electrodes. In some embodiments, ionization is via an AC arc passing between two or more electrodes. In some embodiments, ionization is via a plasma formed by microwave radiation. In some embodiments, ionization is via focused lasers.

It is noteworthy that most electrically-generated NO systems require a faraday cage (not shown) to contain and suppress electromagnetic radiation. In some embodiments where NO is generated within the disposable cartridge, the cartridge can be wrapped in a conductive coating to act as a shield. In addition, metallic screens and/or tortuous conductive pathways for the gas can be used to contain electromagnetic radiation within the system.

After generating NO and NO2 within the plasma chamber 18, the gas, now referred to as "product gas," can pass through an optional filter 32 that captures electrode particles and prevents migration of scrubber material into the plasma chamber 18. Then, the product gas passes through a scrubber 34. The scrubber 34 can be comprised of NO2 scrubbing material (e.g., soda lime, TEMPO, metal organic framework (MOF)) in the form of sheets and/or particles and/or open cell foam and/or coatings. In some embodiments, a final particle filter 36 eliminates scrubber particles and any remaining electrode particles from the gas flow. In some embodiments, a particle trap or sharp bend in the pneumatic pathway is utilized to capture particles. In some embodiments, the internal walls of the device are at least partially covered in a sticky material that captures particles.

Prior to delivery to the user, product gas flows through an orifice 38 that provides a flow restriction. This flow restriction enables a delta-pressure sensor 40 to measure flow to the user. In some embodiments, the flow measurement is used for one or more of detecting the user inspiration, determining the duration of inspiration, determining when the inspiratory flow is above a minimum threshold, integrating flow information into a volume measurement. In some embodiments, the pressure of the product gas is measured to detect inspiration. Information collected from a flow sensor can serve as an input into a NO flow/production controller to vary the quantity of NO added to the inspiratory gas in real time. Various types of flow sensors can be used including but not limited to delta pressure, hot wire anemometer, an optical sensor on a rotary flow element, or a generator on a rotary flow element. In some embodiments, the flow and/or pressure measurement is utilized to determine when the inspiratory flow has exceeded a threshold beyond which NO is added to the inspiration. A threshold of flow reduces the potential for false positives (dosing when there is no inspiration) and ensures that there is residual flow at the end of an inspiration event to clear the device of NO/NO2.

The device interfaces with the user, for example, with the mouthpiece 14. In some embodiments, the mouthpiece is an integral part of the enclosure. In some embodiments, the mouthpiece is removable for cleaning and/or replacement. In some embodiments, the device interfaces with the user with either a mask or nasal cannula.

Figure 2:
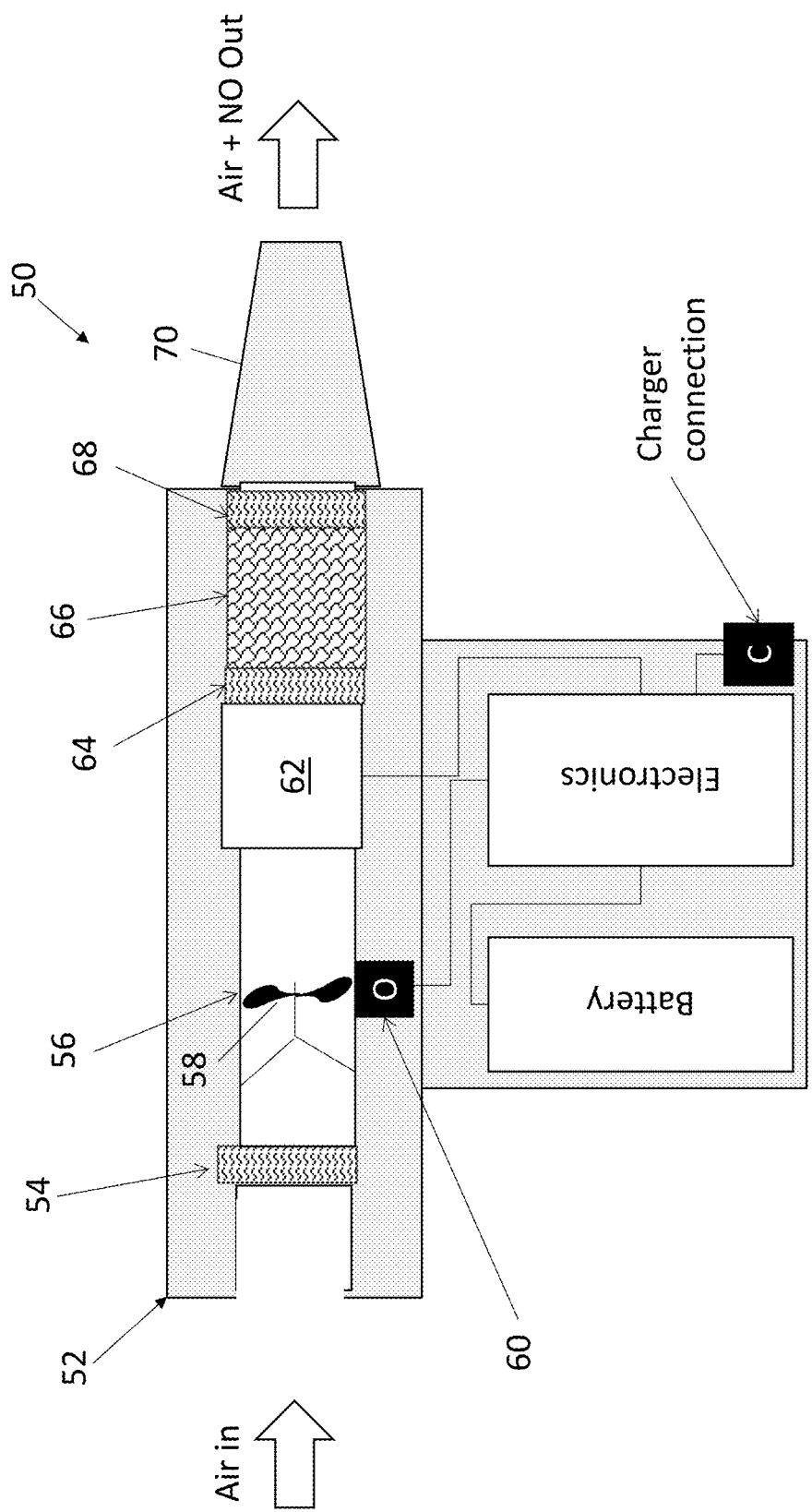
FIG. 2 illustrates an exemplary embodiment of an electric NO inhaler with pistol grip and propeller flow meter.

FIG. 2 depicts another exemplary embodiment of a NO inhaler 50 with NO generation. In the embodiment shown in FIG. 2, incoming air into an enclosure 52 is filtered by a filter 54 prior to flowing through a flow sensor, such as a rotary flow meter 56. As shown, a propeller 58 pivots with low friction. An optical sensor 60 within the enclosure 52 can detect propeller blade motion or register changes in position of an optical code on a surface of the propeller. In some embodiments, the flow sensor is a propellor spinning a generator, a pinwheel, fan or turbine with an optical encoder, a hot wire, delta-pressure across a flow restriction, or other means of gas flow measurement. In some embodiments, only pressure is measured within the gas flow path to detect gas flow. Pressure information can be utilized to detect binary flow information (yes/no) or quantitative flow rate measurements when the flow/pressure relationship of the device has been characterized. In some embodiments, the controller measures the pressure and looks up the pressure value in a look-up table to determine the flow rate. In some embodiments, the ambient pressure or no-flow pressure, temperature and humidity level are also measured by the controller to determine an air density. The air density and pressure within the air flow channel are utilized by the controller in a 2-D look-up table or equation to determine the corresponding mass flow rate of air.

Based on the measured or inferred inspiratory mass flow rate, the controller determines the quantity of NO to be added to the inspiratory flow stream. The quantity of NO to be added can be based on a prescribed amount of NO to be administered, or an amount requested by a user based on a user setting. In some embodiments, in real time, the controller calculates the target inspired production level of NO as the product of the instantaneous inspiratory flow rate and the desired inspired NO concentration (e.g. units of ppm·slpm, ulpm NO, or equivalent). Given that all of the inspired NO comes from the NO source/generator, the NO production from the NO source/generator must match the inspired NO production level. For example, if the instantaneous inspiratory flow rate is 10 lpm and the target inhaled concentration is 400 ppm NO, then the instantaneous NO production level required is 4000 ppm·lpm. The controller looks up the plasma chamber settings (e.g. electrical discharge frequency, electrical discharge duty cycle, discharge current, etc.) to generate the target production level in the available reactant gas flow rate based on a chart like the one depicted in FIG. 3.

Figure 3:
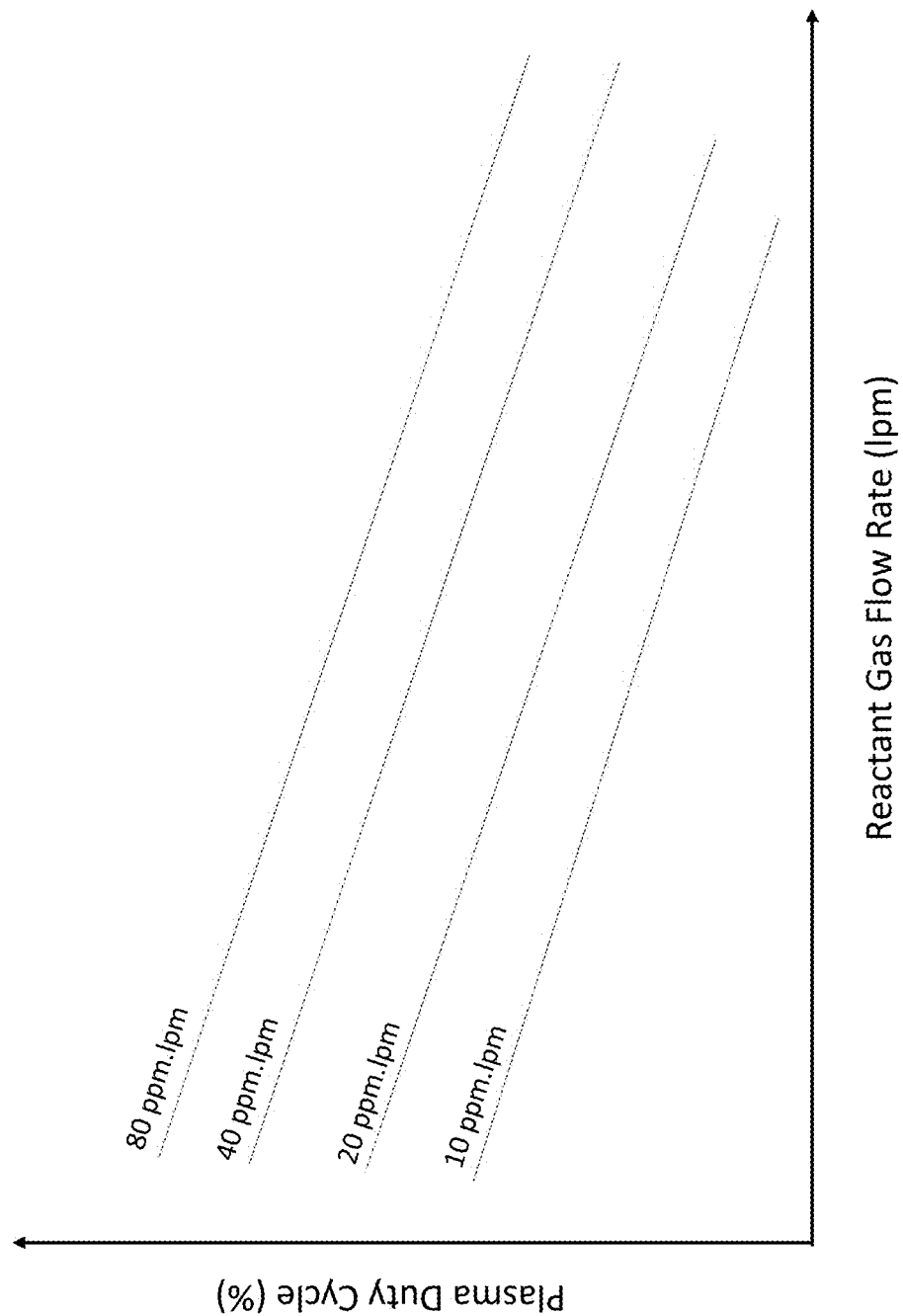
FIG. 3 depicts an exemplary graph showing the relationship between reactant gas flow, target NO production and required plasma parameters.

FIG. 3 depicts an exemplary graph showing the relationship between reactant gas flow, target NO production and required plasma parameter(s), duty cycle in this case. For one or more measurements of the inspiratory flow rate, the controller reads the corresponding NO production level required and then reads the appropriate duty cycle on the Y axis. In some embodiments, the controller interpolates between two curves to more accurately derive the target duty cycle.

Figure 4:
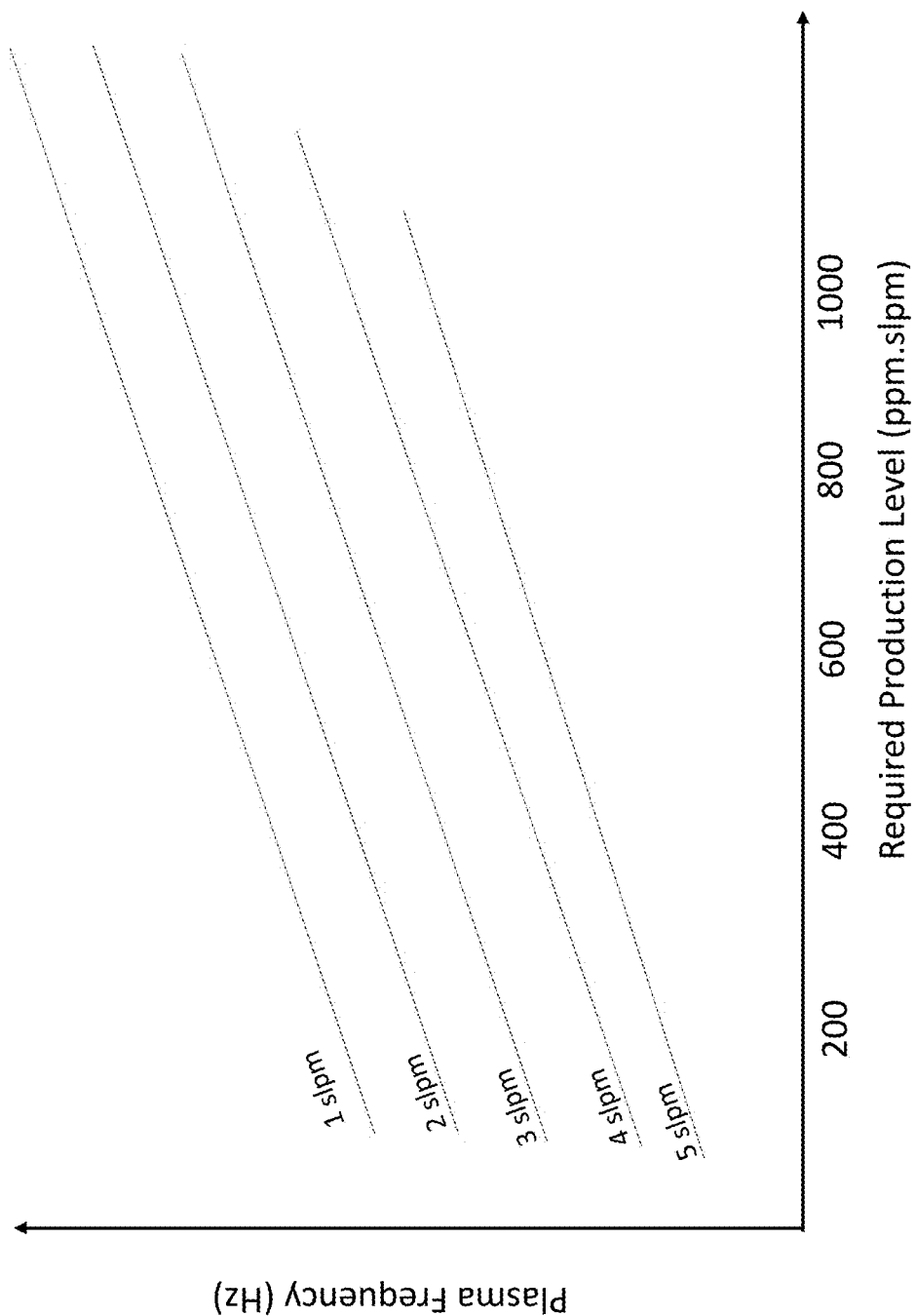
FIG. 4 depicts an exemplary graph showing an approach to deriving plasma parameters for a required amount of NO production.

FIG. 4 depicts another exemplary graph showing an approach to deriving plasma parameters for a required amount of NO production. The controller determines the required production level based on the inhaled gas flow rate and the target inhaled NO concentration. The controller determines the required plasma parameters(s), in this case electrical discharge frequency, based on the current flow rate through the plasma chamber. This same information can be captured in a look up table or one or more mathematical equations.

The controller may make additional adjustments to the plasma parameters based on the ambient pressure, ambient temperature, ambient humidity, scrubber type, scrubber age, electrode age, and other variables.

As shown in FIG. 2, the filtered reactant gas passes through a plasma chamber 62 to form NO. Then, the product gas is filtered, scrubbed and filtered a second time by an optional filter 64, a scrubber 66, and a filter 68 prior to traveling through a mouthpiece 70 to the user. The device is battery powered and includes an external connection (e.g., USB) for charging. The electronics may be only hardware or be controlled by a microprocessor running firmware.

In some embodiments, the entire device, such as those shown in FIG. 1 and FIG. 2, is disposable. Disposable versions are designed for inexpensive assembly with minimal materials. In some embodiments, the battery is rechargeable and in other cases, it is not. The components that determine the service life of a disposable NO generator can be the battery life, the scrubber life, the electrode life and/or the filter life. In some instances, the device stops functioning at the end of life, requiring the user to start using a replacement device.

Figure 5:
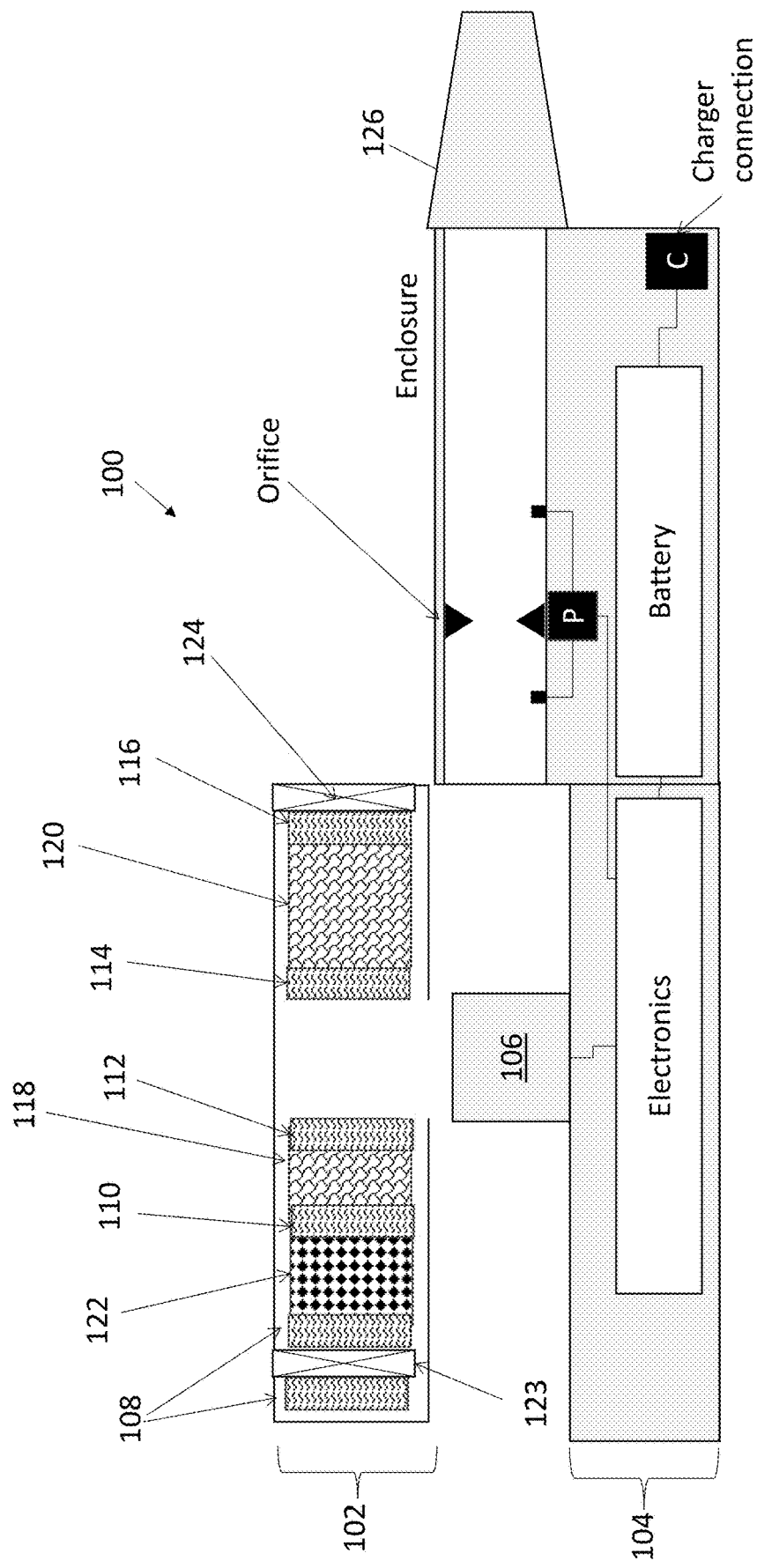
FIG. 5 illustrates an exemplary embodiment of an electric NO device with a replaceable filter/scrubber/desiccant cartridge.

FIG. 5 depicts an exemplary embodiment of an inhaler device 100 where a portion of the device is disposable, and a portion is reusable. In the embodiment depicted, the disposable portion 102 connects to the top of the reusable portion 104, sliding over a plasma chamber 106 during assembly. The disposable portion 102 includes elements that can become exhausted or clogged over time. The disposable portion 102 can include one or more of the following elements: filters 108, 110, 112, 114, 116, a pre-scrubber 118, a scrubber 120, desiccant 122, optional one-way valve 123, one-way valve 124, and a mouthpiece 126. In the depicted embodiment, the plasma chamber 106 and electrode generators therein are part of the reusable component. When the disposable portion is connected to the reusable portion, a gas-tight connection is established so that ensures that air that the user draws in only comes from the inlet of the device. In some embodiments, the plasma chamber includes electrodes (e.g., gliding arc, parallel opposed, opposed, etc.). In some embodiments, the plasma chamber consists of a microwave cavity.

In some embodiments, the plasma chamber is part of the reusable component. In some embodiments, the plasma chamber is part of the disposable component. The plasma generation elements (e.g., electrodes, antennas, stubs, etc.) can be part of either the disposable or the reusable portion of the device. In some embodiments, a first generation element is part of the disposable and a second generation element is part of the reusable portion of the system. The location of the reusable portion location depends, in part, on generation element longevity, cost, and packaging efficiency. For example, in a DC plasma system, the electrode that wears more rapidly is part of the disposable and the other electrode is part of the reusable portion, in some embodiments.

In an electrode-based system, placing the electrodes in the disposable can allow for more consistent device performance and the ability to use less expensive, shorter-lasting electrode materials (e.g., tungsten, stainless steel, copper).

Depending on the design, one or more high voltage electrical connections is used to deliver the voltage to the disposable plasma generation elements. Other designs utilize a plasma vortex design where there is a central electrode and a ring-shaped electrode. In some embodiments, brushes are used. In some embodiments, ball-spring connections are used. In some embodiments, pogo pins are used.

Figure 6A:
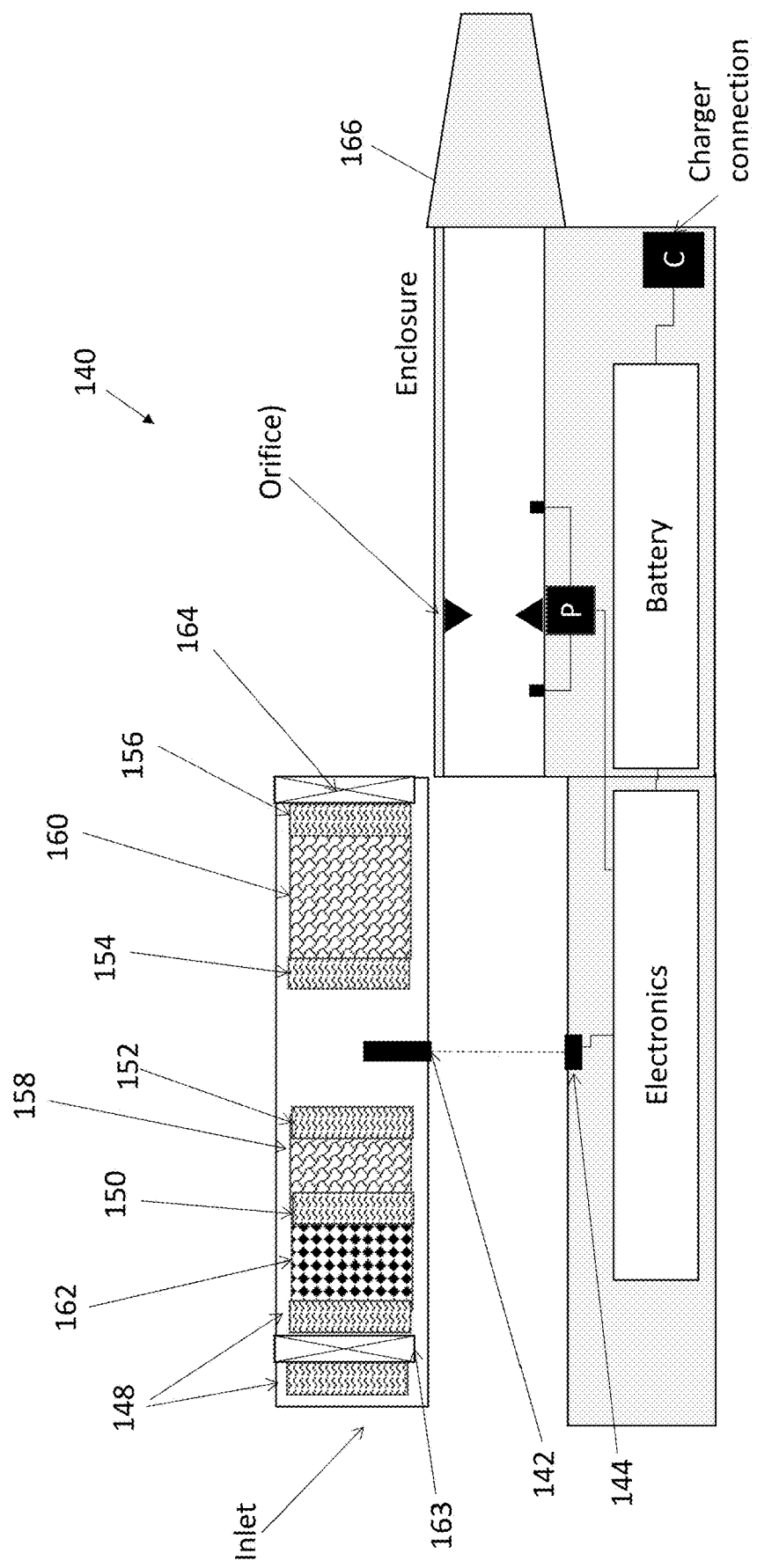
FIG. 6A illustrates an exemplary embodiment of an electric NO device with replaceable gas conditioning and electrodes cartridge.

FIG. 6A depicts an embodiment of an inhaler device 140 with a disposable component that includes a plasma chamber with two or more electrodes 142. Similar to the embodiment described above, the disposable portion can also include one or more of the following elements: filters 148, 150, 152, 154, 156, a pre-scrubber 158, a scrubber 160, desiccant 162, one-way valves 163, 164, and a mouthpiece 166. The reusable portion of the device makes electrical contact with the electrodes or with a corresponding electrical connector, such as a high voltage connector 144.

Figure 6B:
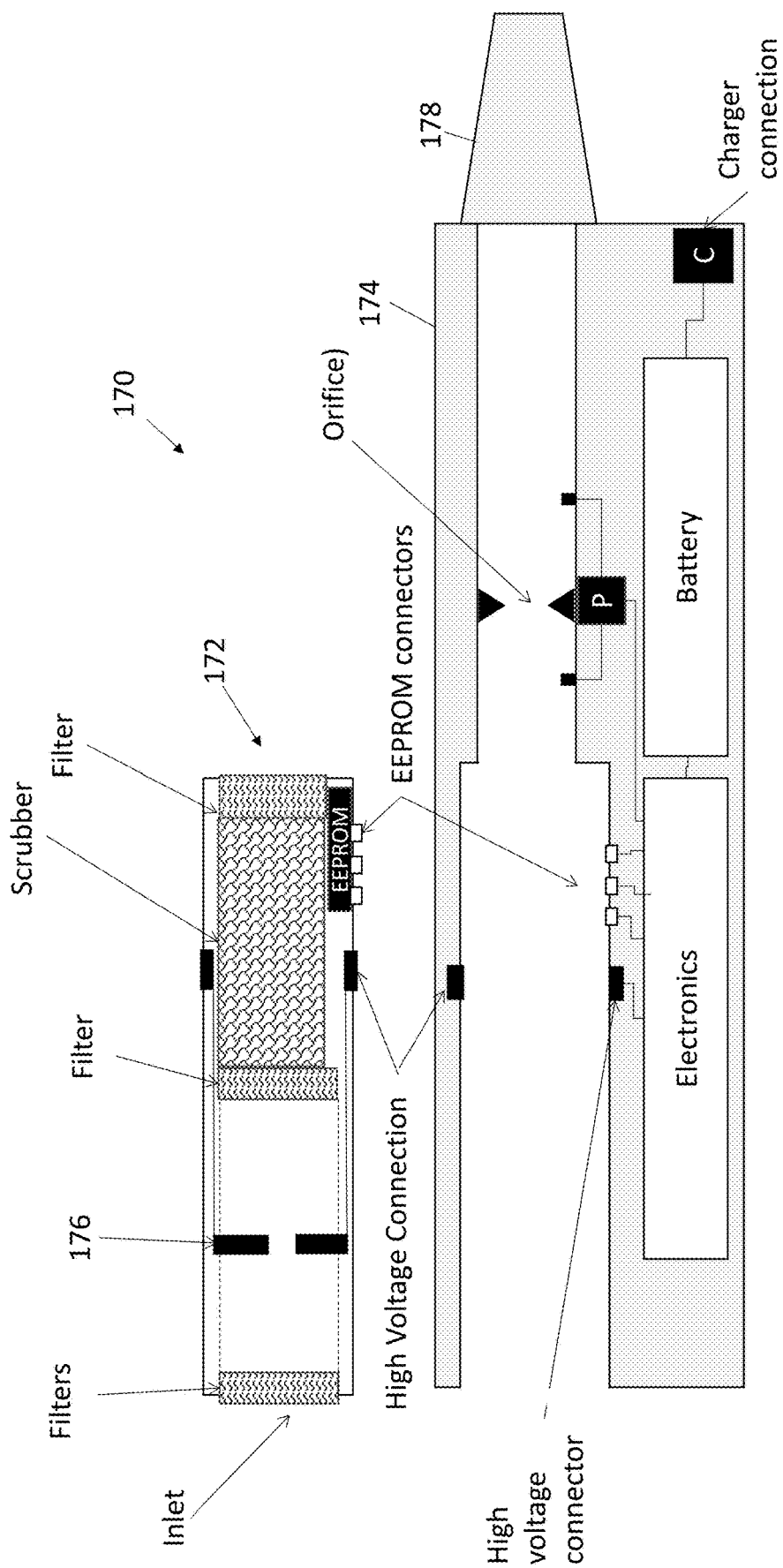
FIG. 6B illustrates an exemplary embodiment of an electric NO device with replaceable cartridge including electrodes, scrubber, filters and memory device.

FIG. 6B depicts an embodiment of an inhaler device 170 electric NO generator with replaceable electrode and scrubber cartridge 172. The cartridge 172 is inserted into a distal end of an enclosure 174. When fully inserted, electrical connections register for electrodes 176 and a memory device. The device electronics can determine that there is a cartridge, and it is fully inserted when the memory device connections have been established. In this design, the electrodes are at a different location than the electrical connectors along the length of the disposable cartridge. This is to locate the electrical connectors deeper within the device, to prevent a user access and possible creepage from the high voltage connectors to the user. In some embodiments, the outer surface of the disposable has grooves, undulations and/or other features that lengthen the electrical creepage distance from the high voltage electrical connectors to the user.

The cartridge 172 and/or mouthpiece 178 can be retained within the inhaler enclosure 174 in any number of ways, including but not limited to detents, threads, a bayonet fitting, a taper with interference, latches, and friction. In some embodiments, an O-ring and/or lip seal is utilized at the interface between removable components to prevent loss of NO and/or sourcing air from uncontrolled locations (leaks into the system as the user draws air in).

Figure 7:
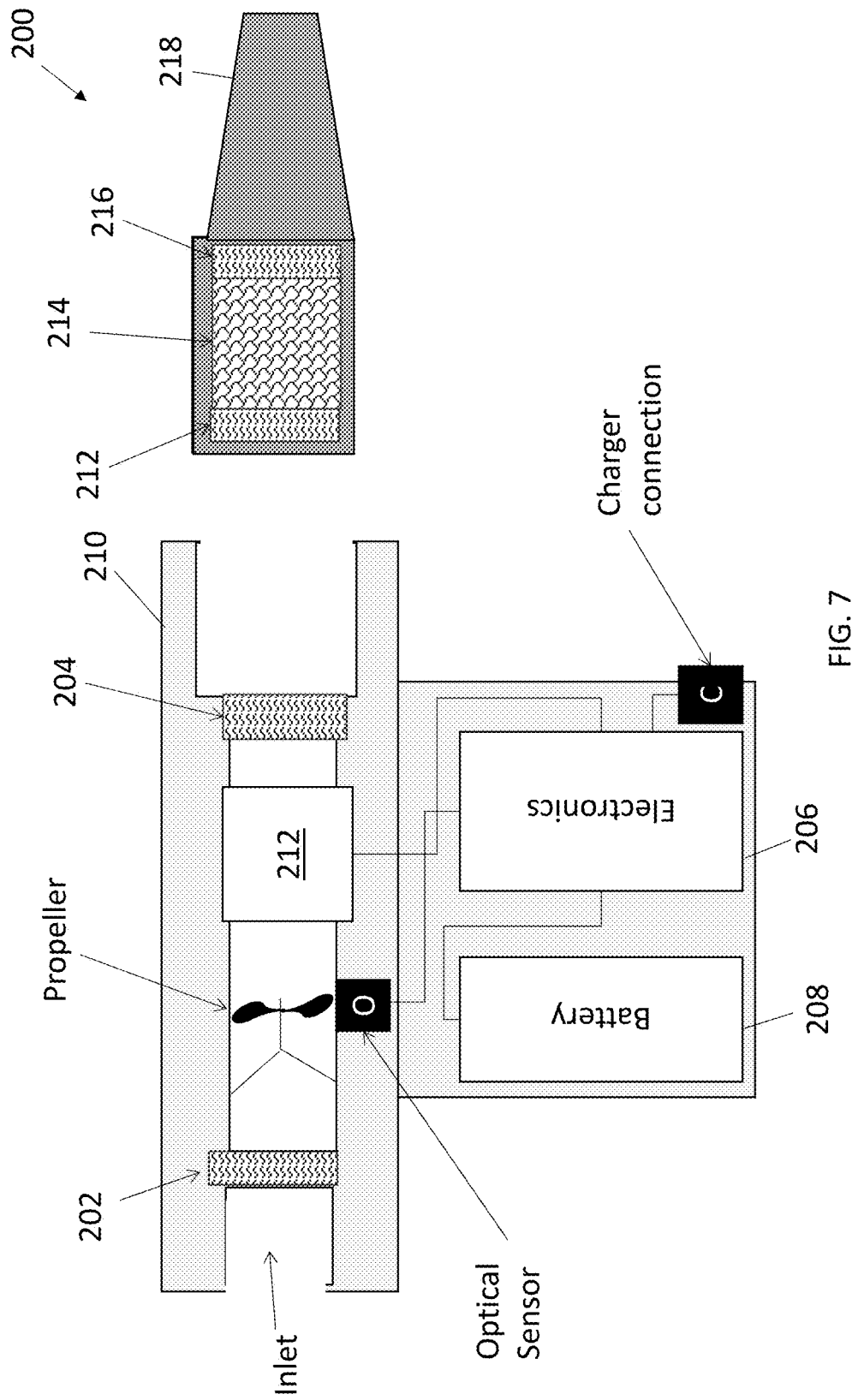
FIG. 7 illustrates an exemplary embodiment of an electric NO device with replaceable gas scrubber, filter and mouthpiece.

FIG. 7 depicts another exemplary embodiment of an NO inhaler device 200. A reusable portion of the device can include an inlet filter 202, a flow sensor, a plasma sensor, an outlet filter 204, electronics 206 and a battery 208 housed within an enclosure 210. The filters before and after a plasma chamber 212 protect the chamber from particulate which could reduce creepage distances and contaminate the generated NO. The enclosure is shaped to have a pistol-grip for ergonomics. The disposable component includes a filter 212, a scrubber 214, a second filter 216, and a mouthpiece 218 held together with a housing. The disposable component inserts into the proximal end of the reusable component. In some embodiments, the reusable component can detect the presence/absence of the disposable component and only permit treatment when a disposable is present.

The presence of the disposable component can be detected in any number of ways including electrically, optically, magnetically, or physically (e.g., button pressed by a disposable component upon insertion). In some embodiments, the disposable component includes an RFID chip that is detected by the reusable component. In some embodiments, a memory chip within the disposable component makes electrical contact with the reusable component. In some embodiments, a bar code on the disposable device is optically read by the reusable component. In some embodiments, the force of insertion and/or latching of the disposable component is detected by the reusable component and interpreted as disposable insertion.

In some embodiments, an inhaler device can limit the amount of NO that goes through the scrubber before requiring scrubber replacement. In some embodiments, the controller within the device tracks the amount of NO generated based on the duration of NO production and production level. In some embodiments, the device can also prompt scrubber replacement based on the amount of time that the scrubber has been inserted and the expiration date of the scrubber. In some embodiments, the device can also confirm the validity and expiration date of a scrubber before use.

Figure 8:
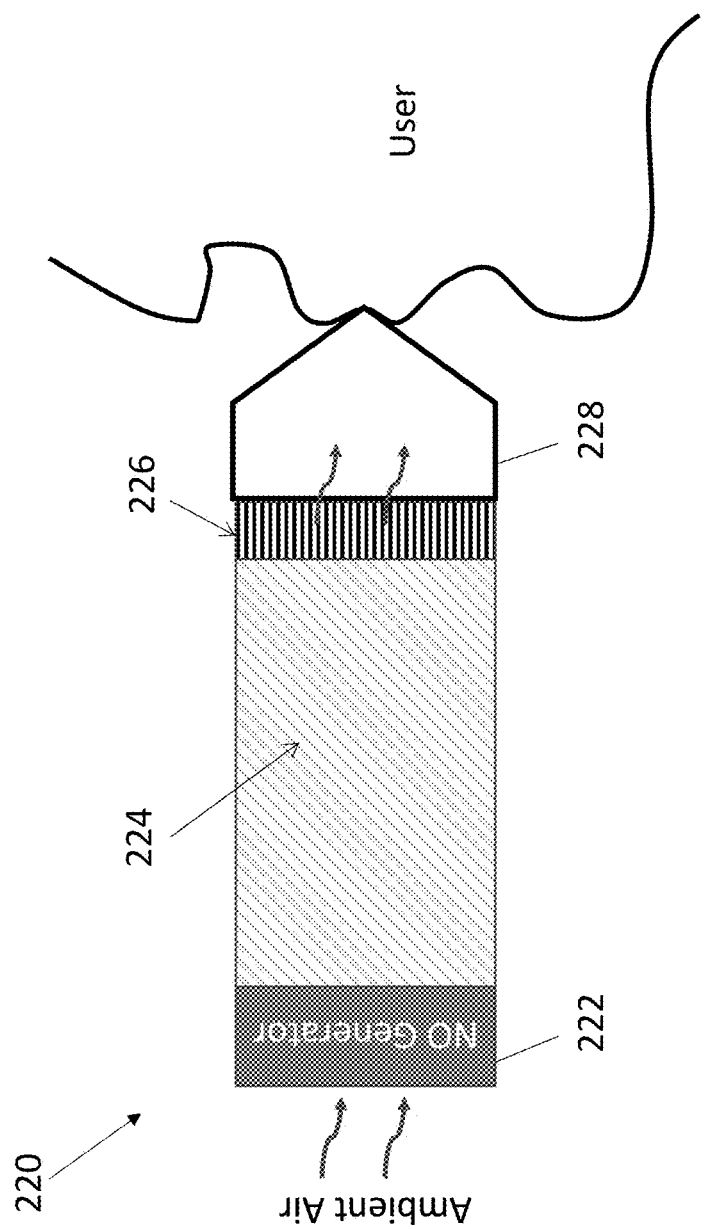
FIG. 8 illustrates an exemplary embodiment of NO generation and scrubbing device.

FIG. 8 depicts an embodiment of a standalone NO delivery system 220 in the form of an inhaler device, that includes an NO generation device 222, a scrubber 224, and an optional filter 226. The presence or absence of a final filter in the gas stream can be a design decision based at least in part on the potential for particulate in the gas stream, as well as the potential quantity of particulate, size distribution of particulate, toxicity of the particulate and overall risk to the patient from particulate. The system is shown delivering NO through a mouthpiece 228, however the same system can interface with the user with a face mask or nasal mask. In some applications, the user inhales slowly through the device over a period of 5 to 10 seconds while the system doses the gas flow with sufficient NO for a specific clinical indication. The system can be used as rescue therapy during exacerbations, high altitude sickness, panic attacks, or other conditions causing short term troubled breathing. In some embodiments, the system is completely disposable. In some embodiments, the system has a reusable component that is rechargeable or accepts replacement batteries. In some embodiments, the scrubbing element(s) and/or filter(s) are disposable.

Figure 9:
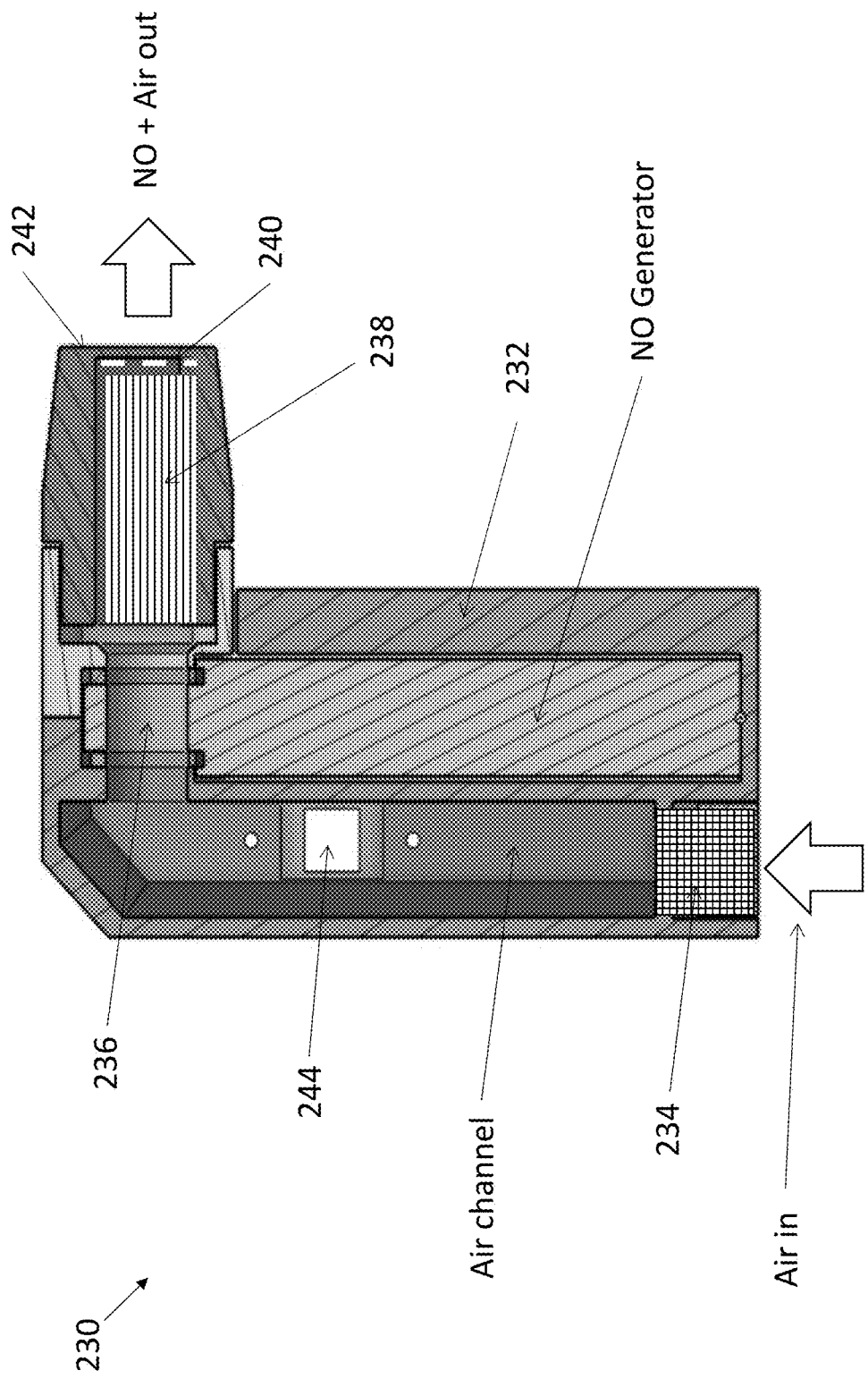
FIG. 9 depicts an exemplary embodiment of a pistol-grip NO inhaler device configuration.

FIG. 9 depicts another embodiment of a NO delivery device 230 with a pistol grip. Air enters the device through the bottom of the handle enclosure 232 and flows through a particle filter and scrubber 234 for VOC and particulate filtration. After traveling up through the handle, the air pathway turns towards the user and passes through the NO zone 236. Depending on the source of NO, the NO zone can include high voltage electrodes, microwave antennas, solid material that releases NO from photochemistry, and other methods. The NO generation/release is controlled by the NO generator in the handle. NO+Air passes through gas conditioning elements, such as a scrubber 238 and a particulate filter 240 in a removable mouthpiece 242 before being delivered to the user. An activation switch 244 on the handle is depressed by the user to activate the device.

Figure 10A:
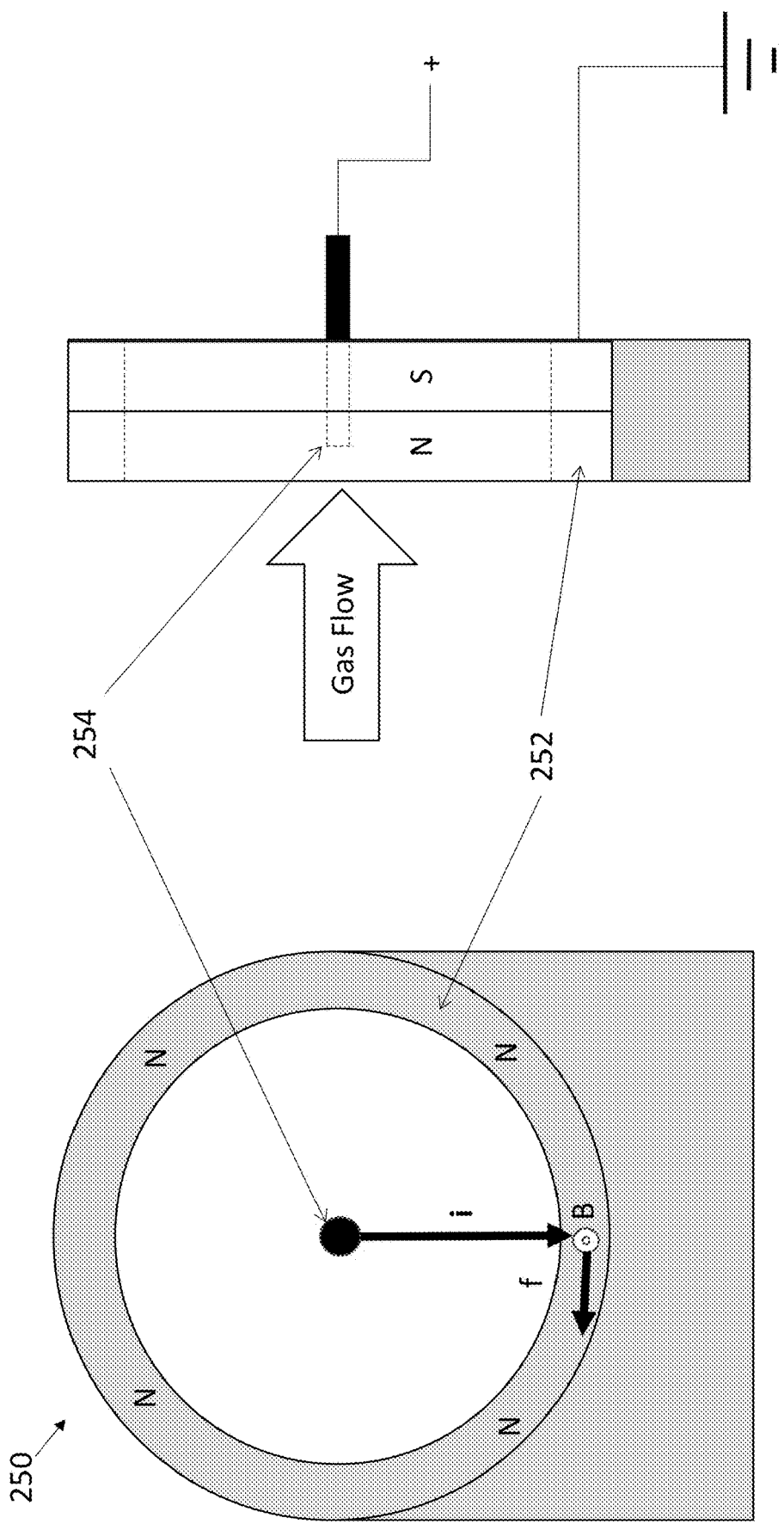
FIG. 10A depicts an embodiment of a plasma NO generation device that utilizes a plasma vortex.

As explained above, a plasma chamber can generator NO in a variety of ways and using a variety of types of electrodes. FIG. 10A depicts an embodiment of a plasma NO generation device 250 that utilizes a plasma vortex caused by Lorentz force on current in a magnetic field. In this design, a concentric set of electrodes consists of a magnetic ring 252 and a center electrode 254. The center electrode is positive, and the ring is ground. Current is conducted through a plasma that forms when breakdown occurs in the annular space. The direction of the current is shown by the vector "i." The top surface of the magnet is the north pole (magnetic "B" field shown coming out of the plane of the page). The force on the plasma is given by the Lorentz force using the "right hand rule", f~(i⁻×B⁻), and is in the direction of the vector "f". The result is a clockwise-rotating plasma discharge around the ring. If the polarity of the applied voltage is reversed, the arc will travel the opposite direction around the annular space (counter-clockwise).

When reactant gas is passed through the plasma vortex, NO is generated by the disassociation of N2 and O2 molecules from the intense heat and energy. The arc travels around the ring many times per second, treating the entire cross-section of gas flow. This effect can improve gas distribution within the product gas and overall device power efficiency. In some embodiments, the arc travels continuously around the ring for the duration of a treatment. In some embodiments, the arc is pulsed, breaking down at random points around the ring and terminating with the controller terminates the electrical discharge. The speed that the arc travels around the ring is related to the current level (i), the magnetic field strength (B) and the ring diameter (r) with larger radii requiring more time to circumnavigate.

Figure 10B:
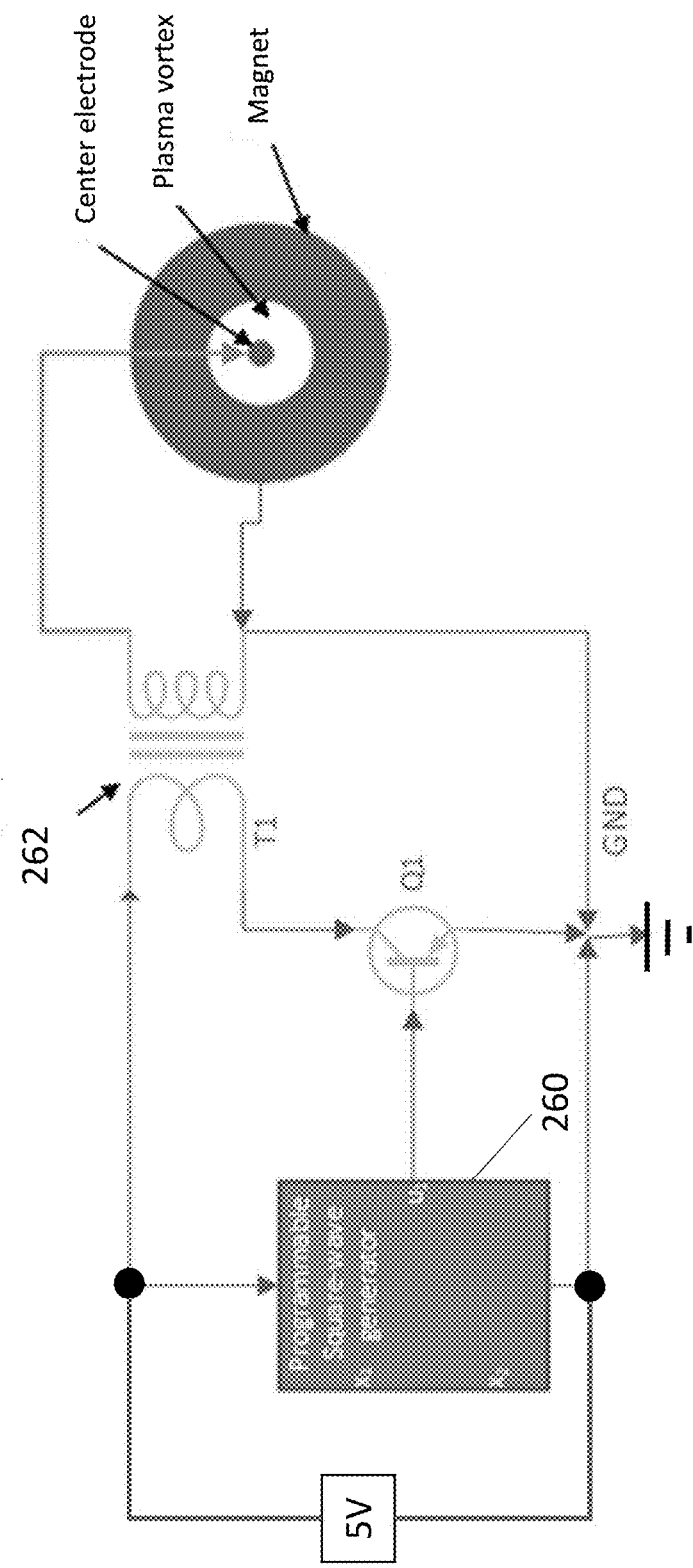
FIG. 10B depicts an exemplary power circuit for creating a plasma vortex.

FIG. 10B depicts an exemplary power circuit for creating a plasma vortex. The output of a square wave generator 260 is amplified by a transformer and passes through the primary side of a high voltage transformer 262. The secondary side of the transformer is electrically connected to the center electrode and magnet. In applications involving NO generation, the treatment controller serves as the function generator, varying one or more of the frequency, duty cycle, voltage, and current of electrical discharge pulses to vary NO production. In some embodiments, the ring is a permanent magnet. In some embodiments, the ring is an electromagnet. In some embodiments, the ring is plated with a high melting point material to decrease electrode erosion (e.g., iridium, tungsten, platinum).

Tank-Based No Delivery

Figure 11:
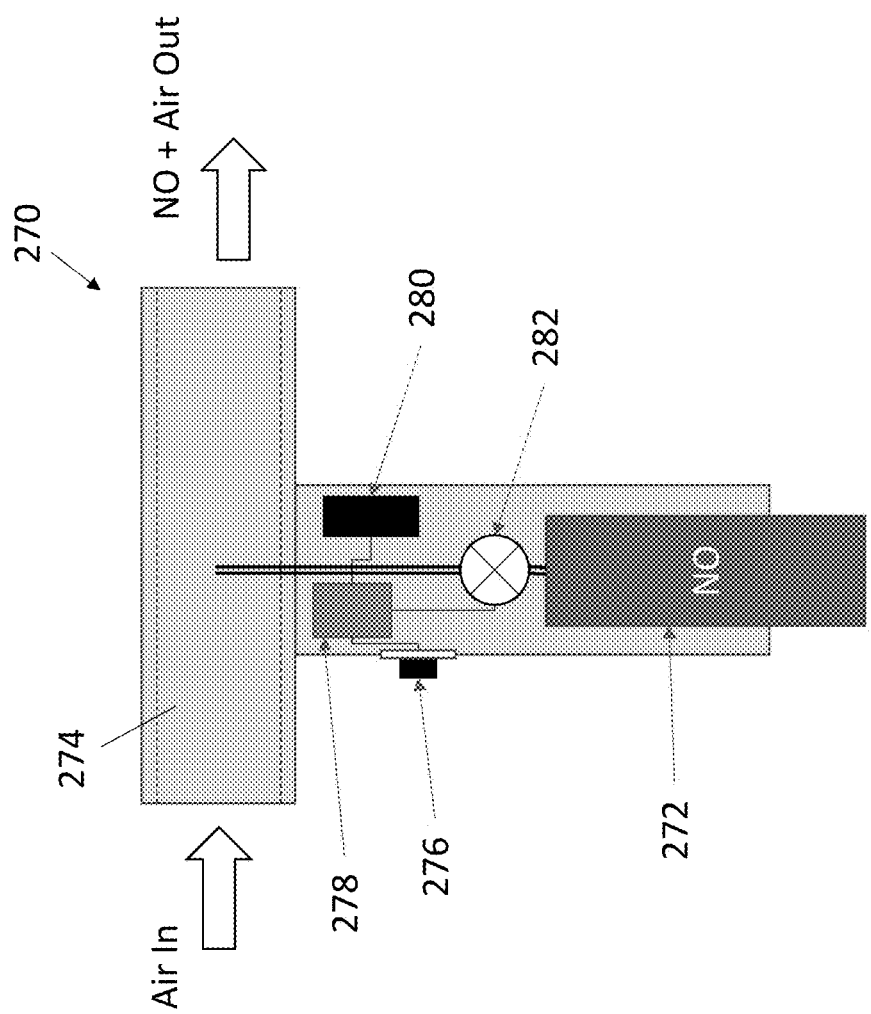
FIG. 11 illustrates an exemplary embodiment of an NO inhaler utilizing a compressed gas cylinder.

In some embodiments, the NO is sourced from a reservoir of NO. FIG. 11 depicts an embodiment of a NO inhaler device 270 that sources NO from a compressed gas cartridge or NO cannister 272. The cartridge can be filled with pure NO and/or NO diluted in another gas (e.g., nitrogen).

FIG. 11 includes an inspiratory flow path 274. A pistol grip handle includes an electrical button switch 276 that registers a user input to the dose delivery controller 278. The dose delivery controller 278 is powered by an internal battery 280 and controls a valve 282 that is in fluid communication with a pressurized NO cylinder and the inspired gas flow path. In some embodiments, the diameter of the NO flow path is sufficiently small that it restricts the flow of the NO gas. In some embodiments, a separate critical orifice component is included to govern the flow rate of NO into the inspiratory flow (not shown). In some embodiments, a pressure regulator is included to reduce the pressure of NO from cylinder pressure to a more workable pressure prior to the flow control valve (not shown). The cylinder in this embodiment is inserted into the bottom of the pistol grip and can be replaced as needed. The cylinder is retained within the device in one of a variety of ways, including using friction and/or threads.

Various levels of dose control can be added to the compressed gas delivery system. In some embodiments, the user depresses a push button to release the NO without any limits of duration of delivery. In some embodiments, the user initiates the flow of NO and the device controller limits the generation/delivery of NO to a therapeutic amount. In some embodiments, NO delivery is automatically initiated by the inhaler device when flow or pressure changes are detected in the inspiratory flow path. In some embodiments, two parameters must be sensed prior to release of NO (e.g., clamping force at the mouthpiece and flow within the inspiratory flow channel). In some embodiments, the user is detected by an infrared (IR) sensor that is oriented to detect heat from a user's mouth when the device is inserted into a user's mouth. Approaches like this decrease the potential for releasing NO pulses when the device is not in the user's mouth.

In some embodiments, the delivery system can be configured to limit the amount of NO delivered per breath. This can be done on a fixed volume basis (e.g., 10 ml NO) and/or a fixed concentration basis (e.g., NO flow equal to 10% proportion of measured inspiratory flow). In some embodiments, the NO delivery is actively controlled by the device controller (e.g., microprocessor). In some embodiments, dose control from the device is governed by electronic hardware or mechanical components. In some embodiments, a NO inhaler delivery device limits the amount of NO that can be delivered in an amount of time. For example, a NO inhaler can deny dosing if the user tries to use the inhaler to receive NO at a faster rate than prescribed or limited to. More specifically, if a device is programmed to permit 10 ml doses of 800 ppm NO for 5 breaths per hour, the device will deny treatment if a user requests a 6th dose within a 1 hour time-frame. These sort of limits may be based on safety limits of the gas being delivered but may also be based on economics to prolong the use of a cylinder. In some embodiments, a user is prescribed a NO dose rate (e.g., 6 mg/hr) and a NO inhaler device prompts the user to inhale a breath of NO periodically to maintain the target dose rate. For example, a user has been prescribed 10 breaths of 160 ppm NO per hour to treat a pulmonary infection. The device prompts the user every 6 minutes for them to receive a dose of NO. If the user is non-responsive, the device may escalate the issue by one or more of the following: using a buzzer, increasing the acoustic volume of the alarm, using a vibratory motor, alerting clinicians via a wireless link, calling the user on their phone, and other methods.

In the event that the user tries to deliver a dose of NO prior to the next scheduled delivery, some embodiments of the NO delivery and/or generation device prevent NO delivery before it is time.

It should be noted that gas can be extremely cold when released from a high-pressure cylinder, as dictated by the ideal gas law. In one embodiment of an NO inhaler device 290 depicted in FIG. 12, the delivery of NO can occur in two stages. When a button 292 is pressed, a controller 296 controls NO delivery to the user from an intermediate chamber 294 using a downstream valve 298 and NO from the high-pressure cylinder 297 is released into an intermediate chamber 294 using an upstream valve 300, where the pressure of the gas can be reduced, and the temperature of the released gas can approach ambient temperature. This intermediate chamber only contains NO and any inert dilution gas to prevent oxidation of NO between dose deliveries. In some embodiments (not shown), a pressure regulator is utilized to reduce pressure from the cylinder to the pressure within the intermediate chamber. This allows the gas pressure to be reduced in two steps, which enables finer pressure control. In some embodiments, cylinder gas passes through a warming manifold or over a warming block that warms the gas. The warming stage can be applied to pure gas exiting the cylinder, the mixed inspiratory gas, or both places.

Warming can be passive, taking advantage of the warmth of the user's body or ambient conditions. In some embodiments, battery power in the device is utilized to warm the manifold with resistive heating. Warming the gas prior to delivery can improve the comfort of the patient and prevent the potential of thermal damage to patient tissues.

In some embodiments, an exemplary sequence of events is as follows: a dose button is pressed, the downstream intermediate chamber valve is opened to release NO to the airstream, the downstream valve is closed before the intermediate chamber pressure reaches atmospheric pressure to prevent oxygen in the air from entering the intermediate chamber, the upstream valve is opened to refill the intermediate chamber, and the upstream valve is closed after a finite amount of time or after the pressure in the intermediate chamber reaches a target.

Figure 12:
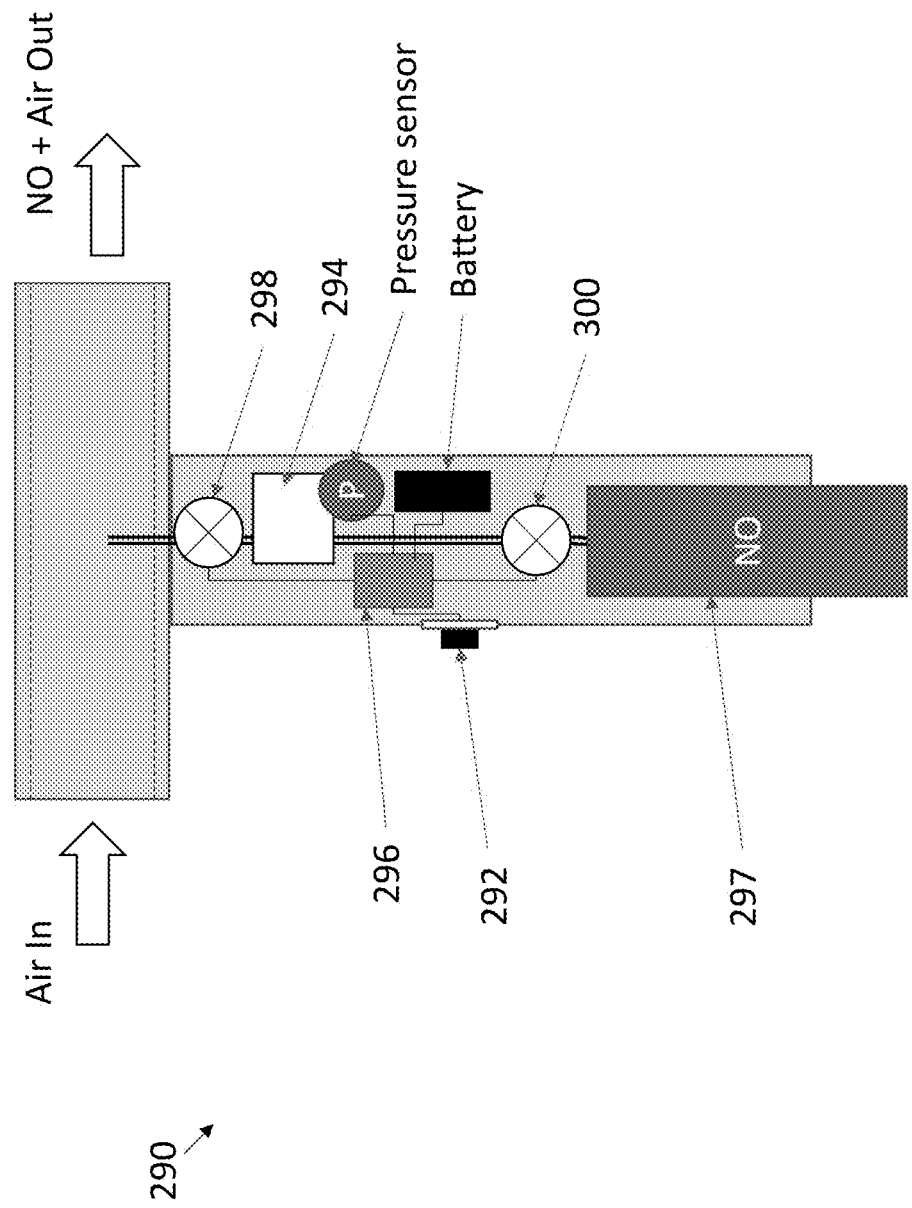
FIG. 12 illustrates an exemplary embodiment of a NO inhaler utilizing a compressed gas cylinder with intermediate chamber.

In some embodiments, a metering valve or orifice is used to slow the flow of NO gas from the high compression cylinder. Control of the valves can be done by a controller (e.g., software or electronic hardware) as shown in FIG. 12, or entirely mechanically.

Figure 13:
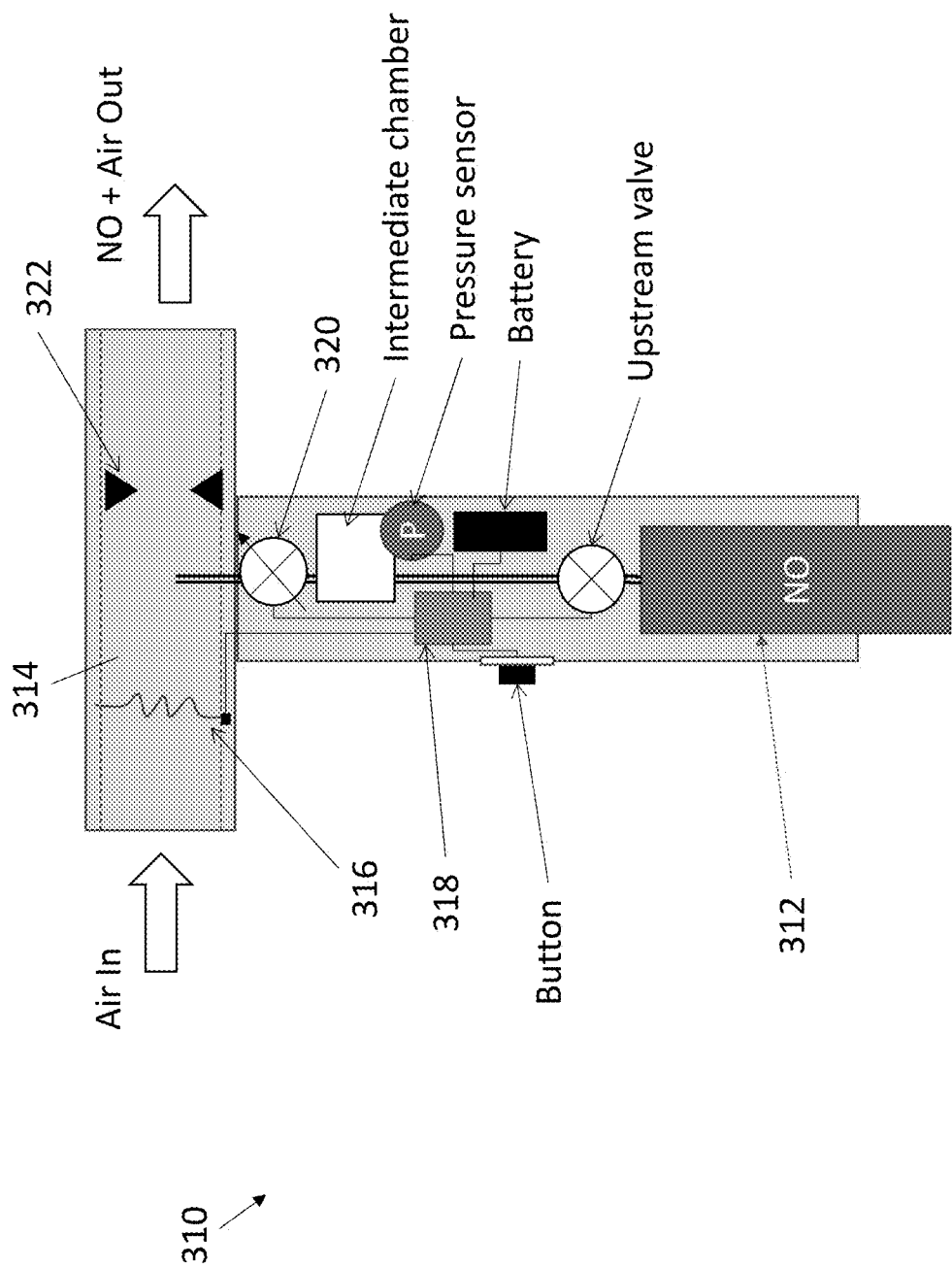
FIG. 13 illustrates an exemplary embodiment of a compressed NO inhaler with dynamic proportional NO flow control.

FIG. 13 depicts an embodiment of a NO inhaler device 310 that sources NO from a compressed gas cylinder or NO cannister 312. Inhalation draws gas through an inspiratory gas flow 314. The flow of air is measured by a flow sensor 316 that is connected to the dose controller 318. A hot wire anemometer is depicted, however other flow measurement methods could be used as well (e.g., delta-pressure across an orifice). High pressure NO is reduced in pressure and passes through a flow controller 320 that is controlled by the dose controller. In some embodiments, the flow of NO is controlled to be proportional to the inhaled air flow rate to achieve a constant concentration within the mixed inspiratory gas. A critical orifice 322 within the inspiratory air flow path limits the air flow (and combined flow) to a level that the NO supply can accurately dose.

Inspiratory Flow Control

Figure 14:
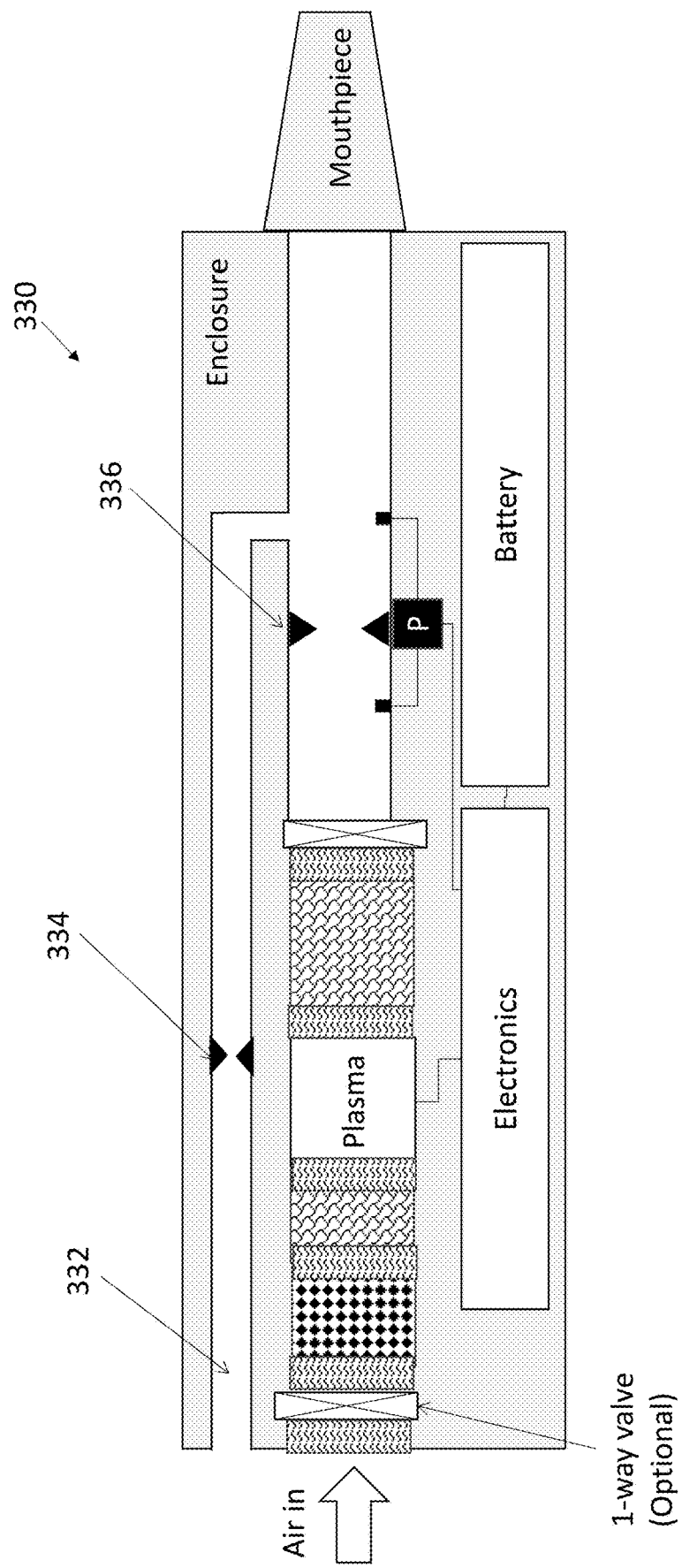
FIG. 14 illustrates an exemplary embodiment of an NO inhaler with air bypass channel.
Figure 15:
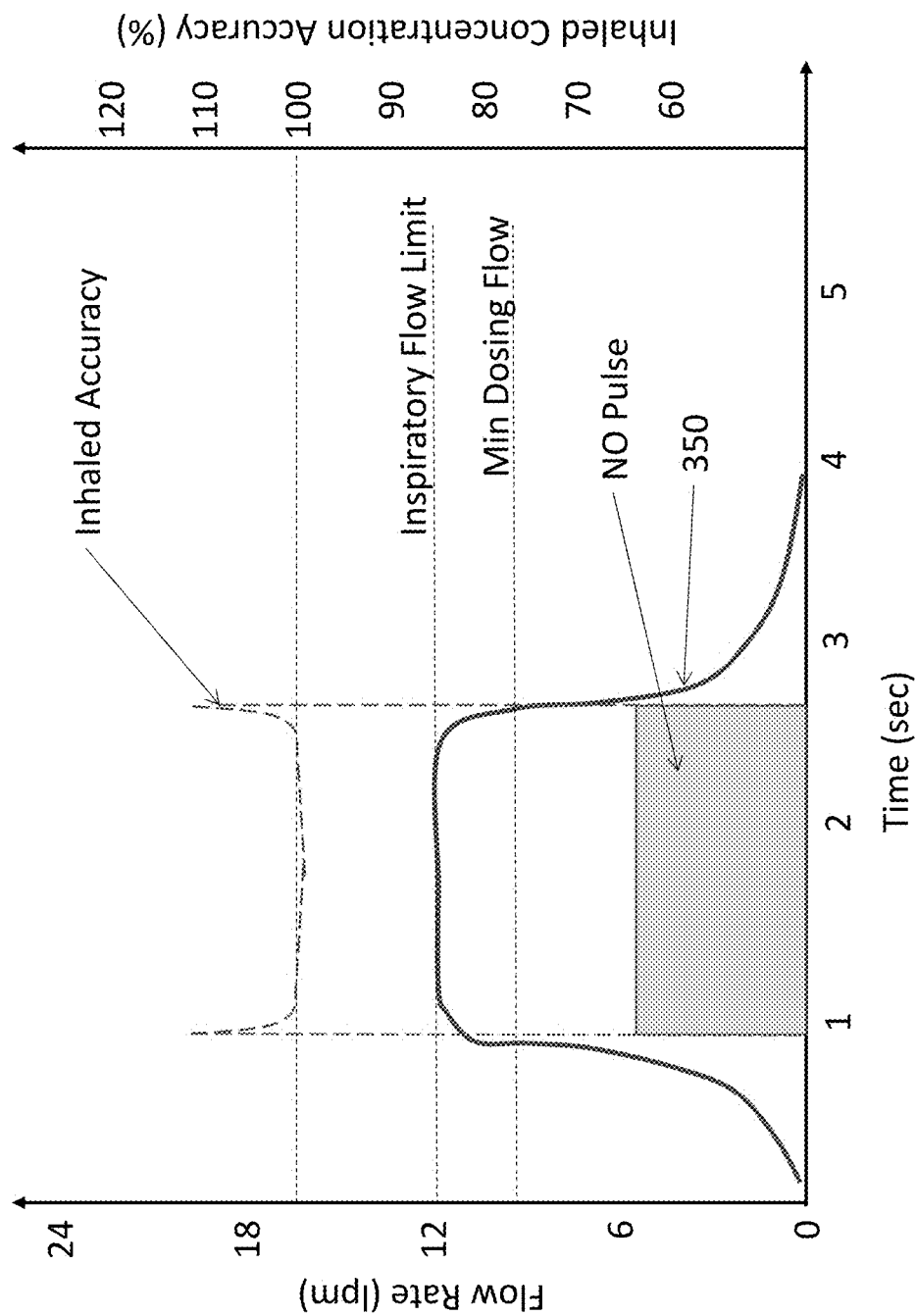
FIG. 15 illustrates an embodiment of NO flow control of a fixed flow rate NO delivery system.

In some embodiments, the inspiratory flow rate is limited by a critical orifice, as shown in FIG. 13 and FIG. 14. This enables a NO generator to dose the inspiratory flow at an accurate NO level despite NO production limitations. In some instances, the NO source can only deliver a fixed flow rate of NO and the device releases NO into the inspiratory flow when the inspiratory flow is within a target range to ensure accurate dosing. For example, a simple NO source consists of a compressed NO/N2 cylinder that releases gas through a pressure regulator. The flow rate is governed by passing through a fixed orifice and is controlled by actuating a binary valve. In some embodiments (not shown), the orifice is variable (e.g., a proportional valve, iris valve, etc.) and is controlled by the controller to vary the flow rate limit. This exemplary system contains 1000 ppm NO in the cylinder and flows the gas at a fixed rate of 1 slpm. FIG. 15 depicts an exemplary graph showing how the system can function. The inspiratory flow rate 350 begins at zero and increases. When the inspiratory flow rate, as measured by the controller, exceeds a threshold for minimum dosing flow, the controller opens the binary valve to release NO at a fixed flow rate. Since the inspiratory flow rate has not reached the inspiratory flow rate limit, there is a brief amount of overdosed inspiratory flow (10% in this example). The amount of overdosed inspiratory flow can be adjusted by varying the minimum dosed threshold. If no overdosing is acceptable, then the system waits until the inspiratory flow rate reaches the inspiratory flow rate limit prior to initiating NO gas flow. This approach of utilizing a minimum dosing flow enables a system to dose a larger portion of the inspired volume of gas while keeping the inhaled NO concentration within an acceptable range. If the NO dose had been delivered earlier in the breath depicted in FIG. 15, the level of overdose would have been higher because the 1 slpm of NO would make up a larger fraction of the inspired gas.

Figure 16:
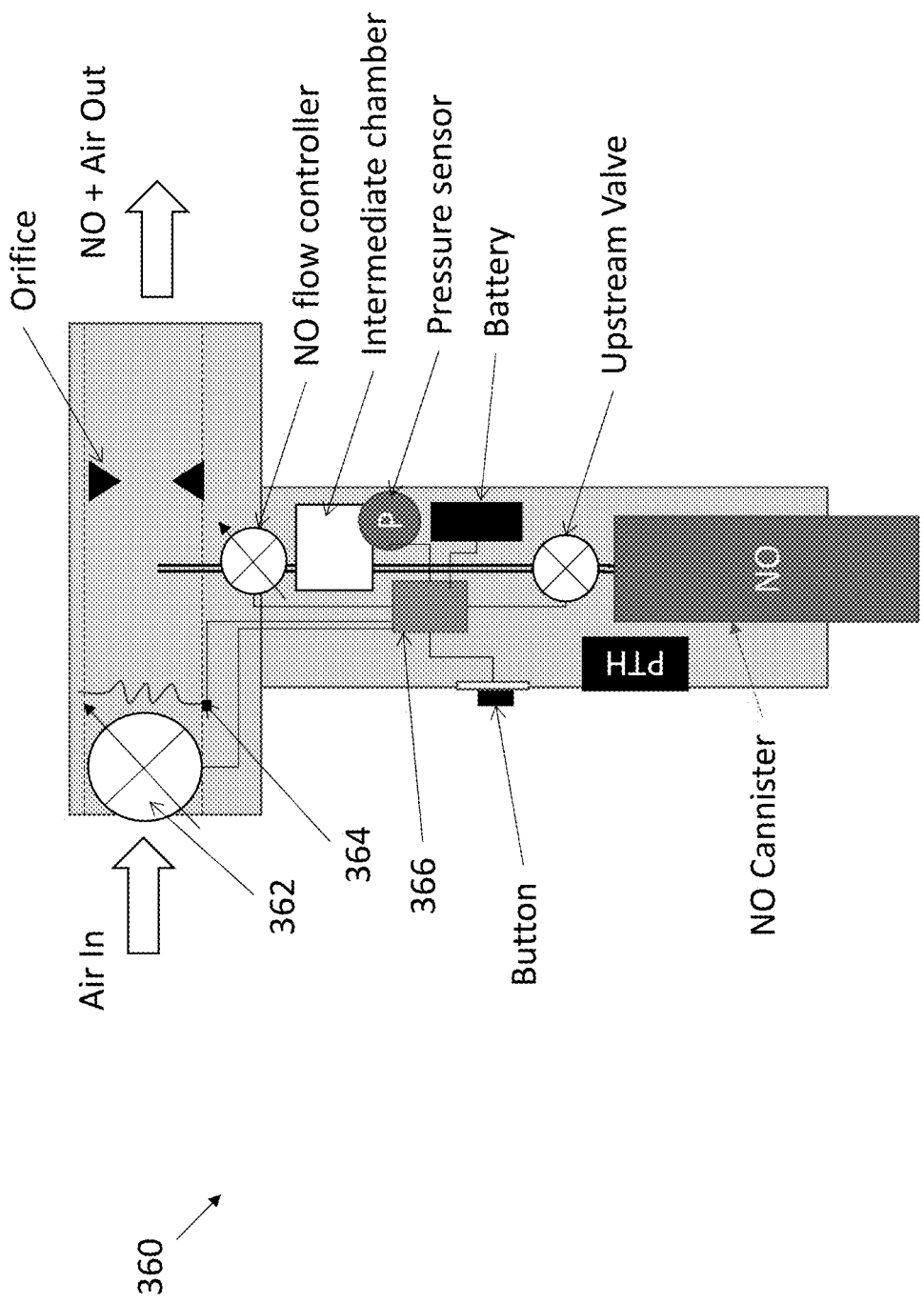
FIG. 16 illustrates an exemplary embodiment of NO inhaler with inspiratory flow control with closed loop feedback.

Critical orifices may be passive and static or actively controlled. In some embodiments, a NO delivery device can actively control the inhaled gas flow restriction to maintain a more consistent mass flow rate of inspiratory gas through the system. FIG. 16 depicts an NO inhaler device 360 with an actively controlled valve or inspiratory flow controller 362 at the air inlet that actively varies the flow restriction of the inspiratory gas pathway in response to the measured inspiratory mass flow rate. When a user pulls hard, the controller adjusts the valve to a smaller effective orifice size. When the user pulls softly, the controller adjusts the valve to a larger effective orifice size to maintain a target inspiratory flow rate. In the embodiment depicted, the controller 366 adjusts the inspiratory flow controller based on the measured inspiratory flow rate using a flow sensor 364. In some embodiments (not depicted), the inspiratory pressure is measured between the flow controller and the patient and the controller can adjust the inspiratory flow controller to maintain a specific inspiratory pressure that is associated with a target flow rate, based on prior characterization of the device.

Dose Levels and Dose Control

Gas concentrations delivered by an inhaler device can range from low (e.g., 0.5 ppm) to the full concentration of the compressed gas cylinder (e.g., 800 ppm, or 2000 ppm). In some embodiments, NO is delivered to the inspiration flow at a rate that delivers 200 ppm in a 500 cc breath once every hour. In some embodiments, a target number of NO molecules are delivered to a breath (e.g., 0.7 mg per breath). In some embodiments, a target number of mg of NO is delivered per unit time (e.g., 6 mg/hr) where the NO device varies the amount of NO delivered to each breath based on the prescribed dosing rate and quantity of breaths dosed over time. In some embodiments, a NO device varies one or more of the duration, flow rate and concentration of a NO pulse to maintain a particular dosing schedule. In embodiments involving electrical generation of NO, NO pulse concentration is varied by varying plasma parameters (e.g. one or more of frequency, duration, current, reactant gas flow). It will be understood that the concentration of NO delivered through the inhaler device can depend on the purpose of the NO delivery. For example, the NO dose can be used to treat infections or to dilate vessels. The range of the NO concentration can vary, and for example, can be between 1 ppm-80 ppm, 1 ppm-400 ppm, or 1 ppm-1000 pm.

When a particular dosing schedule is prescribed, this information can be programmed into the NO inhaler device controller. For example, if a user is to breath 3 breaths of NO every hour, the NO inhaler can alert the user, for example by sounding an alarm, illuminating one or more lights, and/or vibrating, that it is time for the next dose. If the user is expected to breath three breaths in succession, the NO inhaler can count the breaths and trigger an alarm if the user delays too long between dosed breaths or appears to have forgotten one of the breaths in the series. For example, if the user is to inhale 3 breaths in succession and only inhales 2 of the three breaths, the device will sound a reminder alarm to inform the user that they need to inhale another breath of NO. Each clinical application will have a specific dose level and target exposure time. For example, killing bacteria requires the NO concentration to exceed a minimum threshold for a minimum amount of time. If a user does not administer the device in a way that results in sufficient exposure time (e.g. 2 breaths instead of 3 breaths), the device may require the user to repeat the entire 3-breath sequence again in some instances.

Figure 17:
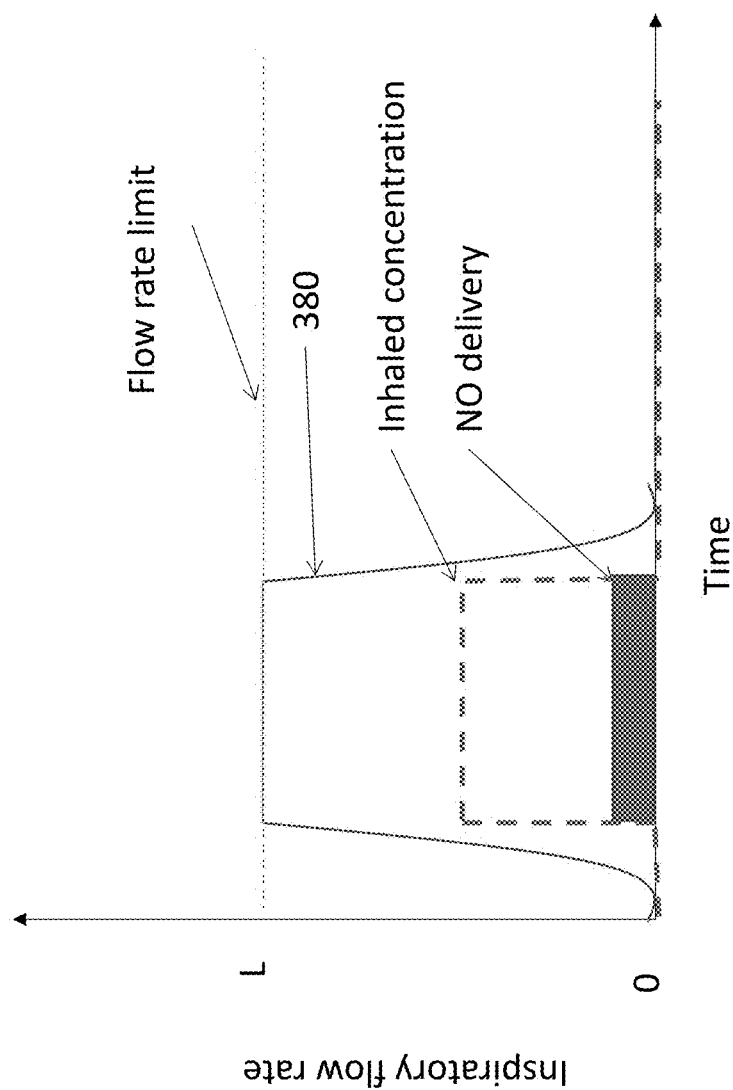
FIG. 17 illustrates an exemplary graph showing inspiratory flow, dosing and concentration profile with governed inspiratory flow rate.

In some embodiments, NO-containing gas is delivered at a constant flow rate when the inspiratory flow rate is at a target level, as shown in FIG. 17. FIG. 17 shows an exemplary graph of inspiratory flow rate 380 over time and shows how the inspiratory flow rate increases from zero up to a governed limit. While the inspiratory flow rate is within a tolerance of that flow rate (e.g., +/−10%), NO is delivered.

Figure 18:
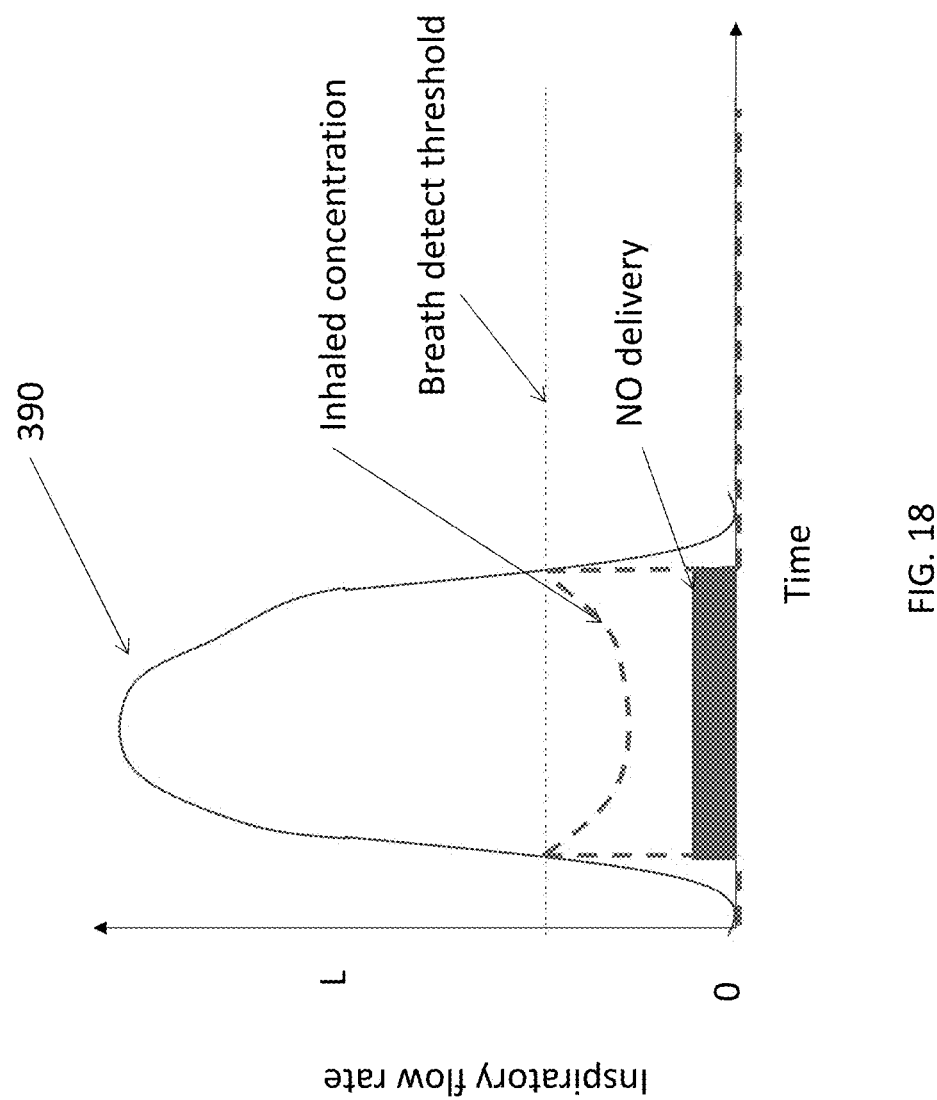
FIG. 18 illustrates an exemplary graph showing inspiratory flow, dosing and concentration profile with unconstrained inspiratory flow.

In an exemplary graph depicted in FIG. 18, NO is delivered to the user whenever the inspiratory flow rate 390 exceeds a threshold. This ensures dosing across the duration of the breath and ensures that there is sufficient gas flow at the end of the inspiratory event to purge the NO device with air. Since the inspiration continues after the flow rate decreases below the inspiratory threshold, any residual NO within the device is removed from the device before the inspiration ends. This mitigates against the formation of NO2 within the device between uses. The concentration of NO within the breath varies during the breath, as depicted in FIG. 18. This is because the NO flow rate is constant while the inspiratory flow varies. Higher inspiratory flow rates result in lower inhaled concentration of NO. This approach can be acceptable for applications that deliver a target quantity of NO molecules (e.g. mg/hr dose), but may not achieve sufficient concentration in applications that require a minimum inhaled concentration (e.g. infection treatment).

Figure 19:
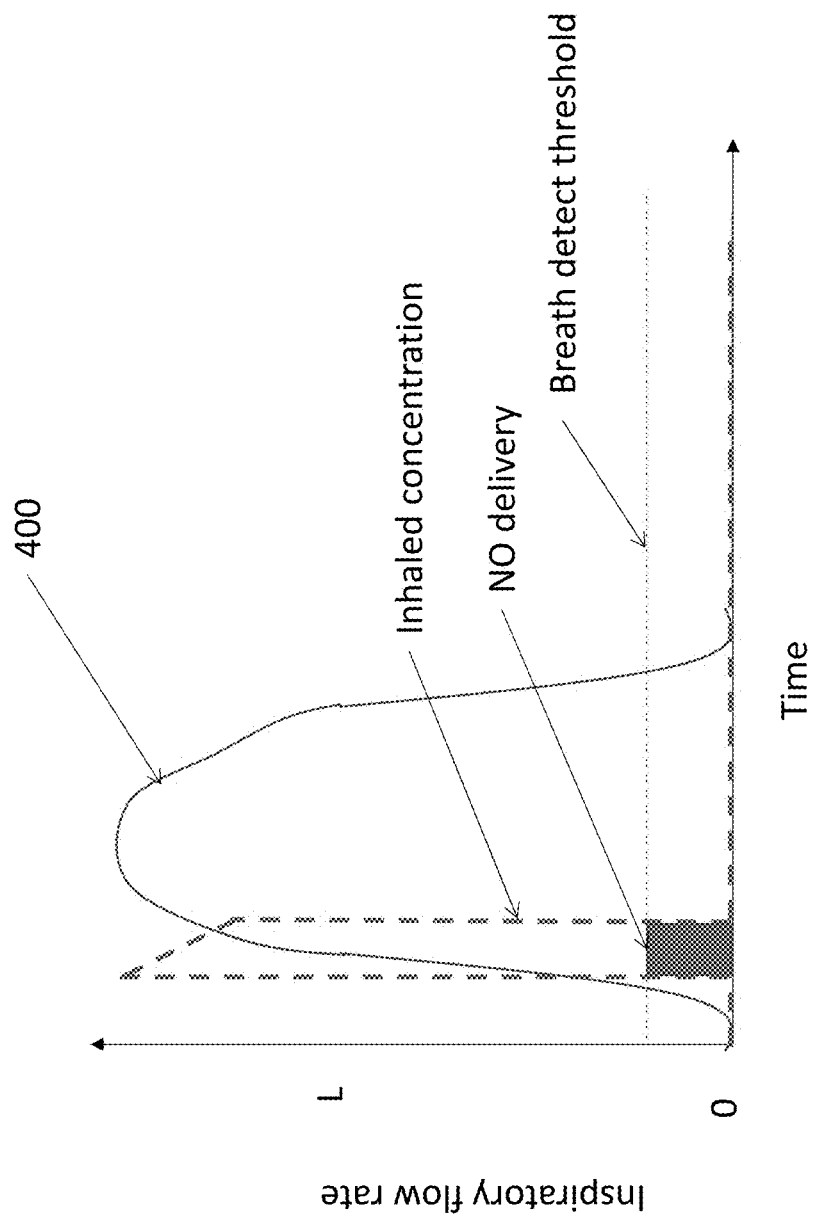
FIG. 19 illustrates an exemplary graph showing pulsed NO delivery at the onset of inspiration.

FIG. 19 depicts an exemplary graph of inspiratory flow rate 400 over time that shows generation/delivery of a pulse of NO during an inspiratory event. In some embodiments, the NO pulse is generated/delivered as soon as an inspiration is detected. In some embodiments, the NO pulse is delivered at another point during the inspiration (e.g. max inspiratory flow rate, inflection point when inspiratory flow rate begins to slow).

Figure 20:
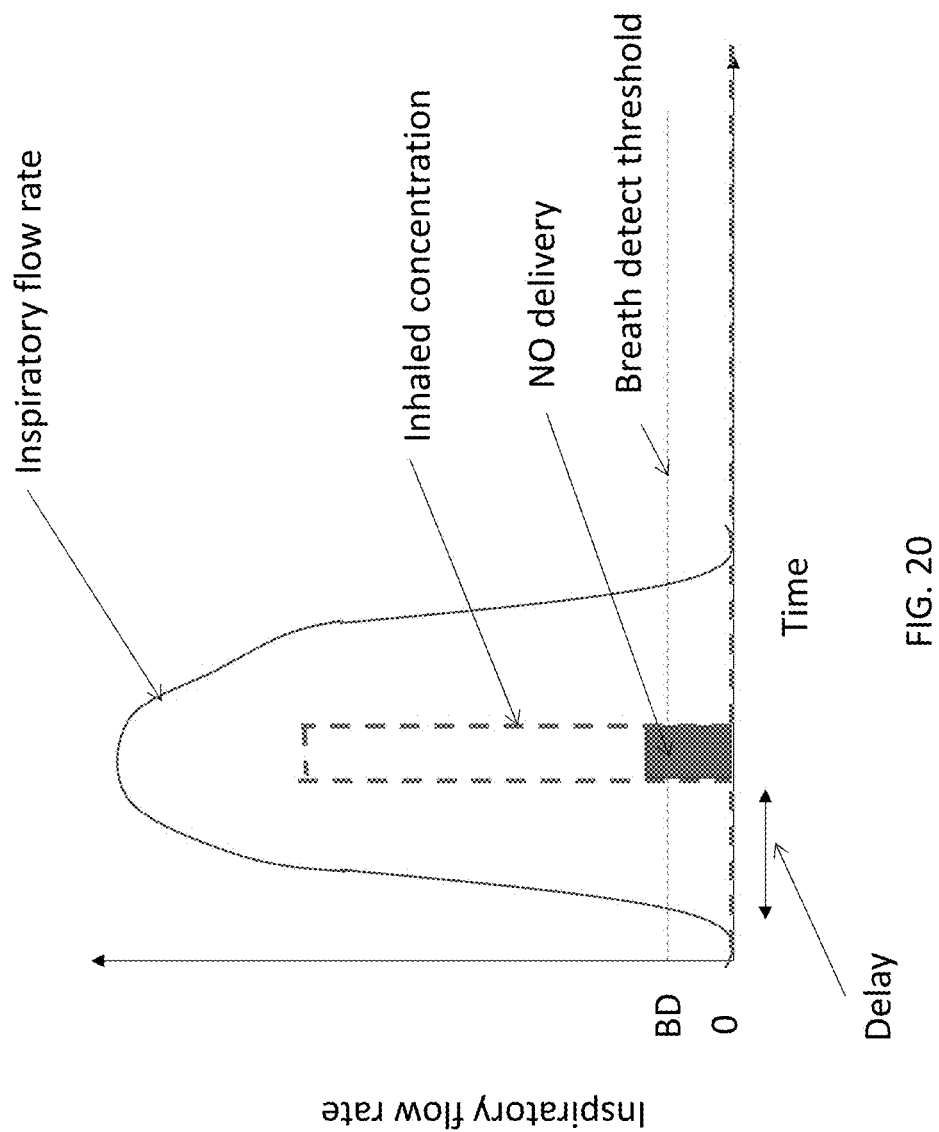
FIG. 20 illustrates an exemplary graph showing pulsed NO delivery delayed from inspiration detection.

In some embodiments, the pulse is delivered a set amount of time after the inspiration is detected (e.g., 0.25 seconds). FIG. 20 depicts an exemplary graph that demonstrates that delivery of the same pulse as shown in FIG. 19 later in the inspiratory event lines up with a period of higher flow within the inspiratory event which correlates with lower inspired concentration and a greater volume of inspired gas dosed, thereby reaching a larger portion of the lung. The system controller in FIG. 20 detects a breath when the inspiratory flow rate crosses a threshold at which time the delay counter begins. Other approaches to determining NO pulse delivery timing can be used as well. It should be noted that although a NO inhaler delivers NO directly to the user, there is a transit time from plasma chamber to the user. In some embodiments, this transit time is taken into account when determining the timing of a pulse. For example, if it is desired to deliver an NO pulse 0.5 seconds into an inspiratory event and it takes roughly 50 msec to detect an inspiration and another 25 msec transit time for the NO to reach the mouth of the user, a NO delivery device will delay NO generation/delivery for 425 msec (500 msec minus 50 msec minus 25 msec) to account for the delays and make the NO arrive at the target time.

Flow Assistance

Some users have difficulty inspiring air. Requiring this subset of users to inspire through a device can add flow resistance to their inspiratory effort. In some embodiments, the inhaler device includes a means to propel gas to the user to supplement their inspiratory effort (i.e., positive pressure ventilation). The inhalation assist component can either be separate from the inhaler or integrated into it. In some embodiments, the inhaler includes an electrical pump (e.g., motor and blower, fan, diaphragm pump) to push air towards the user.

Figure 21:
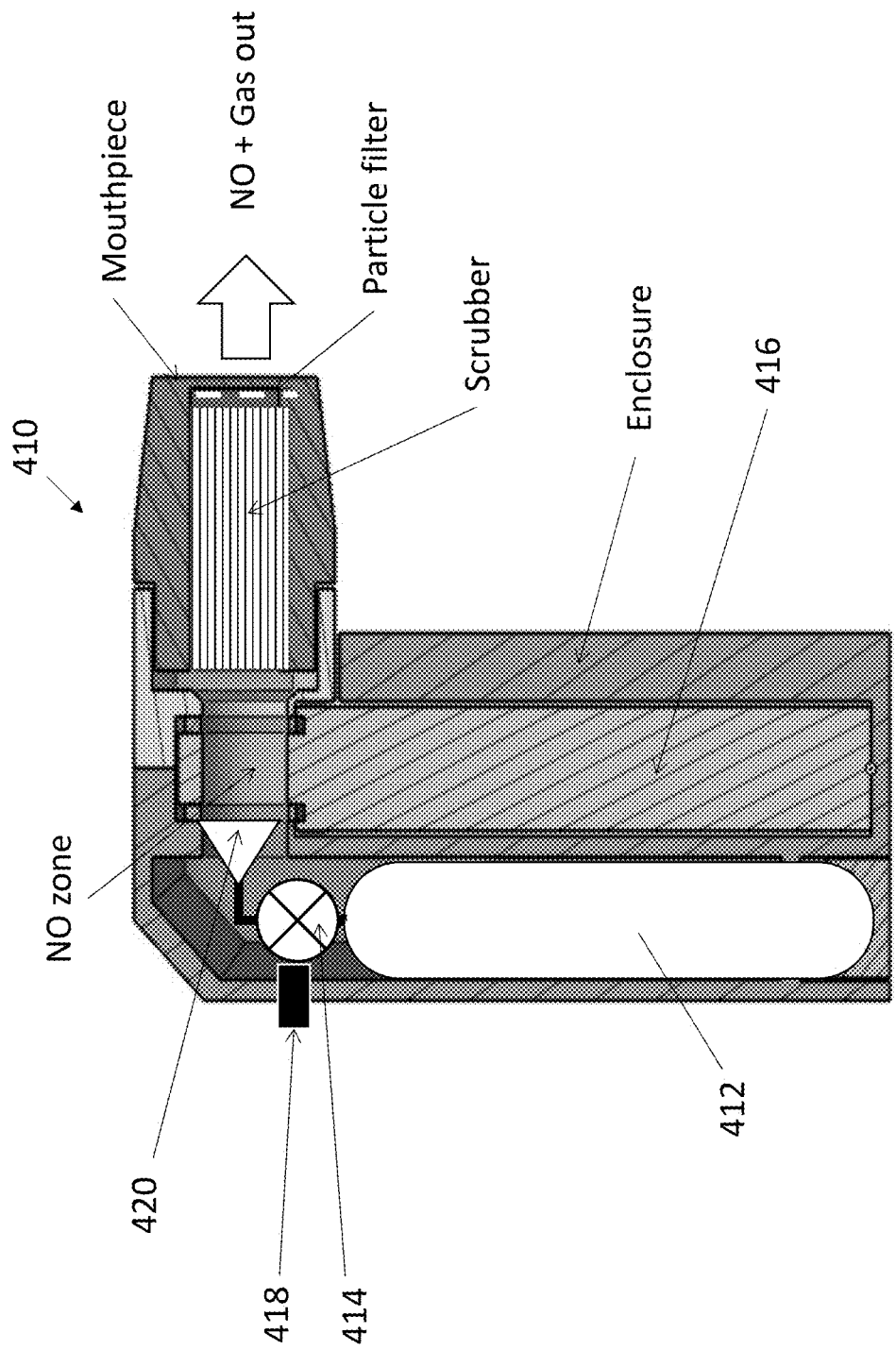
FIG. 21 depicts an exemplary embodiment of a NO inhaler device that sources oxygen/nitrogen gas form a compressed cylinder.

In some embodiments, the pressure of a cylinder of compressed gas is utilized to push NO-containing gas to the user. In some embodiments, a compressed gas cylinder filled with air is utilized to propel air towards the user. In some embodiments, NO is electrically generated in the released air. This can provide medically pure air, eliminating the need for inlet scrubbers and/or humidity controls as well as producing NO with high purity. FIG. 21 depicts an embodiment of an NO inhaler device 410 where inspired air is sourced from a compressed gas cylinder 412 within the device. Flow from the compressed gas cylinder can be controlled by either the user operating a manual valve 414 or a treatment controller 416 within the device that detects a switch 418 activated by a user and actively opens the gas valve. In the depicted embodiment, compressed gas flows through a valve and a nozzle 420 that control the flow and flow profile, respectively. In some embodiments, the compressed gas consists of an oxygen/nitrogen mixture. In some embodiments, the ratio of oxygen to nitrogen is 50/50. Higher levels of oxygen than the typical atmospheric level of 21% can improve the efficiency of NO generation and provide additional oxygen to the user.

In some embodiments, the NO delivery device depicted in FIG. 21 can be recharged on a base station. The base station makes electrical contacts to charge the device battery and/or compresses air into the compressed gas cylinder.

Figure 22:
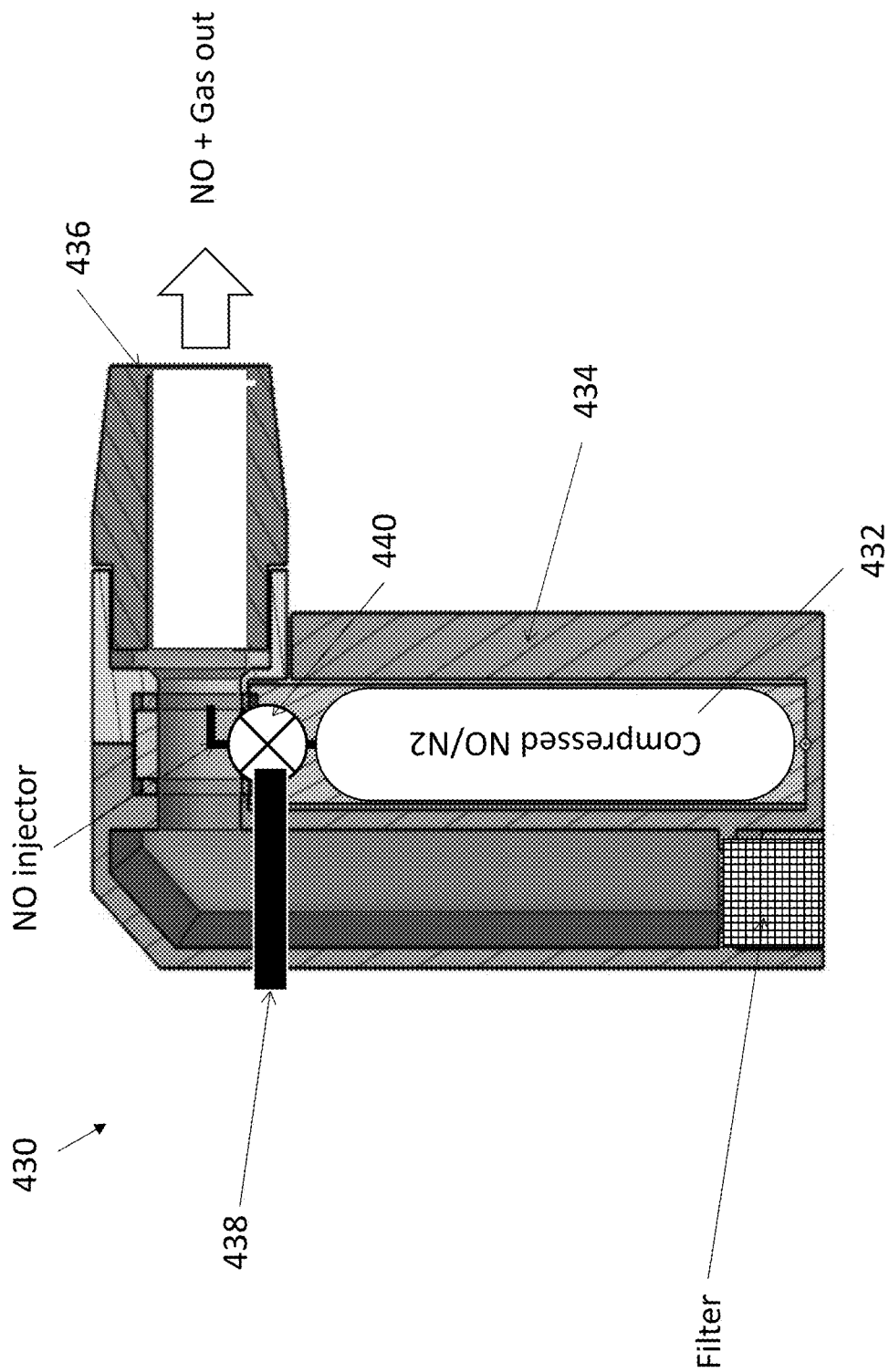
FIG. 22 depicts an exemplary embodiment of a NO inhaler device that sources NO from a compressed cylinder.

FIG. 22 depicts an embodiment of a NO inhaler device 430 that sources NO from a compressed gas container 432 positioned in an enclosure 434. In some embodiments, the compressed gas container is filled with pure NO. In some embodiments (as shown), the compressed gas container is filled with a combination of NO and an inert gas (e.g., N2 or Helium). To deploy the device, the user inserts a mouthpiece 436 into their mouth and inhales. As they inhale, they depress a button or activation switch 438 that opens a gas valve 440 that releases the NO-containing gas into the air stream. A particle filter at the air inlet removes any environmental particulate from the gas stream. In some embodiments, the pressure of the NO gas container is reduced with a pressure regulator before the valve to decrease pressure on the valve and decrease the flow rate exiting the container. Higher concentration nitric oxide containers require less flow for a given dose. This can be advantageous so that the change in pressure within the container is less with each pulse, preventing excessively cold nitric oxide gas in the inspiratory flow.

Figure 23:
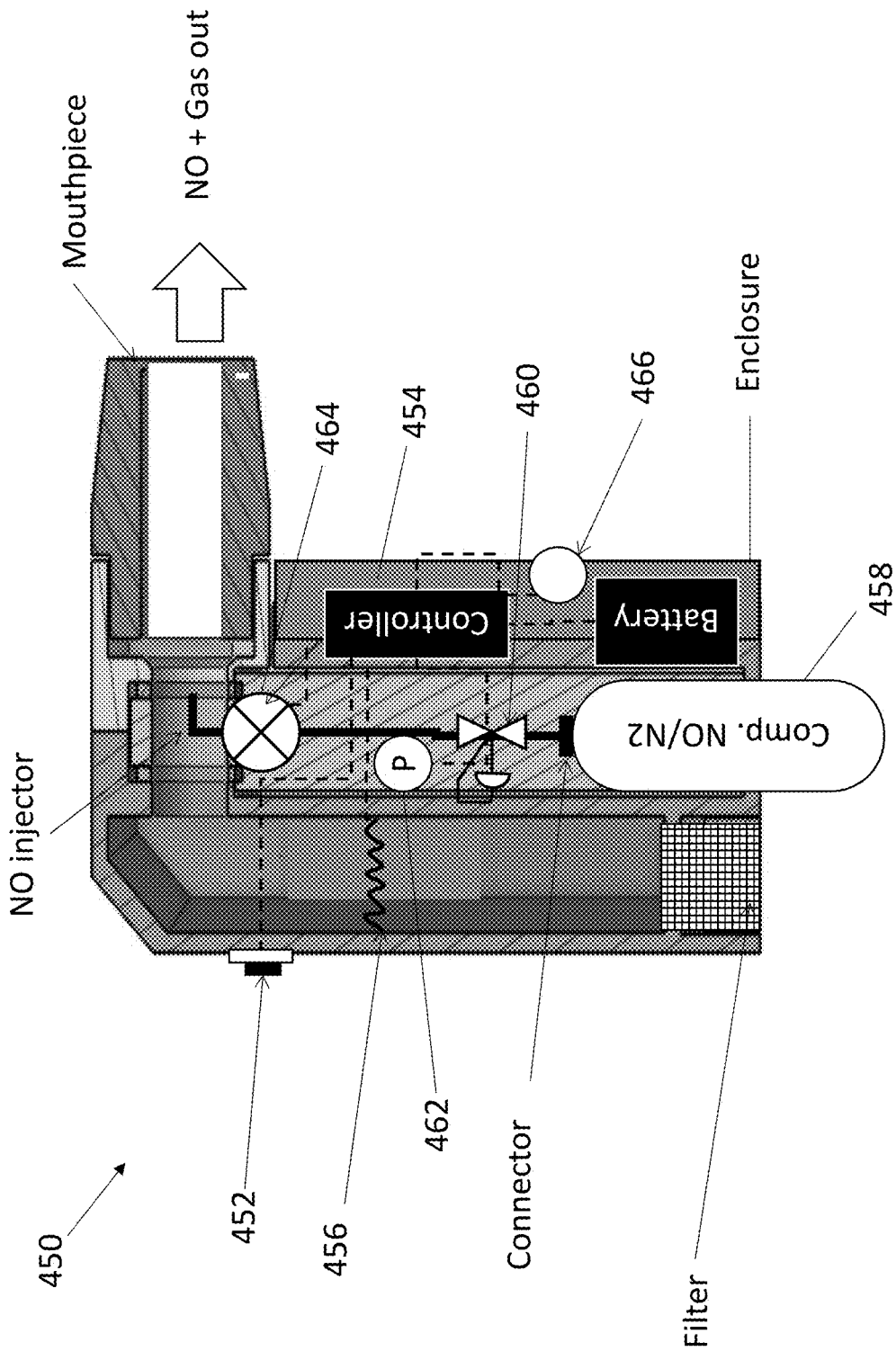
FIG. 23 depicts an exemplary embodiment of a NO inhaler device that sources NO from a compressed gas cylinder with smart flow control.

FIG. 23 depicts an embodiment of a NO inhaler device 450 with smart gas delivery. As the user inhales, they depress an activation switch 452 which is registered by the treatment controller 454. The controller measures the flow rate of inspired gas with a flow sensor 456 (e.g., hot wire sensor shown). High pressure NO gas in a removable gas cylinder 458 is reduced in pressure by a pressure regulator 460. A pressure sensor 462 downstream of the pressure regulator informs the controller of the NO gas pressure available. When the NO gas pressure falls below a threshold, the controller can prompt the user to replace the gas cylinder. The controller also controls a valve 464 that releases NO gas into the inspiratory gas stream. In some embodiments, the valve is a binary valve that opens to a consistent level, permitting NO to flow. In some embodiments, the binary valve is pulse-width modulated to provide a target NO flow on average. In some embodiments, the valve is a proportional valve that enables a variable flow of NO to be introduced to the inspiratory flow. In some embodiments, the NO is introduced to the inspiratory flow proportionally. In some embodiments, the NO is released to dose a particular portion of the inspiration (e.g. beginning, middle, end) to treat a particular region of the airway and/or lung. An ambient conditions sensor 466 is used by the controller to measure one or more of ambient pressure, temperature and humidity. In some embodiments, the controller uses these measurements as an input to an algorithm or look-up table for determining the amount of NO to release. The system is powered by a battery. In some embodiments, the battery is built in and the device is disposable. In some embodiments, the battery is replaceable. In other embodiments, the battery is rechargeable.

Figure 24:
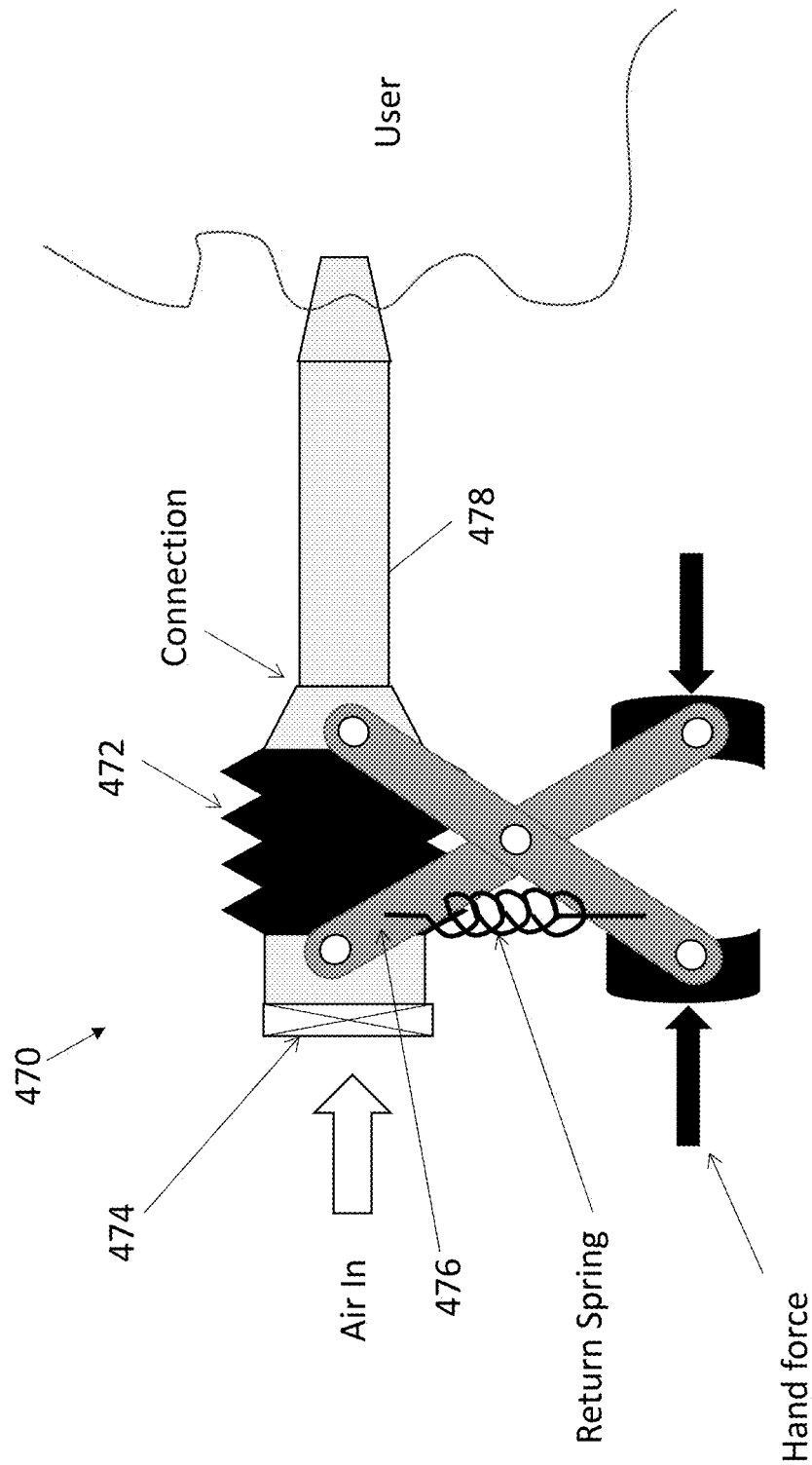
FIG. 24 illustrates an exemplary embodiment of an inspiratory assist device utilizing scissors mechanism and bellows.

In some embodiments, the user is able to use their muscle force and/or body weight to help push in sufficient air with NO. FIG. 24 depicts an embodiment of an NO inhaler device 470 where the user squeezes a grip to compress a reservoir 472 and assist their diaphragm in inspiration. Air enters the reservoir 472 (e.g., bellows) through a check valve, such as a one-way valve 474. When the user squeezes the grip, a scissors mechanism 476 compresses the bellows, forcing air through an inhaler 478 and to the user. In some embodiments, the scissors mechanism includes a spring (e.g., a tension spring as shown, or a compression spring) to assist in returning the mechanism to an initial position.

Figure 25:
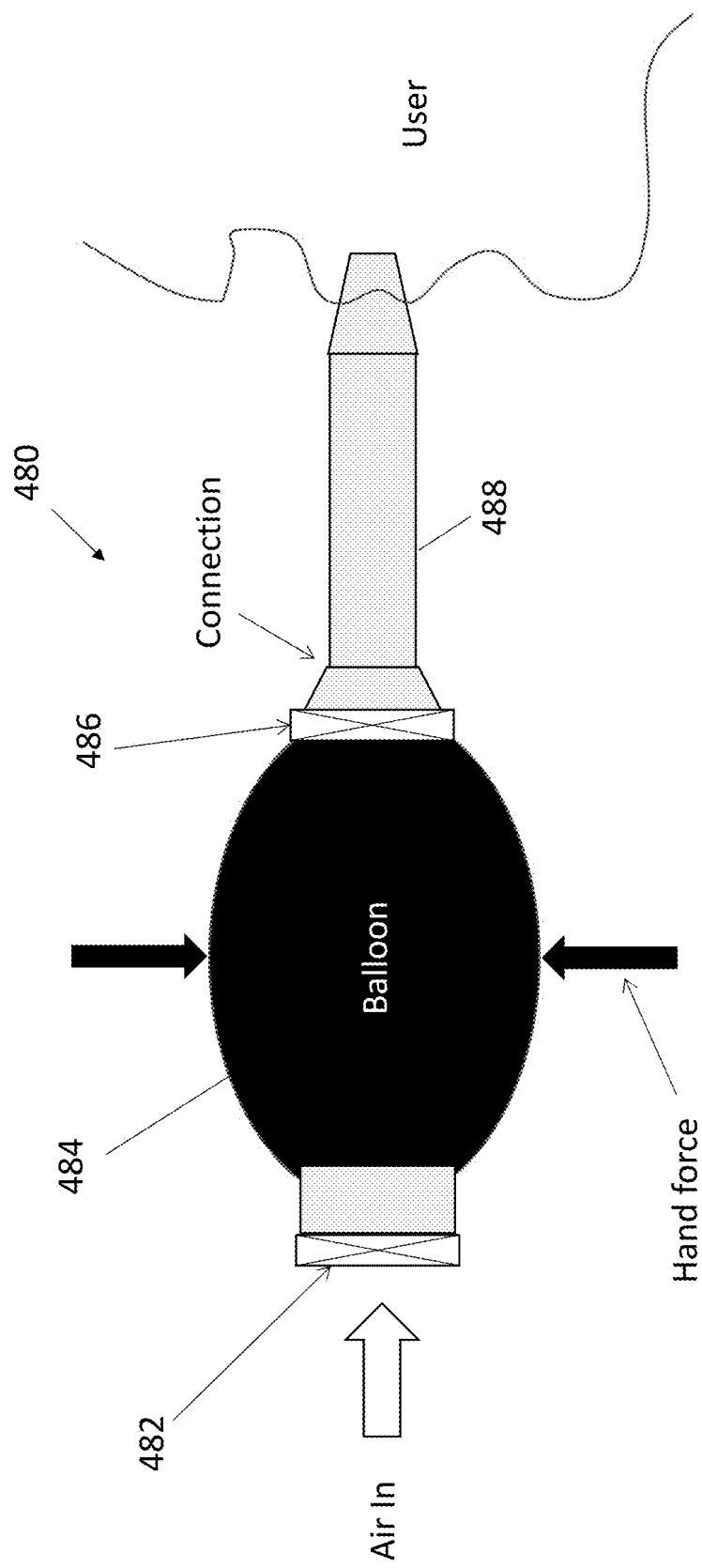
FIG. 25 illustrates an exemplary embodiment of an inspiratory assist device utilizing a reservoir squeezed by hand.

FIG. 25 depicts another embodiment of an NO device inhaler 480 with an inhalation assist design. Air enters through a one-way valve 482 and into a reservoir 484. In this embodiment, the reservoir is a stiff balloon, however other types of self-filling reservoirs can be used. When the user squeezes the balloon, air within the balloon is pushed to the user through a second one-way valve 486 and the inhaler device 488. The second 1-way valve ensures that the balloon refills with fresh air from the environment, rather than pulling air away from the user through the inhaler device.

Figure 26C:
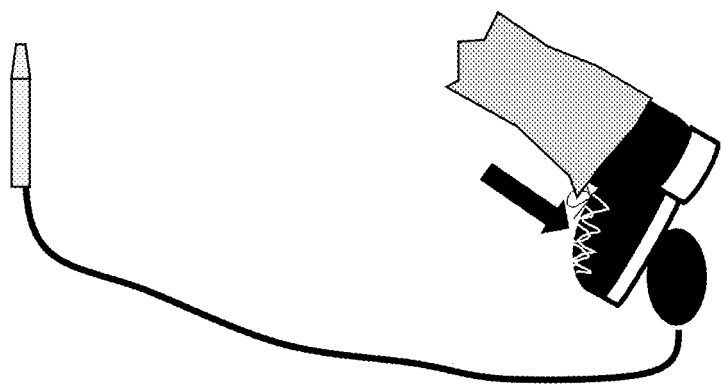
FIG. 26C illustrates an exemplary embodiment of an inspiratory assist device utilizing a reservoir pressurized by standing user's body weight.
Figure 26B:
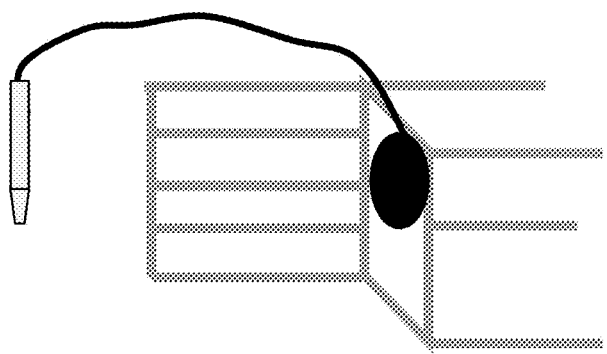
FIG. 26B illustrates an exemplary embodiment of an inspiratory assist device utilizing a reservoir pressurized by seated user's body weight.
Figure 26A:
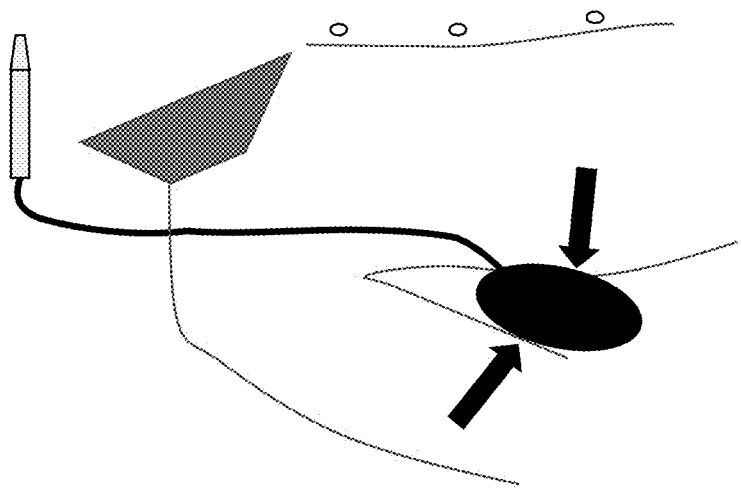
FIG. 26A illustrates an exemplary embodiment of an inspiratory assist device utilizing a reservoir squeezed by armpit.

FIG. 26A depicts an embodiment of a device that utilizes the muscles of the arm pit to compress a volume of air. Similar muscular approaches can be achieved be placing the air reservoir between the knees or behind the knees, or between any parts of the body that would apply a force.

FIG. 26B depicts an embodiment of a device where the user sits on a reservoir and their body weight creates pressure to help fill their lungs. FIG. 26C depicts an embodiment of a device where the places their foot on reservoir and applies their body weight to pressurize air within the reservoir. In some embodiments, as shown in FIG. 26B and FIG. 26C, the mass of the user's body creates a static pressure head. Flow derived from this pressure can be controlled by the inhaler device when the user initiates a breath. In some embodiments, the user presses a pneumatic or electrical button on the inhaler device that initiates gas flow to the user. The button press opens a valve from the pressurized air source either directly (pneumatic valve) or indirectly (electrical circuit recognizes button press and electrically opens the fresh air valve). In some embodiments, the air reservoir size is sufficient to deliver pressurized air for multiple breaths.

These concepts whereby the user uses their muscle force and/or body weight to develop pressure in a delivery gas apply to other applications in which user inhalation of a gas can be enhanced by pressurization. For example, nebulized drug flow, vaporized drug flow, aerosol drug delivery, dry powder drug delivery, and soft mist drug delivery. In some embodiments, a pressure regulator is utilized to enable a constant pressure to be maintained in the delivered gas when the user generates pressure that exceeds a target pressure. In some embodiments, a mass flow controller is utilized to introduce a specific inspiratory gas flow rate to the NO inhaler. The mass flow controller may be a separate device, part of the pressure generation device or part of the inhaler.

It should be noted that pulmonary trauma can occur when positive pressures exceed safe limits. In some embodiments, a positive pressure device includes a pressure relief valve to protect the user from injuring their lung tissue. In some embodiments, the safety limit is 10 cm H2O to 40 cm H2O. In some embodiments, this safety limit can be adjusted by the user and/or prescribing clinician.

Gas Mixing

Figure 27C:
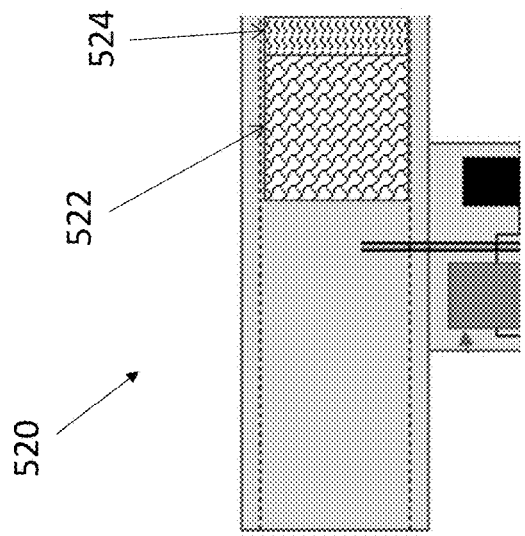
FIG. 27C illustrates an exemplary embodiment of NO mixing with scrubber and filter.
Figure 27B:
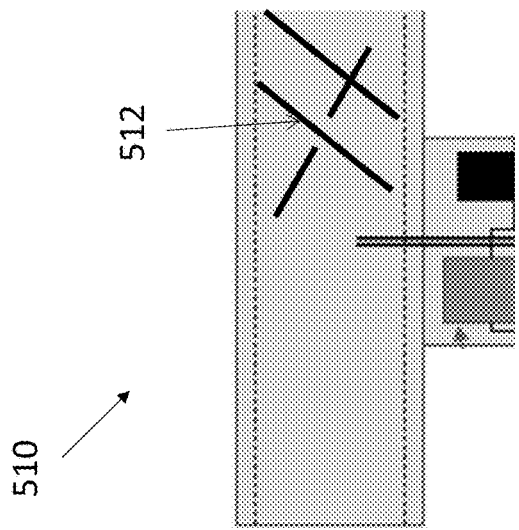
FIG. 27B illustrates an exemplary embodiment of NO mixing with static mixer.
Figure 27A:
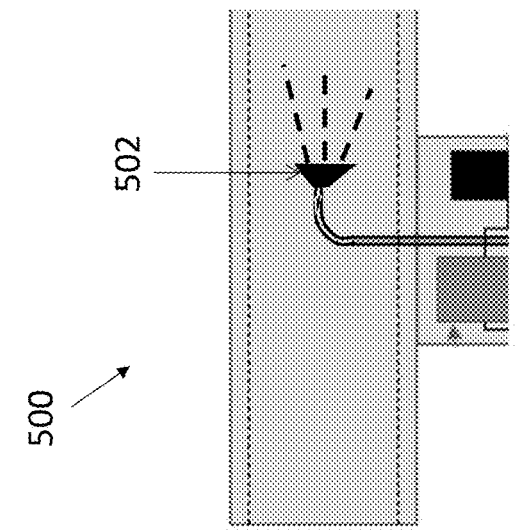
FIG. 27A illustrates an exemplary embodiment of NO mixing with spray.

FIG. 11 Depicts an Embodiment of a Device with NO being Introduced to the Air stream in the center of the flow. This can result in the NO remaining in the center of the flow as it enters the user. Some embodiments utilize various mixing techniques to mix the NO with the inspiratory air for a more homogeneous mixture. This can even out the dosing within the lung. FIG. 27A depicts an embodiment of an inhaler device 500 where the NO flow is introduced parallel to the air stream and exits through a spray nozzle 502 (e.g., shower head) that distributes the NO across the air flow. FIG. 27B depicts an embodiment of an inhaler device 510 that passes the air/NO mixture through static mixing elements 512 to create a more homogenous gas mixture. Other embodiments involve utilizing a dynamic mixer (e.g., rotating fan) to mix the two gas streams (not shown). FIG. 27C depicts an embodiment of an inhaler device 520 that utilizes a scrubber 522 and a filter 524 to clean the inhaled gas stream as well as mixing.

Bypass Flow

Another means to reduce in the amount of effort required by the user to receive a dose of NO is to have a bypass channel, as shown in FIG. 14. FIG. 14 illustrates an embodiment of an NO inhaler device 300 where air enters a bypass channel 332 and merges with the NO flow. The balance of flows between the NO channel and the bypass channel can be managed passively or actively. In the embodiment shown, passive orifices 334, 336 are placed in each pathway to limit the flow through each. In some embodiments, the flow through each pathway is measured and one or more orifices are adjusted to achieve a target mix ratio of NO containing gas and air from the bypass channel. In some embodiments, the bypass channel is utilized for a gas other than air (e.g. oxygen). In one example, a target ratio of 25% NO path flow to 75% bypass gas flow is targeted. The NO inhaler controller uses the flow measurements of bypass and NO gas flow to assess the actual ratio of flows and modulates one or more flow restrictions and/or flow controllers to drive the ratio towards the target in a closed-loop manner.

Exhalation Analysis

In some embodiments of a NO inhaler, the device can also be used to analyze user exhalation. Using flow and/or pressure sensors, the inhaler is able to collect information about the exhaled gas flow. In some embodiments, the inhaler collects flow information and integrates it to determine the volume of exhaled air. In some embodiments, this information is utilized to determine lung capacity. In some applications, a lung capacity measurement provides an indication of tumor size within the thoracic cavity. In some embodiments, the calculated volume of one or more breaths is utilized to predict the tidal volume of one or more subsequent breaths. In one embodiment, the timing of the peak inspiratory flow rate is marked as the mid-point of the inspiratory event. This timing point can be utilized as a guide for delivering drugs to the first or second half of a breath. In some embodiments, the inhaler measures the pressure that a user can generate. In some embodiments, the inhaler processes the pressure and/or flow data to determine heart rate and degree of pulmonary hypertension based on minor fluctuations in the measured signal. In some embodiments, the device characterizes the breathing patterns of a patient (e.g., breath period, flow rate range, tidal volume, inspiratory flow profile) and uses that information for predictive purposes. For example, the typical tidal volume of a patient can be determined by calculating the average tidal volume from a series of breaths. The device can then assume that a subsequent breath will have a similar tidal volume. For a given tidal volume, breaths that fill with a faster flow rate will be shorter in duration than breaths with a slower flow rate. In some embodiments, the delivery device predicts the timing of the midpoint of a breath or the duration of a breath based on the initial flow rate and responds by generating a NO pulse that corresponds with the portion of the breath to be targeted (e.g., initial ½, final ½).

Flow Governing

Accurate concentrations of NO with inhaled air requires known flow rates. In some embodiments, the inhaler measures the inhaled gas stream flow rate and introduces proportionate amounts of NO. In other embodiments, the inhaler governs the gas flow to the user so that the gas flow is more defined. In some embodiments, a critical flow restriction (e.g., orifice, mesh, or perforated sheet) is used to prevent inhaled gas flow from exceeding the maximum dose rate of the inhaler device. Otherwise, high flow rates of inhaled gas would be underdosed. In some embodiments, the inhaler dynamically varies a flow restriction (for example, using variable resistance) within the inspiratory gas flow to maintain a known mass-flow of air as the user inhales to facilitate accurate dosing. In some embodiments, the device controller manipulates a valve to modulate the flow restriction during an inspiratory event to achieve a flow rate within a target range. In some embodiments, the NO device provides a constant production (e.g., 1000 ppm·lpm) whenever the inspiratory flow is within a specified range. This approach enables the system to be optimized for power efficiency at a specific production level.

In some embodiments, the inhaler provides the user feedback so that they can achieve an inspiratory flow rate within a target range. In some embodiments, the inhaler includes an array of two or more lighted indicators. For example, one light or lamp can be used to indicate that the flow rate is too high, and one lamp can be used to indicate that the flow rate is too low. In some applications, a 3rd light is utilized to indicate that the flow is correct. Additional lamps can be utilized for finer resolution feedback. In some embodiments, the inhaler utilizes a speaker to emit a sound indicative of the flow rate. In one example, as the user inhales, the frequency of the sound emitted by the inhaler increases to a maximum frequency corresponding with the target inhaled flow rate. If the user exceeds the target flow rate, the sound frequency begins to decrease, indicating that optimal flow rate has been exceeded. In some embodiments, the emitted sound is pulsed when the inspiratory flow rate is too slow and becomes continuous when an acceptable flow rate has been achieved.

For systems that govern the inhaled flow rate, there are limits to what range of inhaled flow rates can be acceptable to a user. Even a fit person will find it uncomfortable to inhale over a period of 10 to 20 seconds. Thus, the range of flow rates that inspiration can be limited to is finite, typically ranging from 1 to 40 lpm. For a given inhaled volume, slower flow rates fill the user's lungs over more time, allowing for lower NO production levels (ppm·lpm) during inhalation. FIG. 28 presents a table of example inspiratory volumes and NO production levels for an electric NO generator where the inspiratory flow rate equals the reactant gas flow rate (i.e., all of the inspired flow travels through the plasma chamber). The FIG. 28 demonstrates how faster inspiratory flow rates require higher production levels of NO to achieve a target concentration. By limiting the inspired flow rate, a NO generator and/or NO delivery device can deliver sufficient NO to achieve the target.

In some embodiments, for cylinder-based NO, the NO can be packaged with an inert carrier gas, typically nitrogen. Treatments involving NO dosing for a series of breaths (e.g., ventilator treatment) can require supplementary oxygen due to dilution of atmospheric oxygen levels from the NO gas mixture. For example, an 800 ppm cylinder dosing at 80 ppm (10% of cylinder concentration) will dilute the inhaled air with nitrogen and NO by 10%, thereby reducing O2 levels from 21% to 19% in a ventilator application. Breathing a series of breaths at lower oxygen levels can result in hypoxemia in a user, however, breathing a discrete single breath every few minutes or more has little to no effect on user oxygenation. In some embodiments, a user periodically inhales a breath of undiluted cylinder gas which contains no oxygen. In some embodiments, the inhaled volume is a mixture of atmospheric air and gas from the compressed gas source.

Concomitant Therapies

In some embodiments, a NO inhaler is utilized in combination with or in sequential administration with other inhaled therapies. Inhaled NO dilates the airways and in the pulmonary vasculature by relaxing the smooth muscle in the airway and vascular tree, lowering the airway and vascular resistance thereby increasing airflow and pulmonary blood flow. These effects increase the uptake of oxygen but also co-administered inhaled therapies within airways and blood vessels of the lung.

Some inhaled medicines have low distribution within the lung pulmonary vasculature, so the coadministration with inhaled NO may enhance the penetration of such drugs to their target organ, be it the airways, lung tissue or pulmonary vasculature. The NO can be delivered simultaneously with the other medicine(s) but could also be delivered prior to or after the other medicine. The effect of inhaled NO wears off within the body in the order of 30 to 60 seconds, so inhalation of additional medicines in that time frame would be expected to have benefit, and closer timing may have a more pronounced effect.

An example of NO being delivered in combination with a drug is nicotine delivery from a cigarette. Hundreds of ppm of NO are present in the cigarette smoke, having an effect to accelerate nicotine uptake. Commercially available vaping devices deliver nicotine without NO. In some embodiments, NO can be delivered in combination with nicotine. This is done to accomplish a similar dose and effect as a cigarette without the dangerous particulate and tars associated with cigarette smoke.

In some embodiments, a NO generator and/or NO delivery feature is integrated into another inhaled medicine device. One embodiment consists of a combination nebulizer/NO delivery device. Another embodiment consists of a combination gas blender and NO generator. Another embodiment consists of a NO generator and drug thermal vaporizer. In each of these examples, a user is to receive an inhaled medication in aerosol, powder, or gaseous form. Various strategies exist for enhancing the uptake of these substances. In some embodiments, a user first inhales one or more breaths of NO-containing gas to dilate the airways and pulmonary vasculature and increase airflow and blood flow through the lungs. This is followed by a subsequent series of one or more breaths of the inhaled substance. This approach is referred to as "alternating treatments". In some embodiments, the user cycles between independent inhalation of NO to independent inhalation of the other substance. In some embodiments, this can be accomplished by switching between two devices, although this can be complicated and burdensome for the user. In some embodiments, a single device provides alternating breaths of NO and an alternative substance. This greatly simplifies the therapy for the User as they only have to focus on breathing through a single device. In one example, two breaths are dosed with NO followed by a single breath dosed of nebulized drug, then the NO is delivered again. This can repeat for multiple breath series.

Combining therapies into a single device also greatly simplifies the device. The two drug delivery methods can share various system components including one or more of the battery, user interface, microcontroller/processor, breath detection mechanism, power supply, charging circuit, patient sensor, disposable cartridge, user display, alarm system, and enclosure.

Figure 29:
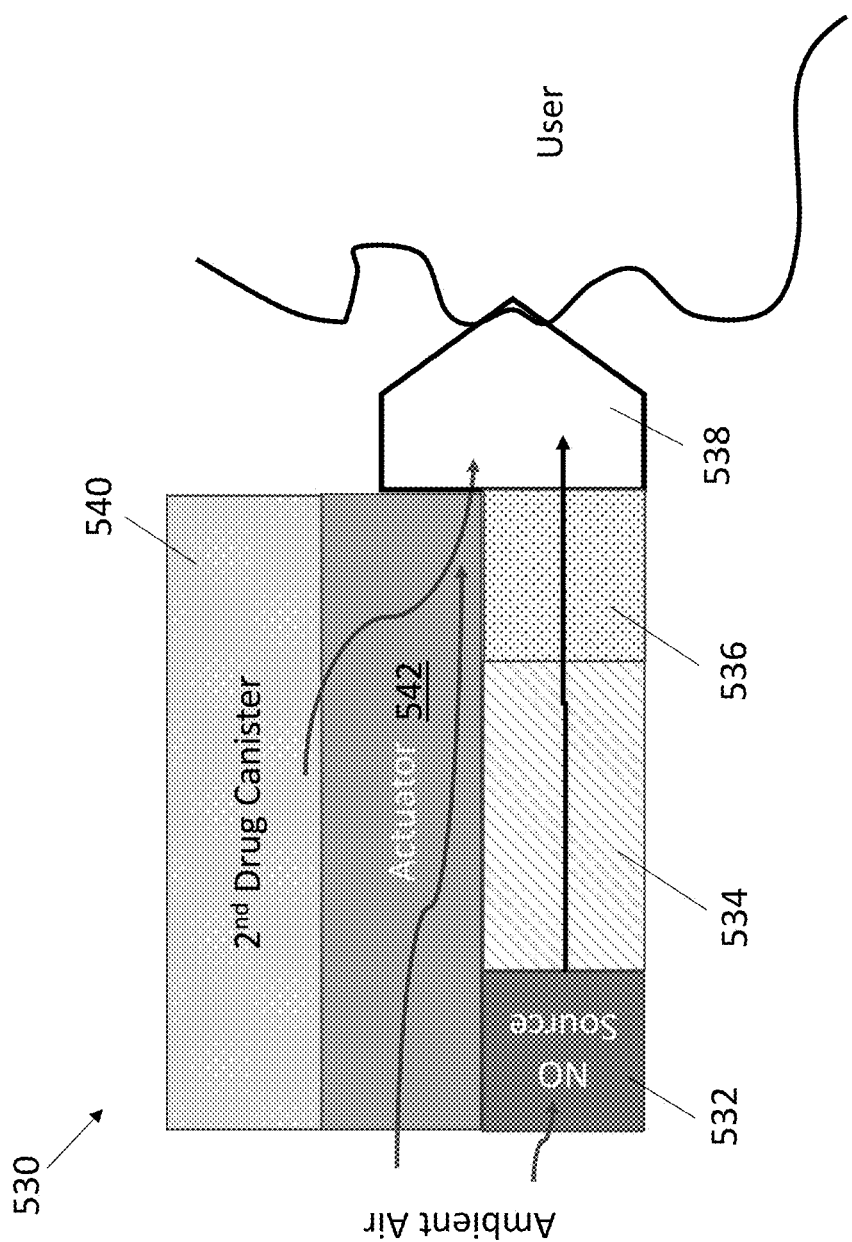
FIG. 29 illustrates an exemplary embodiment of a NO generator with secondary drug delivery capability.

Various architectures and devices can be used for delivery of a combination of NO and another drug. In some embodiments, an integrated device can include two separate flow paths, one with a secondary drug source (e.g., nebulizer) and one with a NO source. FIG. 29 depicts an embodiment of an inhaler device 530 with separate flow paths for NO and a secondary drug. Reactant gas, such as ambient air, enters the system and passes through a NO generator 532, a scrubber 534, and a filter 536 to reach a mouthpiece 538. A secondary drug is stored in a canister 540 and introduced to an air stream by an actuator 542 (e.g., a vibrating mesh nebulizer, a spray nozzle, a flow controller, a powdered drug introducer, etc.). As the user inhales, the user draws gas through both gas flow streams for simultaneous drug delivery. As depicted, the scrubber and secondary drug canister are separate components. In some embodiments, they are combined into a single disposable assembly. This kind of system can be used for combination therapy with other drugs delivered through an inhaler (e.g., albuterol) to increase the uptake/efficiency of a delivered drug. There is increased drug transport from the terminal airways to the terminal pulmonary arterioles as well as across the alveolar wall by dilating the terminal airways that contain airway smooth muscle and by increasing blood volume in the terminal pulmonary arterioles that is available to uptake the drug in question. In some embodiments, NO doses for this approach are in the range of 1 to 40 ppm.

Figure 30A:
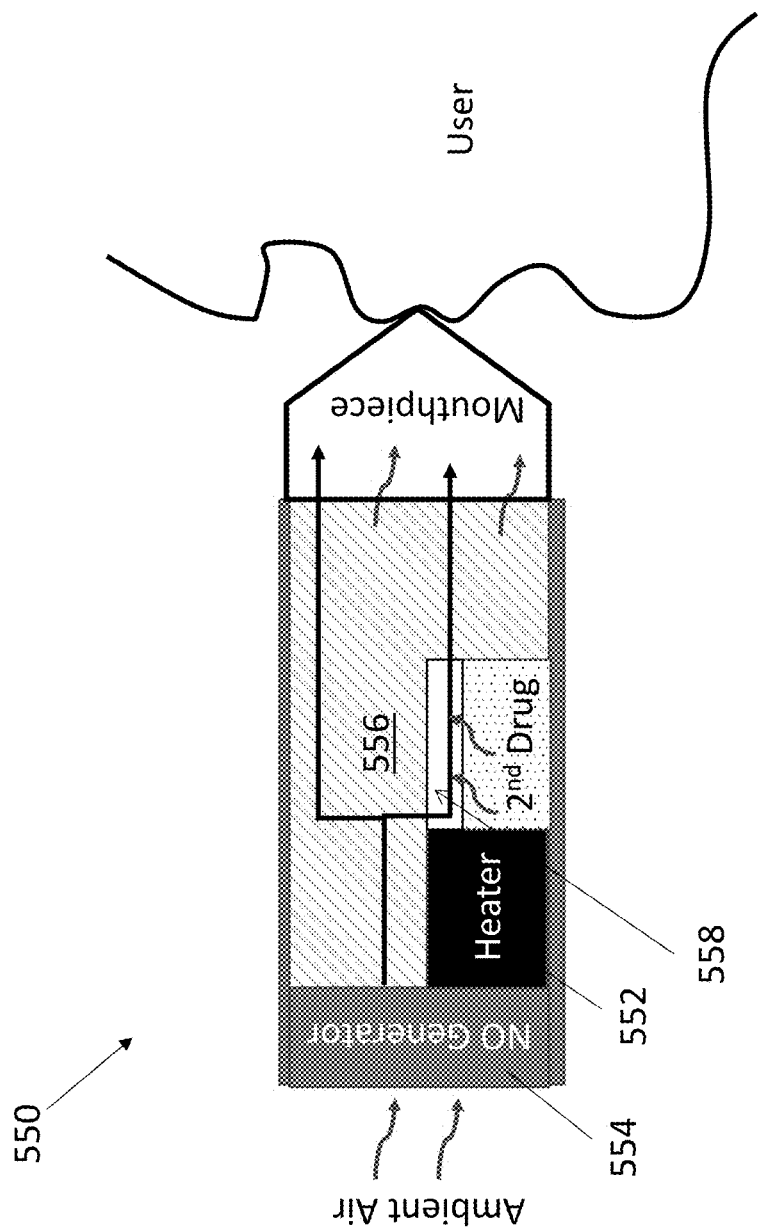
FIG. 30A illustrates an exemplary embodiment of a two drug delivery device where the secondary drug is vaporized into NO-containing gas.
Figure 30B:
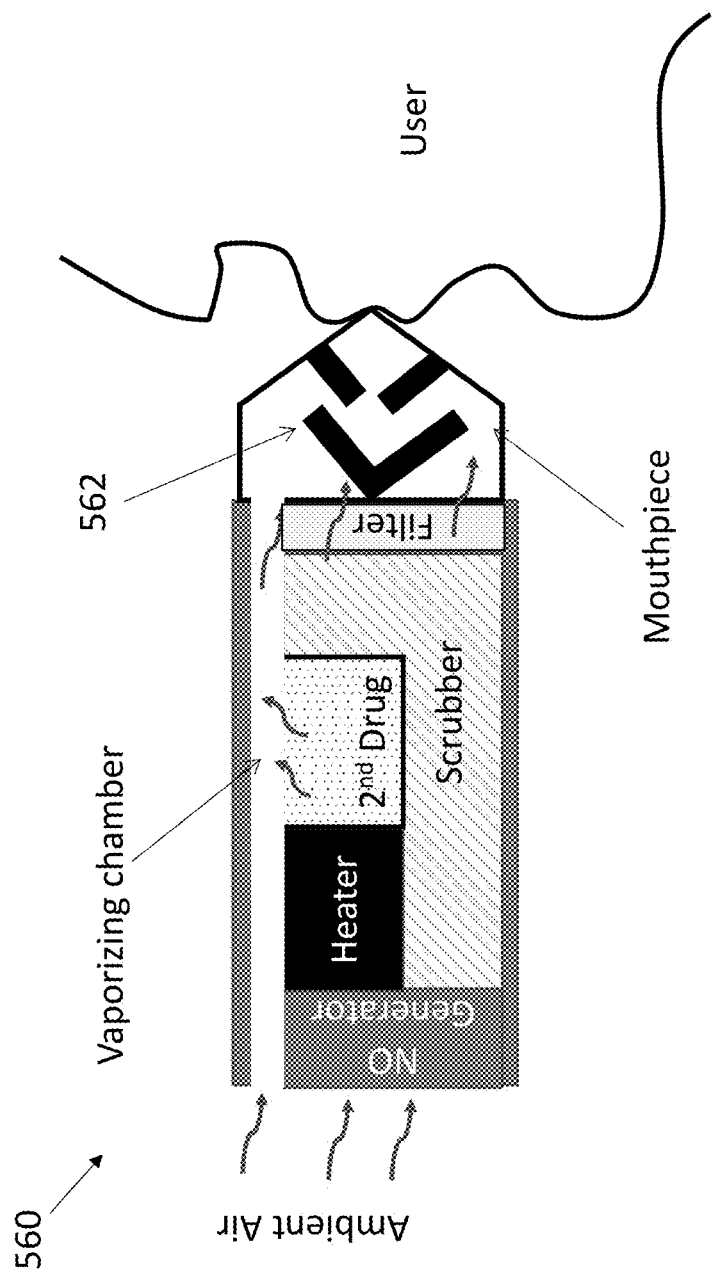
FIG. 30B illustrates an exemplary embodiment of a two-drug delivery device where drug flow paths are kept separate until the mouthpiece.

FIG. 30A depicts another embodiment of an inhaler device 550 in the form of a drug combination delivery device. In this embodiment, the secondary drug can be heated using a heater 552 to become a vapor and drawn into the user inspiratory flow. Part or all of the air inspired by the user passes through a NO generator 554 and a scrubber 556 before passing through a vaporization chamber 558 of the secondary drug and on to the user. Independent control of the NO generator and heating element enable the combination drug delivery device to deliver the two drugs according to independent delivery schedules within or between breaths. In some embodiments, the inhaled NO levels are up to 20 or 40 ppm. In some embodiments, inhaled NO levels are up to 100 ppm. In some embodiments, the inhaled levels are up to 1000 ppm, mimicking the inhaled NO levels from a cigarette. In some embodiments, a filter is utilized to remove particles from the NO generator and scrubber (not shown). In some embodiments, the scrubber, filter and secondary drug are packaged and disposed of separately. In some embodiments, one or more disposable elements of the system are packaged together. In some embodiments, the entire system is disposable. FIG. 30B depicts a similar embodiment of an inhaler device 560 where NO-containing gas and a vaporized secondary drug are kept separated until they enter the mouthpiece. In this embodiment, static mixers 562 are utilized in the mouthpiece to homogenize the gas mixture before it enters the user.

Figure 31:
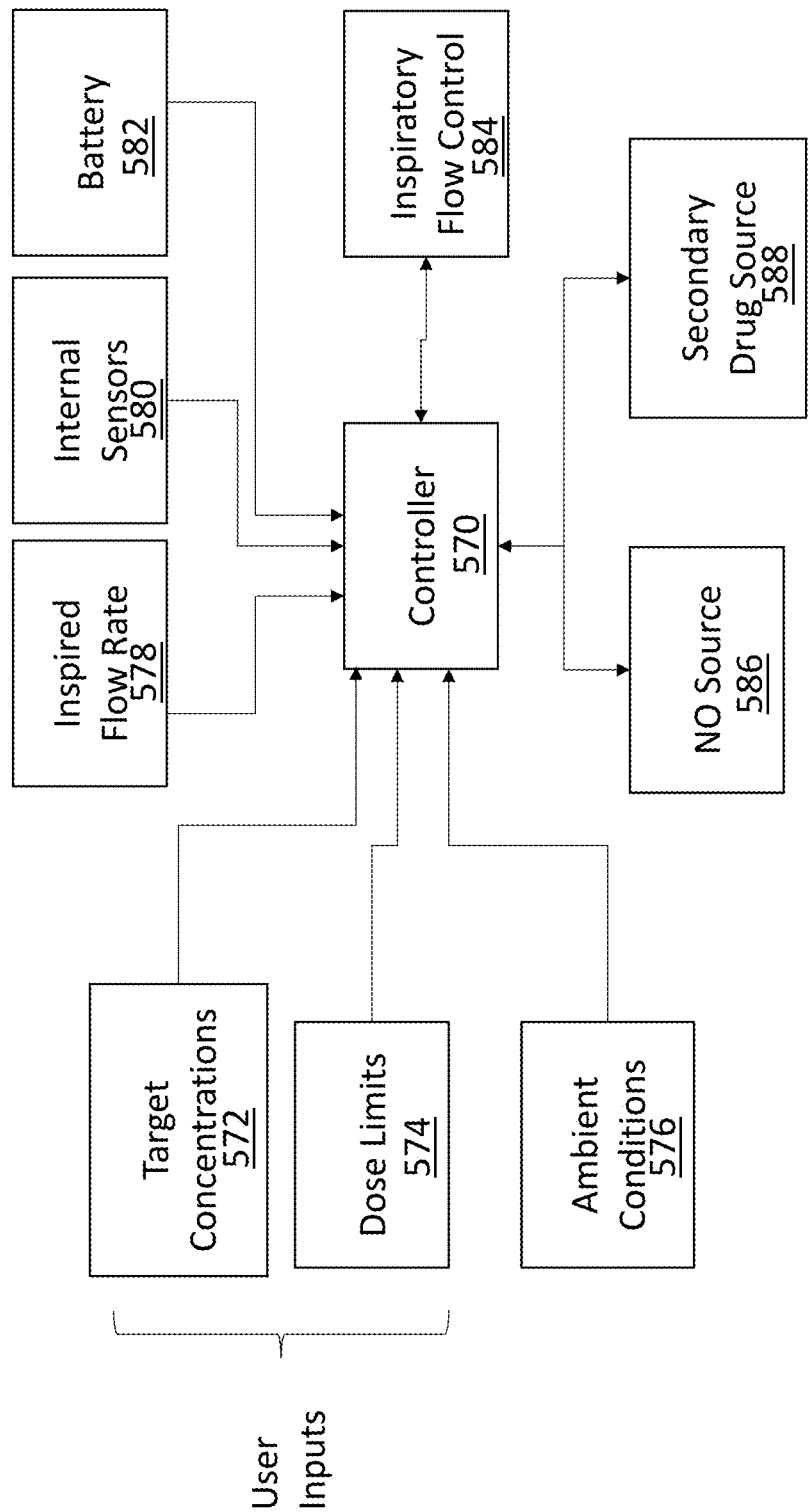
FIG. 31 depicts an exemplary embodiment of an architectural block diagram of a two-drug delivery device.

FIG. 31 depicts an exemplary embodiment of a block diagram of the control architecture for a two-drug delivery device. FIG. 31 depicts a single controller/microprocessor 570, however the tasks may be distributed across more than one controller. In some embodiments, there is more than one controller for safety/redundancy. In some embodiments, the controller receives target treatment conditions 572 and safety limits 574 from a user. In some instances, the user is the recipient of the drugs and in other instances the user is a clinician. In some embodiments, the controller reads the target dose and dose profile from the drug source (e.g., reading from a memory device on a cannister that contains the drug or drug source material. The controller also monitors ambient conditions 576 (e.g., pressure, temperature, humidity) through one or more sensors. The ambient conditions are utilized to derive an air density for determining inspired mass flow in some instances. In other instances, the water content of the inspired air (a parameter that can be measured directly or derived from a relative humidity measurement) is utilized to understand the potential for condensation within the system (e.g., from compression of gas or introduction of cold gas released from a pressure vessel). The controller utilizes one or more sensors to measure the inspiratory flow rate 578. In some embodiments, the controller also measures the pressure within a plasma chamber as an input to the NO generation algorithm using one or more internal sensors 580. Various parts of the system, including the controller, utilize power from either an internal source, such as a battery 582, or external source. In some embodiments, the controller also manipulates the flow resistance within the inspirator gas flow path to modulate the inspiratory flow rate with inspiratory flow control 584. The controller controls the NO source 586 and second drug source 588 and may receive feedback from those functions as well. For example, in one embodiment that delivers a pressurized gas, the controller controls a valve that releases the gas and measures the pressure of the source of gas with a pressure sensor.

In some embodiments of a combination a NO generator/vaporization device, heat from the plasma chamber is utilized at least in part to elevate the heat of the vaporized drug. In some embodiments, the plasma chamber and vaporization chamber share a wall so that heat from the plasma chamber is conducted through the wall to the drug to be vaporized. The temperature of the drug to be vaporized is measured with a temperature sensor (e.g., IR sensor, thermocouple, thermistor, etc.). Supplemental heat energy can be added through a heating device (e.g., resistive heater, thermoelectric, etc.) to achieve a target temperature for drug vaporization.

Figure 32:
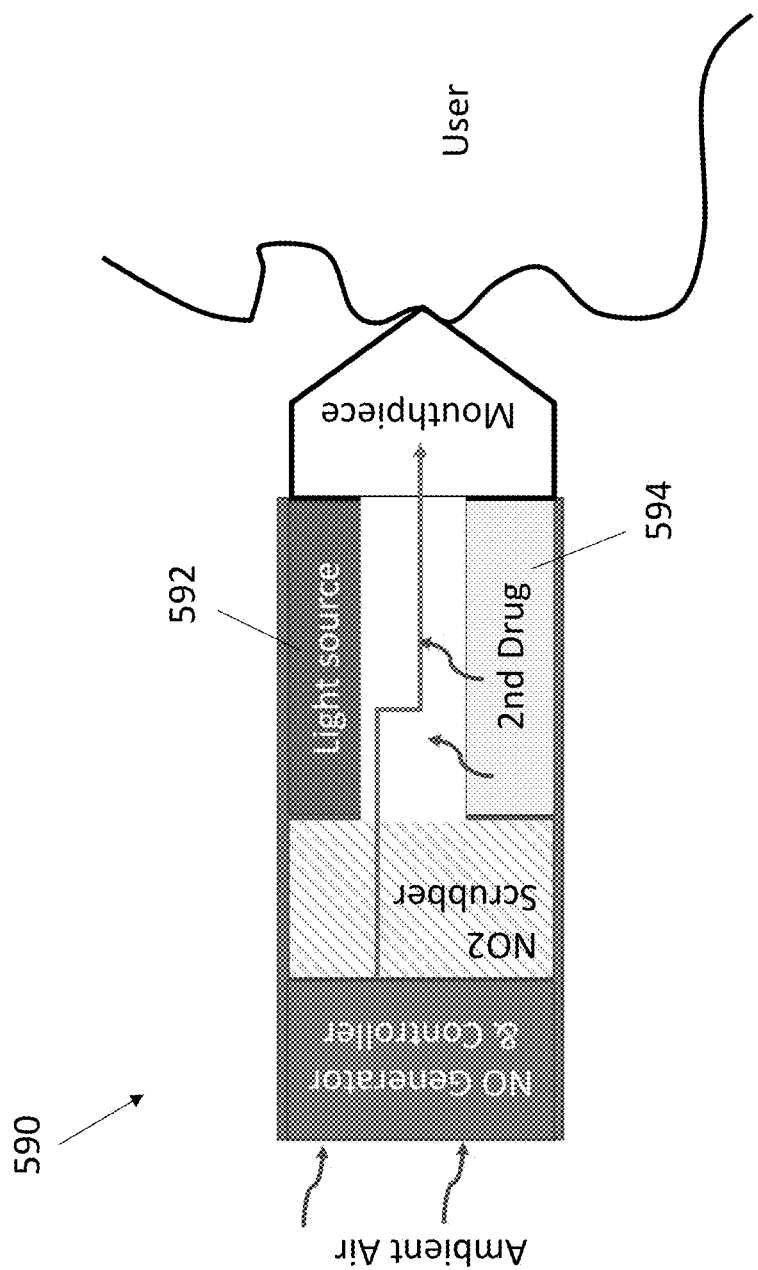
FIG. 32 illustrates an exemplary embodiment of a two-drug delivery device where the second drug is released with a photochemical process.

FIG. 32 depicts an embodiment of an inhaler device 590 where the secondary drug is released using a photochemical process. A light source 592 above a chamber 594 containing the secondary drug is modulated to vary the amount of the secondary drug released into the inspiratory stream. The inspiratory stream is generated by the user pulling ambient air through the NO generator and system. In some embodiments, NO is generated from a photochemical process (not shown). Photochemical processes are controlled by a treatment controller that modulates the light output to control drug release. The device is typically programmed with a drug release profile that is a function of one or more of duration of exposure, light intensity, material temperature, gas pressure, age of photochemical material, and other factors. In some embodiments, a sensor downstream of the drug source is utilized to measure the amount of drug generated and enables closed-loop control of drug release. In some embodiments, the light source is controlled using a pulse-width-modulated signal. In some embodiments, light source is controlled by modulating the supply of voltage and/or current.

In some embodiments of a photochemical release process, the area of photochemical material exposed to light is controlled and the light intensity is unchanged. In some embodiments, a window permitting light through to the surface moves across the surface of the photosensitive material at a controlled rate, releasing a controlled amount of drug. In some embodiments, a laser is directed to variable locations on the surface of the photochemical material to release NO from specific locations. In some embodiments, the laser moves in a Cartesian (XY) coordinate frame. In some embodiments, the laser moves in a spiral (polar coordinate frame) on a surface of drug-releasing material. In some embodiments, a sheet of photosensitive material is unspooled and the laser/light source only moves in an X direction (like a dot matrix printer head) to release controlled amounts of drug from the source material. In other embodiments, both the light intensity and light location on the photoreactive material are varied by the controller to modulate drug release. Similar approaches to controlled NO drug release can be achieved with a heated head instead of a laser for materials that release based on temperature.

Independent Drug Delivery Control

Figure 33:
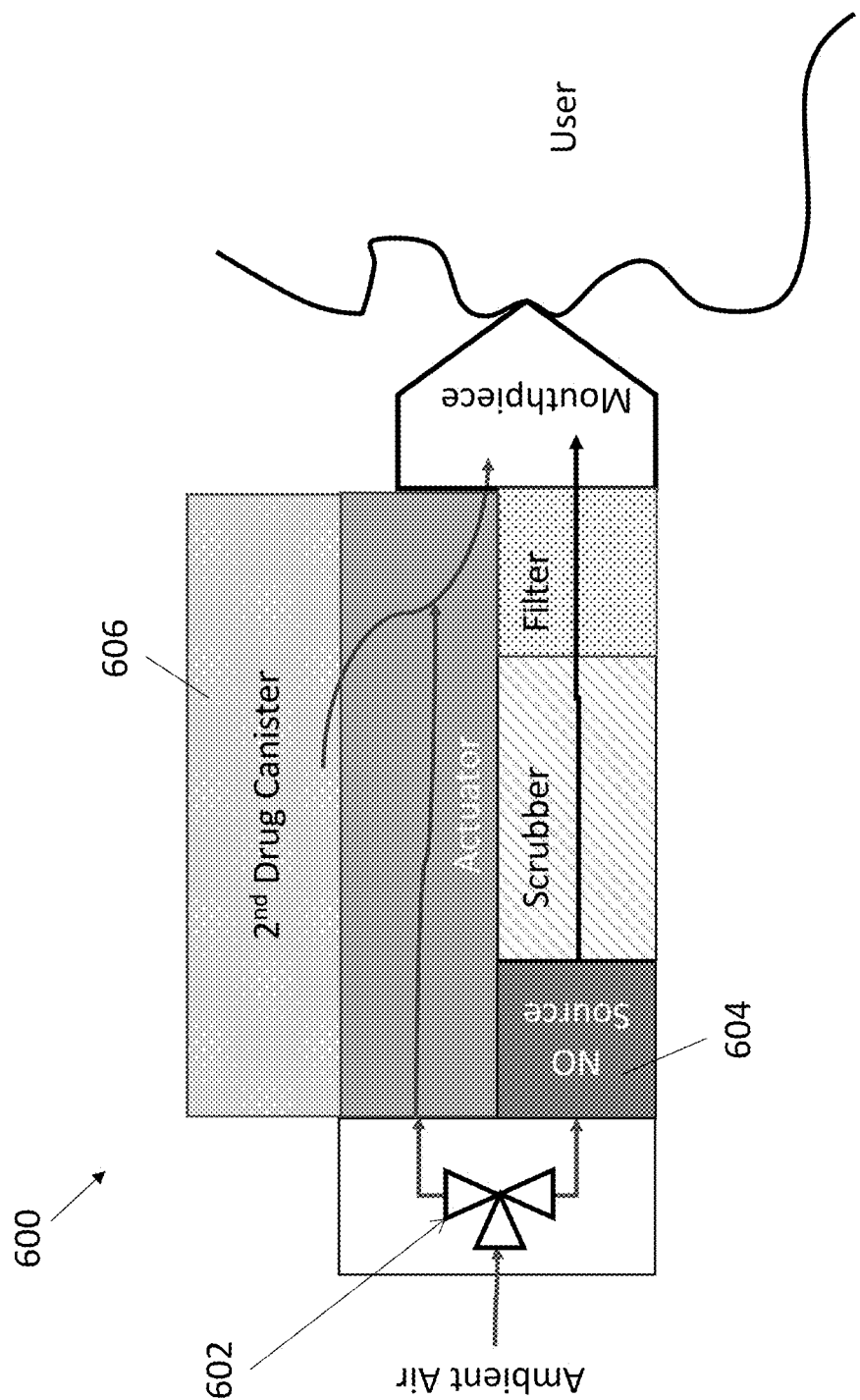
FIG. 33 illustrates an exemplary embodiment of a two-drug delivery device with flow control through the two drug channels.

As the user inhales, some embodiments of the device permit inspiration flow through either the NO flow path or the secondary inhaled drug gas path. This can minimize the potential for reaction between the NO and the other inhaled drug(s). FIG. 33 depicts an embodiment of a two-drug NO delivery device 600 that includes a valve, such as a three-way valve 602 at the inlet that is controlled by the device controller. The valve is positioned to permit the flow of either NO from an NO source 604 or the secondary drug from a cannister 606, or both. In some embodiments, the valve (or combination of valves) can be configured to permit simultaneous flow through both drug channels, or overlap of drug pulses.

Figure 34:
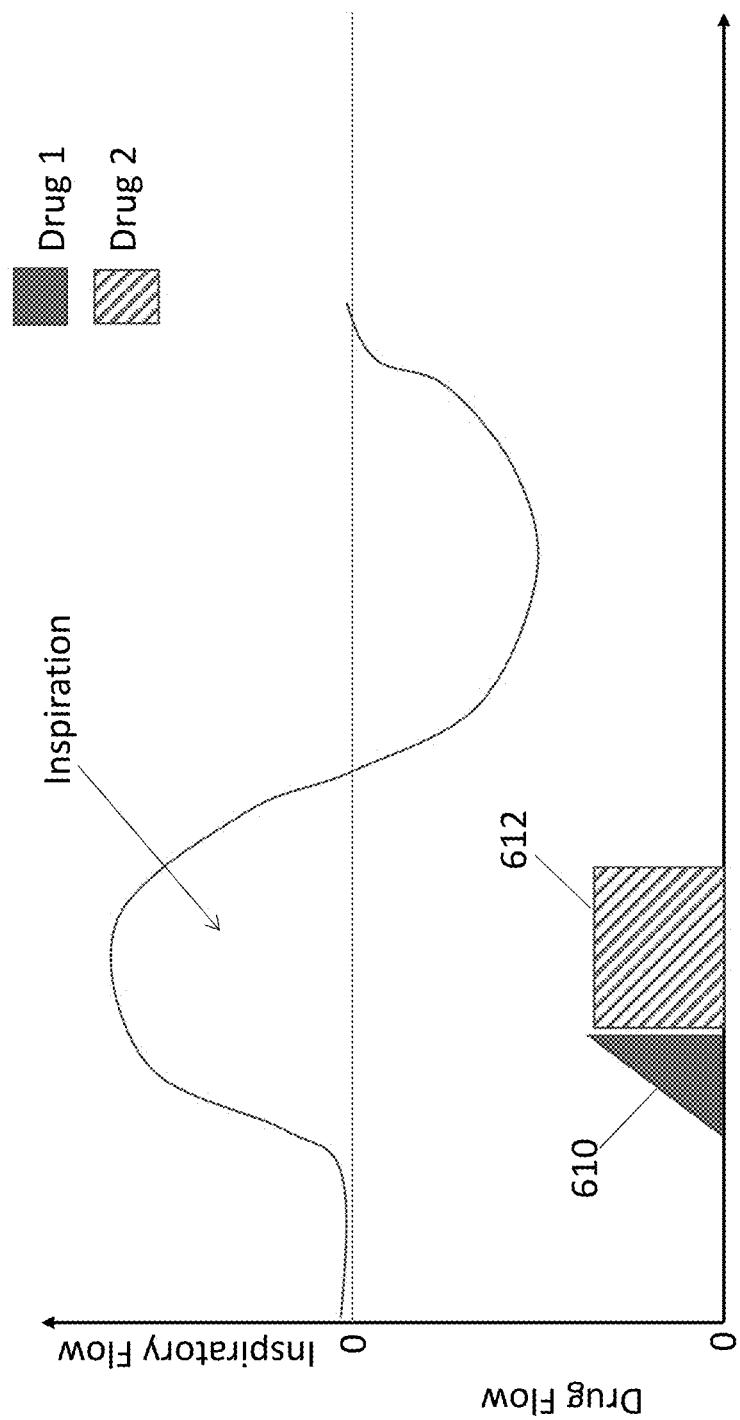
FIG. 34 depicts exemplary sequential dosing of two drugs during a breath.

In some embodiments, the system delivers NO and one or more additional drugs sequentially within a single breath, as shown in the exemplary graph of FIG. 34. A first drug delivery 610 begins either when inspiration is detected or when the user initiates delivery. In some embodiments, the first drug delivery ends after a set amount of time. In some embodiments, the first drug delivery ends after a particular amount of inspired gas has been dosed. In some embodiments, the first drug delivery ends after a target number of molecules of the first drug have been delivered. In some embodiments, the first drug delivery ends after a detected event in the inspiration (e.g., peak inspiratory flow rate or minimum inspiratory pressure). Second drug delivery 612 can begin after the first drug delivery is complete. In some embodiments, the onset of the second drug can be delayed by a particular amount of time. In some embodiments, not shown, the first drug can be dosed again at the end of the breath. It should be clear that the inhaler design proposed can support any sequence and quantity of the first drug, the second drug and/or any additional drug delivery. Furthermore, simultaneous delivery of more than one drug (i.e., overlapping drug delivery profiles) is also performed, as appropriate. In some embodiments, NO is delivered to one or more breaths first to relax the smooth muscle within the patient airway and/or lung followed by delivery of one or more additional drugs.

In some embodiments, the controlled delivery of multiple drugs is managed by more than one, independent controller. In some embodiments, a single controller manages the timing and drug delivery for all drugs. Other permutations are also possible with multiple controllers that share information to share sensor information and coordinate drug delivery. In some applications, the device can deliver one drug without the other.

Figure 35:
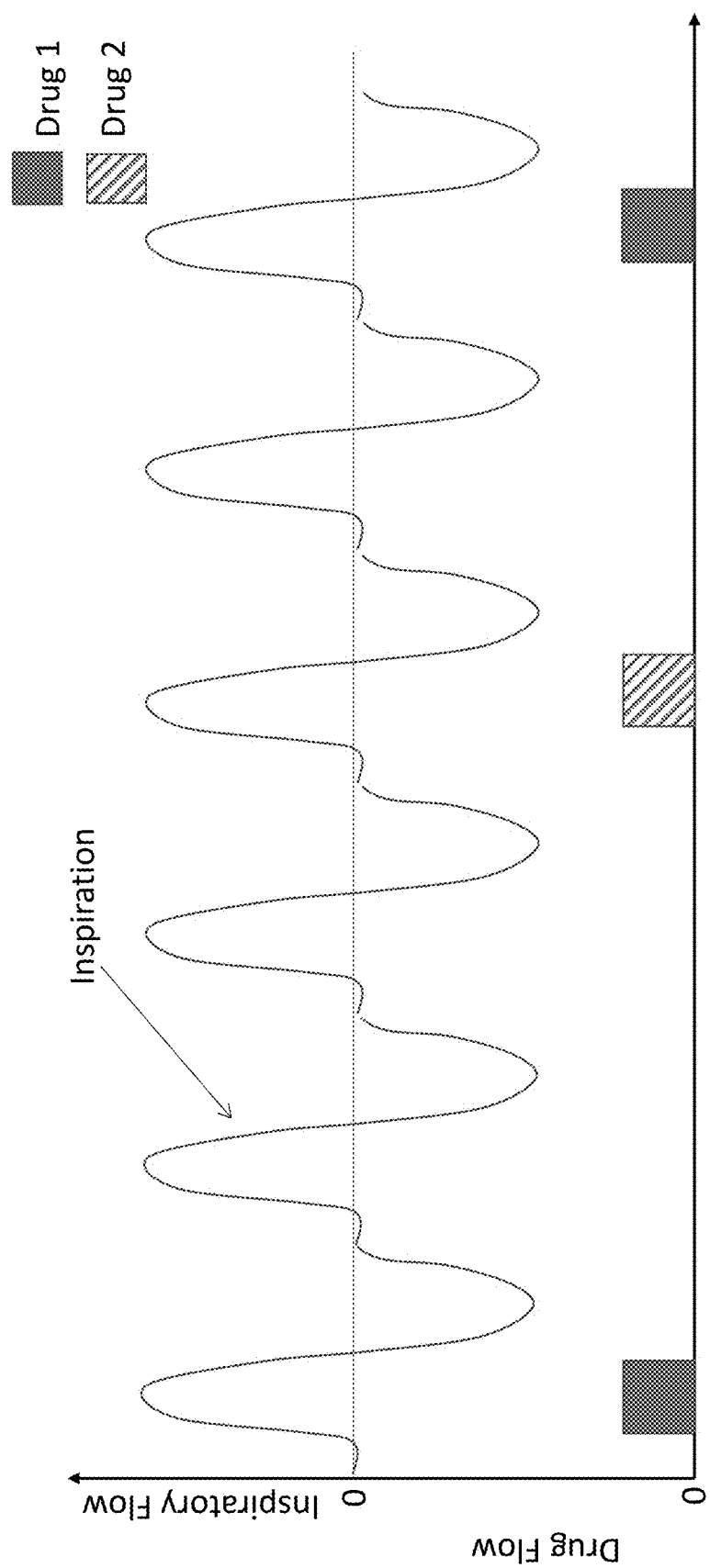
FIG. 35 depicts an exemplary two drug dosing profile for a breathing pattern.

In some embodiments, the device delivers NO, air, and one or more other drugs according to a prescribed pattern. NO is rapidly metabolized, however, one or more breaths with no medication can also be inserted in the treatment pattern when switching between drugs to purge the pulmonary airways and reduce drug to drug interaction further. FIG. 35 depicts an exemplary graph showing a pattern spanning multiple breaths. A first detected breath is dosed with drug 1, followed by two breaths with no drug delivered, followed by drug 2, followed by a breath with no drug and then the pattern repeats. This approach can be valuable when the effect of drug 1 takes time to have an effect and/or when drug 1 and drug 2 are not chemically compatible. The pattern can occur within a breath or across multiple breaths. The pattern of drug delivery can be automatically derived by the device controller, taking into account one or more of the following: the time required to take effect for one or both drugs, the target dose (e.g., mg/hr) of each drug, the minimum/maximum effective amount of each drug to deliver in a pulse, the potential for interaction between the drugs, the portion of the breath/anatomy targeted for dosing, time for a one or both drugs to wear off, the patient breathing pattern (rate, tidal volume, inspiration/exhalation ratio, etc.) as well as other physiologic, treatment and drug-related factors.

Weaning

In some embodiments, an inhaled device can include a weaning feature that decreases the dose delivered of one or more drugs over time. In some embodiments, the amount of drug delivered with each breath is decreased (e.g., lower concentration, shorter pulse). In some embodiments, the device locks out the user for longer and periods of time to increase the time between doses.

Architectures for Multiple Drug Delivery

Figure 36:
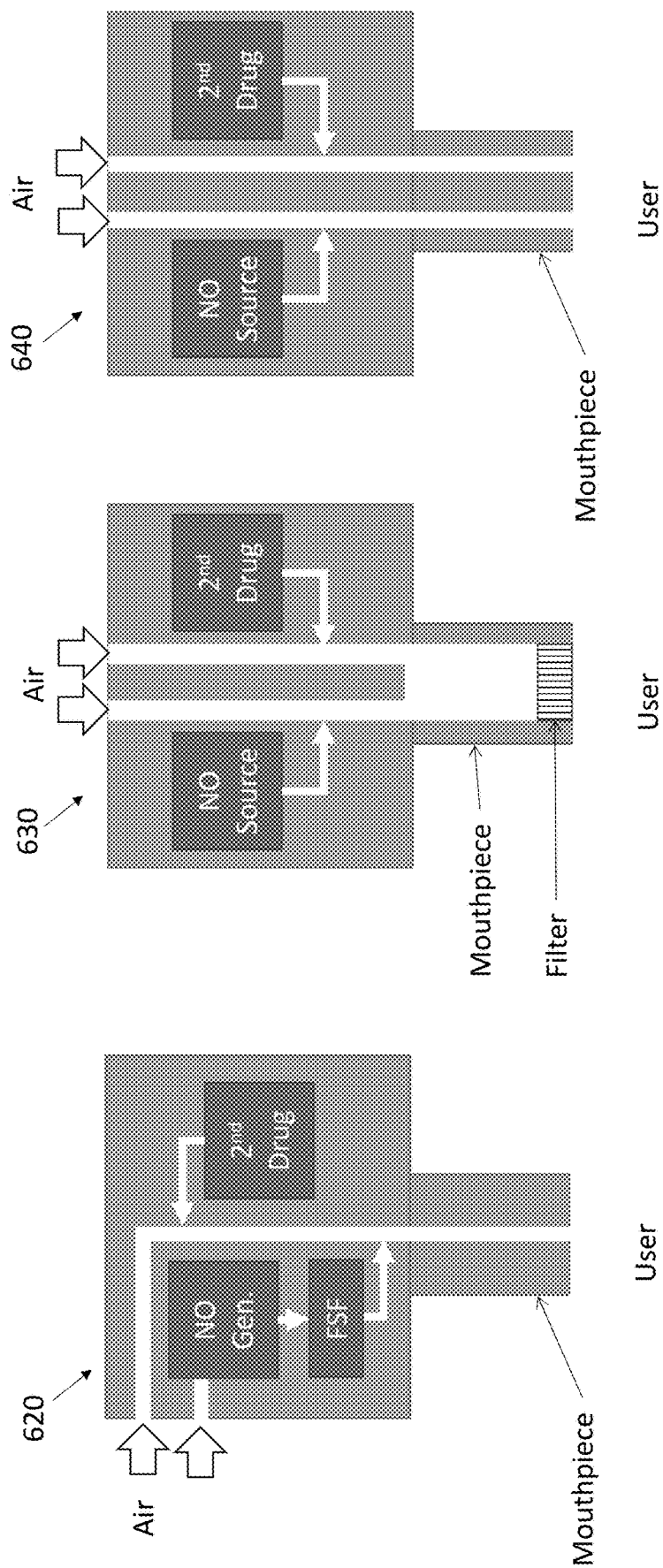
FIG. 36A illustrates an exemplary embodiment of a NO inhaler with NO generation and delivery of a secondary drug.
FIG. 36B illustrates an exemplary embodiment of a NO inhaler with a NO source and a secondary drug source that permits mixing prior to inhalation.
FIG. 36C illustrate an exemplary embodiments of a NO inhaler with a secondary drug delivery that isolates NO from the secondary drug within the device.

In some embodiments, NO is delivered simultaneously with another inhaled drug. In some embodiments, the other inhaled drug is a gas at room temperature (e.g., oxygen, helium, nitrous oxide). In some embodiments, the other inhaled drug is a liquid at room temperature (e.g., albuterol, surfactant, etc.). In some embodiments, the other inhaled drug is a solid at room temperature (e.g., powdered insulin). In some embodiments, NO is introduced to an inspiratory gas stream in series with an additional inhaled drug source (i.e., both drugs are introduced into a common flow path), as depicted in an embodiment of an inhaler device 620 show in FIG. 36A. FIG. 36A depicts NO being introduced after the second drug. This approach works well for NO sourced from cannisters and or electric NO generated from a separate air source, as shown in the figure. The air path to NO source shown in FIG. 36A and any filters and scrubber are not required for NO sourced from cannisters. In some embodiments, introduction of NO to the inspiratory flow after the second drug can shorten the transit time of NO (to minimize NO2 levels) and decreases the exposure time of the second drug with NO. In some embodiments, a final filter (not shown) filters the combined gas stream before it enters the use.

In some embodiments, NO and the additional inhaled drug are delivered to two separate inspiratory flow paths that merge within an embodiment of an inhaler device 630 as shown in FIG. 36B. A filter within the mouthpiece filters the merged flow prior to delivery to the user. In some embodiments, the two separate flow paths exit the mouthpiece independently (separate lumens) so that the flows merge within the user, as shown in an embodiment of an inhaler device 640 shown in FIG. 36C.

Figure 37:
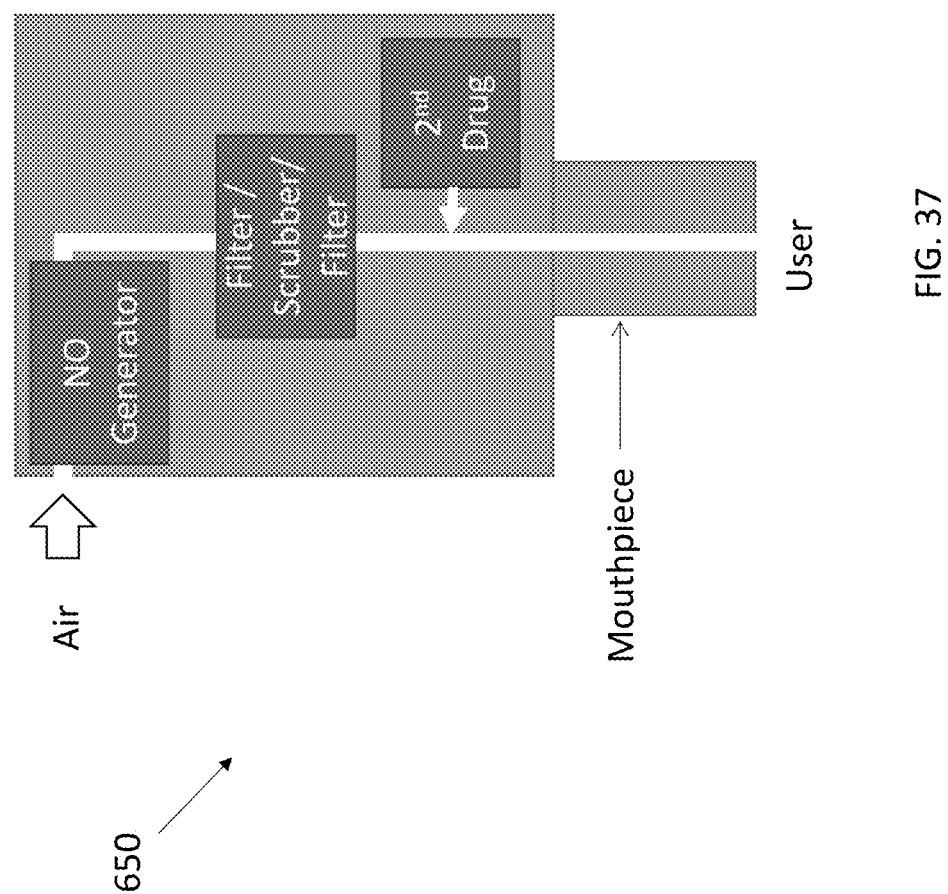
FIG. 37 illustrates an exemplary embodiment of a combined NO generation and second drug delivery system with upstream NO generation.

In some embodiments of an inhaler device 650 as shown in FIG. 37, NO is generated in the main inspiratory stream. In this case, the second drug can be introduced after NO generation to avoid passing the second medication through a plasma chamber since that could denature the second drug and contaminate the plasma chamber. Similarly, the second drug is typically introduced after the scrubber component to prevent interaction between the second drug and the scrubber material.

Battery Charging

A NO inhaler device can be recharged from an external power source. In some embodiments, the inhaler device includes an external electrical connection (e.g. USB, car cigarette lighter, etc.). In some embodiments, a NO inhaler is inductively charged from an external power source. In some embodiments, a charging stand is used with a NO inhaler. The charging stand facilitates establishing the charging connections, be they electrical or wireless (inductive). In some embodiments, the electrical charging interface is USB. In other embodiments, charging pads are on the surface of the inhaler device and register contact with the charging stand when the device is nested into the charger. In some embodiments, the electrical charging connection is covered by a boot or other component to prevent fluid and particulate ingress.

Data

In some embodiments, the NO inhaler device collects and stores use data. Data can be uploaded to and downloaded from the NO inhaler device using either wired or wireless means. In some embodiments, the charging connection is used to transfer data to and from the device. Examples of user data collected include but are not limited to inspiratory flow profiles (time & flow rate), and breath volume. Examples of treatment data collected include dose frequency, average dose level, cumulative drug delivered, and time and date of use events. Examples of device data collected include type and time stamp for any alarms, battery level, and serial number of disposables used.

Disposable Design

The disposable element houses components that are exhausted at a faster rate than components in the main device. In some embodiments, the replaceable component includes one or more of the following: (1) a reactant gas filter, for example a simple inlet filter to prevent access to electrodes and initial particulate blocking (e.g., 20 micron); (2) a NO source, such as an electrical discharge plasma chamber, microwave cavity or bottle/container of NO, that when disposable, can be made of less expensive, shorter-lasting materials (for example, electrical discharge electrodes could be constructed from stainless steel, steel, and tungsten); (3) NO2 abatement material (e.g., soda lime, TEMPO, metal organic framework (MOF), ascorbic acid); (4) a product gas particle filter for electrode and/or scrubber particulate, such as a HEPA filter (e.g., 0.22 micron); (5) at least one memory device (e.g., EEPROM, RFID) containing at least some of usage tracking, dose level which may include target tidal volume to use for dosing, drug concentration (e.g. in a drug cannister), and operating life info, including but not limited to expiration information, number of puffs left, use expiration time, lot number, and binary information on whether or not the scrubber has been inserted in the device; (6) desiccant material to remove moisture from gas (e.g. the ambient air prior to plasma generation of NO), which in some embodiments, this is done to improve dose control since production errors as great as 40% can be attributed to humidity effects, and in some embodiments, moisture is removed to prevent condensation within the device that may occur with increased pressure or decreased temperature, depending on the design; and (7) one or more one-way valves (e.g., flapper, ball in socket, duckbill, reed) that can ensure that flow through the device is unidirectional and prevents exhaled gases from entering the device, and valves also protect the disposable from humid ambient air and exhaled gases when the device is not in use.

Reusable Component Design

A reusable portion of the system can include one or more of the following components: a battery (e.g., rechargeable battery, alkaline battery, etc.), a critical orifice to regulate maximum flow, a dose adjustment (knob, slider, numerical input, etc.), and a user interface. The user interface can include at least some of indicators for when to take next dose based on disposable data, current dose setting, time until next dose, history of doses for n days, flow rates achieved during dosing, and/or dose level history.

A flow sensor (e.g., delta pressure sensor, hot wire, etc.) can also be part of the reusable portion of the system. In some embodiments, the flow sensor is used to determine when max flow was achieved. In some embodiments, the flow sensor is used to determine the direction of gas flow through the device (inhalation vs. exhalation). In some embodiments, the flow sensor is used to measure inspiratory flow for the controller to determine the appropriate NO flow rate. In some embodiments, a flow sensor is utilized to measure NO gas flow. This can be done to confirm proper function or as an input into a flow control mechanism.

Another component that can be part of the reusable portion of the system can be electronics for producing NO, managing disposable components, managing indicators, reading sensors and managing the battery, and/or storing information (memory). In some embodiments, indicators include one or more of lights, vibratory motors, buzzers, and speakers. In some embodiments, the electronics are hardware only. In some embodiments, the electronics include a software-controlled microprocessor or FPGA. In some embodiments, the controller keeps track of device usage and compliance logging.

Mouthpiece

In some embodiments, the mouthpiece is integrated into the housing. In some embodiments, the mouthpiece can be removed to allow users to replace it as it gets worn or dirty.

In some embodiments, the mouthpiece is integrated into the disposable portion of the system to ensure frequent replacement. The mouthpiece serves as the connector between NO gas pathway and user. It is sized so that the user can easily make a seal around it and draw the gas flow rate through it.

Reusable Device Features

In some embodiments, the reusable main body can include a user interface that includes a display that indicates the dose setting and buttons that enable a user to enter information. The buttons may be hardware buttons or software buttons on a touch screen. In some embodiments, the inhaler device user interface is provided in an app running on an external device. In some embodiments, the user interface for the inhaler consists of an app on a cell phone. Information is entered into and viewed through the cell phone app and the cell phone wirelessly communicates settings and other information to the NO device. In some embodiments, the user enters one or more of a password for device use, the time of day, the desired dose schedule, doctor phone number, lung volume, inhalation flow rate threshold values, type of disposable, type of electrodes, and other information.

Exemplary Use Steps

The following are exemplary steps that can be taken to use a NO inhaler device:
1) User inserts disposable mouthpiece
2) Device to disposable communication—periodically or upon insertion
   a. Determine if it has already been used—Alert user, disposable must be replaced
   b. Determine if it has expired—Alert user, disposable must be replaced
   c. Determine if maximum number of doses delivered has been reached—Alert user, disposable must be replaced
   d. Read Dose setting
   e. Device sets disposable use status upon insertion
      i. Used flag
      ii. Initiate timer to expire
   f. In some embodiments, if battery completely discharges and system starts from cold, it requires any disposable already inserted to be discarded.
3) User fully exhales into the atmosphere to empty their lungs.
   a. This is done in some embodiments to enable the system to provide a more even dose throughout the lung without relying on diffusion-based mixing in the lung.
4) User inhales NO gas from the device
   a. In some embodiments, the device generates NO in proportion to the flow rate through the device, as indicated by the flow sensor or pressure measurement as a proxy for flow. In another embodiment, when the flow reaches the governed flow rate, as dictated by a flow restriction (e.g., critical orifice) and indicated by the flow indicator, the device doses the flow to the appropriate NO concentration
   b. When the flow drops below a particular threshold flow level, dosing stops to ensure no residual NO is left and all NO2 is cleared.
5) Device sets disposable information, for example, including an increment use count Safety Features In some embodiments, the NO inhaler is used like a typical inhaler or nebulizer. In some embodiments, the level of NO dosing is prescribed by a physician. In other embodiments, NO delivery is controlled by a user but is limited in some embodiments for safety reasons to control risk of underdosing and overdosing.

In some embodiments, the device prevents subsequent use for a period of time. In some embodiments, the system can prevent use while the device is charging. Some embodiments prompt replacement of the disposable components after a certain amount of use (e.g., n treatments, or n moles of NO gas delivered). For example, a device can be prescribed to deliver 200 ppm to a breath every 10 minutes. Treatment begins when the user inhales their first breath of 200 ppm NO. The device waits a period of time, for example 10 minutes, before permitting the user to receive another dose of NO. In some embodiments, the component including NO2 scrubber material is replaced after a set amount of time, independent of level of use. In some embodiments, replacement occurs because the scrubber material is in contact with air and will become exhausted from exposure to atmospheric carbon dioxide.

In some embodiments, the device alerts the user when it is time to inhale another breath. The notice can be in the form of an audible sound, visual indicator (e.g., light, user interface message), a vibration, a phone call, a text message, or other means to get the attention of the user. In some embodiments, the alert is delivered through an external device (e.g., cell phone).

In some embodiments, user dosing is stored in the cloud to prevent users from owning and using multiple devices in order to receive more than a safe amount of NO. NO delivery devices check with a database in the cloud prior to treating the user to ensure that sufficient time has elapsed since the last NO dose.

In some embodiments, a fingerprint recognition device is utilized to confirm that the correct user is utilizing the device.

In some embodiments, the device disables drug delivery when the mouthpiece is not installed. This protects the user from high voltage and/or chemicals involved with NO generation in some embodiments.

In some embodiments, the inhaler includes a drop-detection component that actively or passively disables the device. In some embodiments, a drop-detection sensor informs the device controller that a high-acceleration event has occurred. Some NO devices are intentionally disabled form further user after detection of a drop to protect the user from risk. Example risks that may present in the event of a dropped device include exposure to high voltage, exposure to inhaled particulate (e.g., damaged filters), and gas leaks resulting in altered dosing.

In some embodiments, two buttons must be pressed to activate drug release to prevent unplanned drug release during handling or transport (e.g., when the device is in a pocket).

In some embodiments, the device is disabled when the scrubber materials have been exhausted or expired. Scrubber exhaustion can be based on one or more of the following: the amount of NO in moles that have passed the through scrubber, the number of breaths that have been dosed with the scrubber, the size of the scrubber, the type of scrubber, and the amount of time the scrubber has been in service. In some embodiments, expiration is based relatively on the date of manufacture or the date the scrubber was first put into service.

User Interface

A NO inhaler device can include a user interface. In some embodiments, the user interface presents information related to one or more of current dose setting, remaining gas supply, battery charge level, remaining breaths that can be dosed, fraction of breaths dosed, count of breaths dosed, alarm sound level, alarm mute. In some embodiments, the user interface is located on an external device (e.g., cell phone, tablet computer, etc.). The user interface can also include settings that can be adjusted but the User and/or clinician. In some embodiments, the adjustable treatment parameters include NO dose, inhaled volume, secondary drug dose, dose pattern with respect to breaths, target NO concentration, target NO molecules per breath, target NO molecules per unit of time, maximum number of breaths to dose in an amount of time, NO pulse delay (e.g., time from breath detection event).

Applications

Infection Prevention/Treatment

In some embodiments, a user is prescribed NO to treat and/or combat and/or prevent pulmonary infection. Example indications include viral infections (e.g., COVID, SARS), bacterial infections (e.g., pneumonia), and fungal infections. In some embodiments, a physician prescribes a particular dose to be administered a certain number of breaths a certain number of times per day. The clinically necessary concentration to treat a particular infection varies with infection type and degree. Current literature suggests concentrations of 200 too 1000 ppm NO may be necessary for some infections. Regardless of the clinically-necessary concentration, the NO delivery device can be sized appropriately to deliver the required quantity of NO.

Figure 38B:
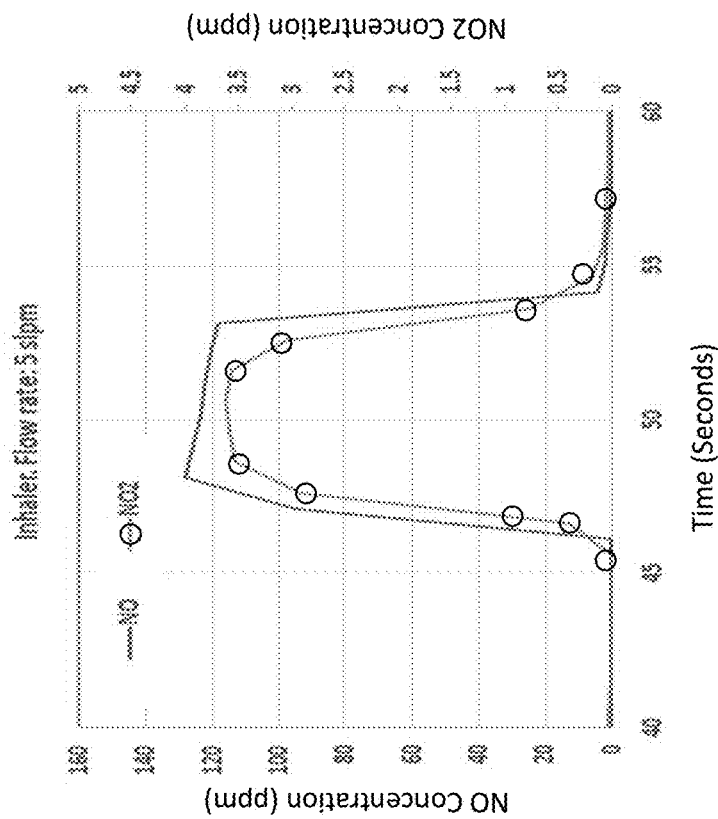
FIG. 38A and FIG. 38B depict embodiments of NO pulse delivery performance of an exemplary electric NO generation inhaler.
Figure 38A:
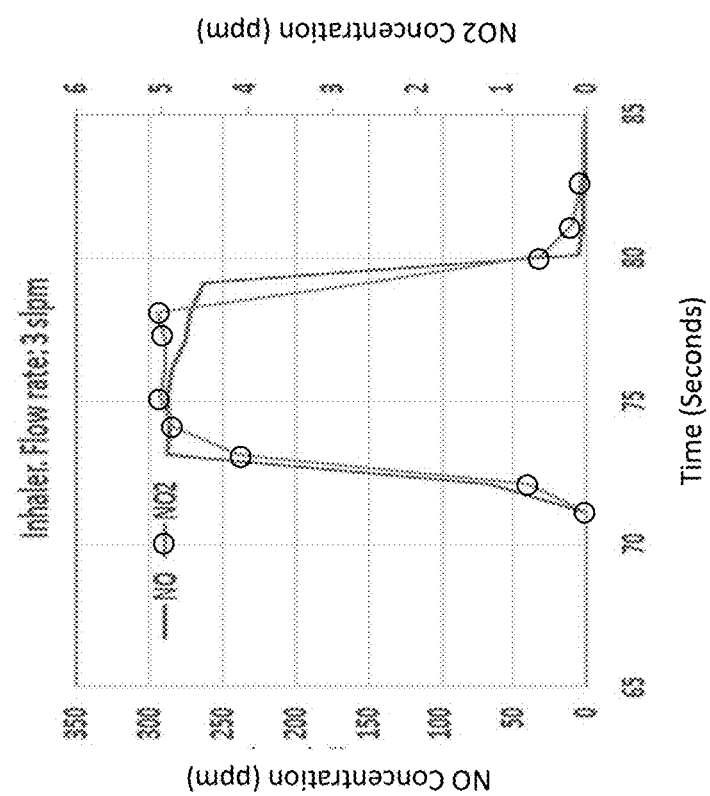

FIGS. 38A and 38B depict exemplary graphs showing the NO delivered from a NO generation and delivery device for two flow rates, 3 slpm (FIG. 38A) and 5 slpm (FIG. 38B). The plot in FIG. 38A demonstrates NO production of 750 ppm·lpm (250 ppm*3 lpm). The plot in FIG. 38B shows another device generating 600 ppm·lpm (120 ppm*5 lpm) at a higher flow rate. NO2 levels are 5 ppm or less, which complies with OSHA permissible exposure limit (PEL) for air. Lower NO2 levels can be achieved by higher gas flow rates (less transit time), higher NO/NO2 ratio, and additional scrubbing (larger scrubber).

Asthma Treatment

In some embodiments, a user utilizes the NO inhaler device for treatments of asthma on an as-needed basis. When the user experiences asthma conditions or precursors to asthma conditions, NO treatment is administered to mitigate the conditions.

Nasal Cavity Treatment

In some embodiments, the inhaler interfaces with the patient nose (e.g. prongs, partial mask). NO gas is introduced to the nasal cavity of the patient to treat infection. In some embodiments, the patient inhales through their nose. In some embodiments, the patient holds their breath so that the NO gas resides in the nasal cavity at higher concentration.

Figure 39:
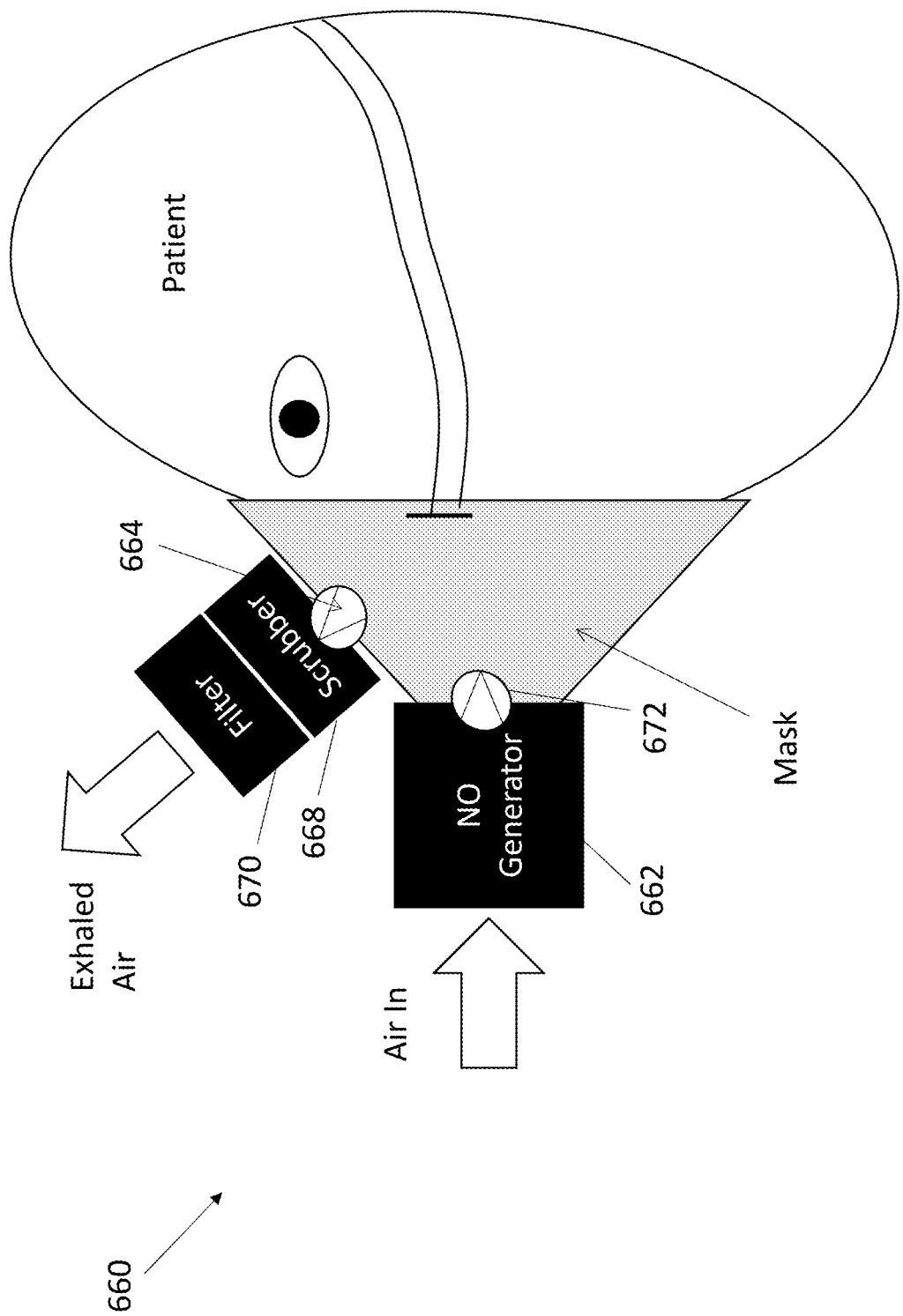
FIG. 39 depicts an exemplary embodiment of a NO generation mask.

FIG. 39 depicts an embodiment of a NO generation mask 660. The mask can be held to the patient's head with one or more elastic bands. The patient draws ambient air in through a NO generation device 662 (e.g., electric discharge, microwave, N2O4, photochemical, etc.). The inhaled gas enters through one or more of the mouth and nose. The patient exhales out of one or more of the mouth and nose. Exhaled gases exit through a one-way valve 664 (e.g., flapper, ball, check, duckbill) and through a NO2 scrubber 668 and a filter 670 prior to release into the atmosphere. A check valve 672 at exit of the NO generator ensure that exhaled gases do not exit through the NO generator. In the depicted embodiment, the NO generator is self-contained and includes the NO source, inspiratory flow sensing, ambient gas measurement, controller, and power (e.g., battery) required to generate the desired dose of NO to the inspiratory flow.

An NO generation mask can be programmed to provide a variety of treatments. In some embodiments, the NO generation mask is utilized to maintain blood vessel dilation within a target region of the nasal sinus, mouth, airway and/or lung. Given the physiologic half-life of NO being tens of seconds, the NO generation device is not required to dose every breath in all applications. In some embodiments, the NO generation mask is programmed to deliver a high concentration of NO (e.g., 400 ppm) with every breath to maintain a bactericidal, fungicidal or virucidal concentration within the patient to treat an infection.

Inhaled Drug Enhancement

A NO inhaler device can be coupled with a device with inhaled drug delivery to facilitate more effective drug uptake due to NO vasodilation and increased blood flow through the pulmonary vasculature. This method can increase the level of drug delivered, improve drug effectiveness, and reduce drug waste during delivery. Use of NO, a relatively inexpensive drug, in concert with a more expensive drug can decrease the overall cost of treatment when the level of expensive drug required is reduced.

Performance Enhancement

In some embodiments, a NO inhaler device is utilized on an as-needed basis by a user to improve oxygen uptake. Example applications include but are not limited to altitude adjustment/acclimation, $O_2$ loading for sports and fitness, support catching breath during exertion, mountaineering, aviation, and aerobic performance enhancement. In some embodiments, the device delivers a single NO pulse profile with each dose. In some embodiments, the NO device limits the amount of NO delivered over time to prevent overdosing.

Rescue Inhaler

In some embodiments, the NO inhaler is used as a rescue device to relieve hypoxia and reduce PVR during an acute exacerbation stemming from worsening fibrotic and/or obstructive diseases like ILD and COPD. In some embodiments, the NO device is used to improve cardiac output in patients in an ambulance that suffer from a myocardial infarct (MI). This is important because the titration and drip infusion of a systemic vasodilator cannot be initiated in an ambulance.

In some embodiments, a NO inhaler is designed to be single use and disposable. For example, these devices are used for emergency situations and stored in first aid kits, on ambulances, and in emergency rooms. The device is entirely self-contained, including battery, inlet gas conditioner, plasma chamber, NO2 scrubber, filter, enclosure, and processor. In some embodiments, the device includes a battery that can last a long time on the shelf without needing to be recharged (e.g., lithium, lithium ion, alkaline). In some embodiments, the battery chemistry is rechargeable while others utilize a disposable battery chemistry.

In an exemplary use scenario, a patient riding in an ambulance or military transport is hypoxic. A caregiver takes a single use NO generation device out of its packaging and turns the device on by toggling a switch. In some embodiments, the device begins making a constant flow of NO automatically. Other embodiments are designed to detect a respiratory signal from a patient inspiratory limb or other device and deliver pulsed NO during patient inhalation. Some embodiments deliver a continuous stream of NO (e.g., 5 lpm of 20 ppm NO) while other devices deliver pulses of NO only during inhalation.

In some use scenarios, particularly those with a conscious patient, the patient is asked to inhale through the device so that NO can be delivered. In other scenarios, the NO device delivers NO to a nasal cannula or a mask for a patient to inhale. For unconscious patients, the NO device can be attached to a ventilator circuit or manual resuscitator (AKA a bag) to deliver NO either continuously or intermittently with inhalation events.

The device is used until NO is no longer needed or until the battery and/or scrubber is exhausted (e.g., after 1 hour). The device is then discarded into either the normal waste stream or biohazard waste stream, depending on whether or not there was patient contact. In one embodiment, a disposable NO device provides 30 continuous minutes of up to 40 ppm NO to a patient before shutting off.

In some embodiments, single use devices are maintained on a charger until their use.

In some embodiments, a single use NO device alerts the user that it is nearing the end of its service life. This enables the user to prepare a subsequent single-use device prior to exhaustion of the current device in order to provide continuous NO therapy to a patient.

Packaging

In some embodiments, NO inhaler devices are packaged singly. They are packaged in a way that protects them from impact. They are also packaged in a way that protects scrubbing materials from air (e.g., sealed membrane, or bag) to prevent premature exhaustion from atmospheric CO2, environmental VOCs and from dry air. Dry air can dry out some kinds of scrubber materials (e.g., soda lime) to the point that they no longer adequately function. In embodiments that include desiccant for removing ambient humidity and soda lime for removing NO2, the desiccant and soda lime are separated in the packaging via a membrane, cap, or other means to prevent the desiccant from drying the soda lime. In some embodiments, removal of the packaging, sealing component, membrane, or cap provides a signal to a NO inhaler to turn on. In some embodiments, removal of the membrane establishes the battery connection and enables a device to power on.

In some embodiments involving more than one drug, the NO inhaler device and second drug may be packaged together or separately.

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

What is claimed is:

1. A drug delivery system, comprising:
   a housing having a distal end with an inlet through which an inspiratory flow of air passes into the housing, a proximal end having a patient interface attached thereto, the patient interface being configured to interface with a user, and an inspiratory flow pathway extending from the distal end of the housing to the proximal end of the housing;
   a nitric oxide (NO) source positioned within the housing, the NO source configured to deliver NO-containing gas to the patient interface;
   a secondary drug source positioned within the housing, the secondary drug source configured to deliver a secondary drug to the patient interface; and
   a controller configured to control an amount of NO-containing gas delivered from the NO source and an amount of the secondary drug delivered from the secondary drug source using a control scheme, the control scheme having one or more inputs relating to at least one of the NO-containing gas, the secondary drug, the inspiratory flow pathway, and one or more inputs from the user, the controller configured to communicate with one or more sensors configured to collect information relating to the one or more inputs to the control scheme, the controller being configured to utilize the control scheme to deliver the NO-containing gas and the secondary drug in a treatment pattern such the controller is configured to switch between delivery of the NO-containing gas, delivery of the secondary drug, and delivery of a gas without the NO-containing gas or the secondary drug to purge the inspiratory flow pathway,
   wherein the treatment pattern is derived by the controller using information related to at least one of a potential for interaction between the NO-containing gas and the secondary drug and a time for the NO-containing gas to wear off.

2. The drug delivery system of claim 1, wherein the patient interface is configured to receive the NO-containing gas from the NO source and the secondary drug from the secondary drug source simultaneously.

3. The drug delivery system of claim 1, wherein the NO-containing gas is configured to increase uptake of the secondary drug.

4. The drug delivery system of claim 1, wherein a dose of NO-containing gas is in a range of 1 to 80 ppm.

5. The drug delivery system of claim 1, wherein a dose of NO-containing gas is in a range of 1 to 1000 ppm.

6. The drug delivery system of claim 1, further comprising a vaporization chamber configured to heat the secondary drug to vaporize the secondary drug.

7. The drug delivery system of claim 1, further comprising a nebulization chamber configured to nebulize the secondary drug.

8. The drug delivery system of claim 1, further comprising one or more of a pressure regulator and a valve to control the flow of secondary drug from the secondary drug source, the secondary drug source being in the form of a pressurized container.

9. The drug delivery system of claim 1, wherein the controller is configured to control the amount of the secondary drug delivered from the secondary drug source.

10. The drug delivery system of claim 1, wherein the controller is configured to deliver the NO-containing gas and the secondary drug using first and second independent delivery schedules.

11. The drug delivery system of claim 1, wherein the NO source comprises a compressed gas cylinder.

12. The drug delivery system of claim 1, wherein the NO source comprises an electric NO generator.

13. The drug delivery system of claim 1, wherein the NO-containing gas is generated from heating N2O4 to make NO2 gas and reducing the NO2 gas to NO with a reducing agent.

14. The drug delivery system of claim 1, further comprising at least one of a scrubber configured to remove NO2 from the NO-containing gas and a particle filter configured to remove contaminants from the NO-containing gas.

15. The drug delivery system of claim 1, wherein the NO-containing gas is delivered from the NO source directly to the patient interface.

16. The drug delivery system of claim 1, wherein the NO-containing gas is delivered from the NO source to the patient interface via the inspiratory flow pathway.

17. The drug delivery system of claim 1, wherein the secondary drug is delivered from the secondary drug source directly to the patient interface.

18. The drug delivery system of claim 1, wherein the secondary drug is delivered from the secondary drug source directly to the patient interface via the inspiratory flow pathway.

19. A drug delivery system, comprising:
- a housing having a distal end having an inlet through which an inspiratory flow of air passes into the housing, an inspiratory flow pathway, and a proximal end having a patient interface attached thereto, the patient interface being configured to interface with a user;
- an electric nitric oxide (NO) generator positioned in the housing and configured to generate NO-containing gas in a plasma chamber with one or more pairs of electrodes therein by ionizing at least a portion of the inspiratory flow of air through the plasma chamber;
- a secondary drug source positioned in the housing and configured to provide a secondary drug; and
- a controller configured to control an amount of NO-containing gas delivered from the electric NO generator and an amount of the secondary drug from the secondary drug source using a control scheme, the control scheme having one or more inputs relating to at least one of the NO-containing gas, the secondary drug, the inspiratory flow of air, and one or more inputs from the user, the controller configured to communicate with one or more sensors configured to collect information relating to the one or more inputs to the control scheme, the controller being configured to utilize the control scheme to deliver the NO-containing gas and the secondary drug in a treatment pattern such the controller is configured to switch between delivery of the NO-containing gas, delivery of the secondary drug, and delivery of a gas without the NO-containing gas or the secondary drug to purge the inspiratory flow pathway,
- wherein the treatment pattern is derived by the controller using information related to at least one of a potential for interaction between the NO-containing gas and the secondary drug and a time for the NO-containing gas to wear off.

20. The drug delivery system of claim 19, wherein the patient interface is configured to receive the NO-containing gas from the NO generator and the secondary drug from the secondary drug source simultaneously.

21. The drug delivery system of claim 19, wherein the NO-containing gas is configured to increase uptake of the secondary drug.

22. A drug delivery system, comprising:
- a housing having a proximal end having a patient interface attached thereto, the patient interface being configured to interface with a user, and an inspiratory flow pathway extending from a distal end of the housing to the proximal end of the housing;
- a nitric oxide (NO) source positioned within the housing, the NO source configured to deliver NO-containing gas;
- a secondary drug source positioned within the housing, the secondary drug source configured to deliver a secondary drug; and
- a controller configured to control an amount of NO-containing gas delivered from the NO source and an amount of the secondary drug delivered from the secondary drug source using a control scheme, the control scheme having one or more inputs relating to at least one of the NO-containing gas, the secondary drug, the inspiratory flow pathway, and one or more inputs from the user, the controller being configured to utilize the control scheme to deliver the NO-containing gas and the secondary drug in a treatment pattern such the controller is configured to switch between delivery of the NO-containing gas, delivery of the secondary drug, and delivery of a gas without the NO-containing gas or the secondary drug to purge the inspiratory flow pathway,
- wherein the treatment pattern is derived by the controller using information related to at least one of a potential for interaction between the NO-containing gas and the secondary drug and a time for the NO-containing gas to wear off.

\* \* \* \* \*